(12) United States Patent
Wolfe et al.

(10) Patent No.: US 12,156,713 B2
(45) Date of Patent: Dec. 3, 2024

(54) SIGNAL ISOLATION MAGNETIC RESONANCE IMAGE (SIMRI) AND METHODS THEREOF

(71) Applicants: Tatiana Wolfe, Hilliard, OH (US); Caio C. Quini, São Paulo (BR); Philip J. Horner, Houston, TX (US); Matthew K. Hogan, Houston, TX (US); The METHODIST HOSPITAL, Houston, TX (US)

(72) Inventors: Tatiana Wolfe, Hilliard, OH (US); Caio C. Quini, São Paulo (BR); Philip J. Horner, Houston, TX (US); Matthew K. Hogan, Houston, TX (US)

(73) Assignee: THE METHODIST HOSPITAL, Houston, TX (US)

( * ) Notice: Subject to any disclaimer, the term of this patent is extended or adjusted under 35 U.S.C. 154(b) by 646 days.

(21) Appl. No.: 17/277,034

(22) PCT Filed: Sep. 17, 2019

(86) PCT No.: PCT/US2019/051442
§ 371 (c)(1),
(2) Date: Mar. 17, 2021

(87) PCT Pub. No.: WO2020/060997
PCT Pub. Date: Mar. 26, 2020

(65) Prior Publication Data
US 2021/0361167 A1    Nov. 25, 2021

Related U.S. Application Data

(60) Provisional application No. 62/732,181, filed on Sep. 17, 2018.

(51) Int. Cl.
*A61B 5/00*    (2006.01)
*A61B 5/055*   (2006.01)
(Continued)

(52) U.S. Cl.
CPC ............ *A61B 5/0042* (2013.01); *A61B 5/055* (2013.01); *G01R 33/50* (2013.01);
(Continued)

(58) Field of Classification Search
CPC ...... A61B 5/0042; A61B 5/055; G16H 30/20; G16H 30/40; G01R 33/50; G01R 33/5608; G01R 33/56341
See application file for complete search history.

(56) References Cited

U.S. PATENT DOCUMENTS 7,394,251 B2   7/2008  Lin
8,170,644 B2   5/2012  Du
(Continued)

OTHER PUBLICATIONS

International Search Report and Written Opinion for International Application No. PCT/US2019/051442 dated Dec. 6, 2019.
(Continued)

*Primary Examiner* — Katherine L Fernandez
*Assistant Examiner* — Brooke Lyn Klein
(74) *Attorney, Agent, or Firm* — Meunier Carlin & Curfman LLC

(57) ABSTRACT

The exemplified system and method facilitate an objective, non-invasive measurement of myelin quality and integrity in living brains based on isolation of myelin-specific magnetic relaxation constants in k-space. The system uses magnetic resonance (MR) signals to select signatures specific to, or associated with, myelin and its structure and to then encode the selected signatures into an image or model to which the quantitative myelin health information can be co-registered with 2D, 3D visualization, and tractography of the myelin-signal isolated MR information. The system also sets a model for digital hierarchical learning of biomedical signals in MR, and beyond, based on experimental data in which it executes the herein described signal isolation operations.

20 Claims, 37 Drawing Sheets

(51) Int. Cl.
G01R 33/50 (2006.01)
G01R 33/56 (2006.01)
G01R 33/563 (2006.01)
G16H 30/20 (2018.01)
G16H 30/40 (2018.01)
(52) U.S. Cl.
CPC ... *G01R 33/5608* (2013.01); *G01R 33/56341* (2013.01); *G16H 30/20* (2018.01); *G16H 30/40* (2018.01)

(56) References Cited

U.S. PATENT DOCUMENTS

| | | | |
|---|---|---|---|
| 8,890,525 B2 | 11/2014 | Kusahara et al. | |
| 2010/0296717 A1* | 11/2010 | Takizawa | G01R 33/5617 382/131 |
| 2014/0303480 A1* | 10/2014 | Lai | A61B 5/7214 600/410 |
| 2016/0220168 A1* | 8/2016 | Port | A61B 5/0042 |
| 2017/0123022 A1* | 5/2017 | Guerin | G01R 33/5612 |
| 2017/0261584 A1* | 9/2017 | James | G01R 33/4833 |

OTHER PUBLICATIONS

International Preliminary Report on Patentability issued for Application No. PCT/US2019/051442, dated Mar. 25, 2021.
Absinta, M., Sati, P. & Reich, D. S. Advanced MRI and staging of multiple sclerosis lesions. 12, 358-368 (2016).
Alonso-Ortiz E, Levesque IR, Pike GB. MRI-Based Myelin Water Imaging: A Technical Review. Magnetic Resonance in Medicine. 2015;73(1):70-81.
Amann M, Papadopoulou A, Andelova M, Magon S, Mueller-Lenke N, Naegelin Y, et al. Magnetization transfer ratio in lesions rather than normal-appearing brain relates to disability in patients with multiple sclerosis. Journal of Neurology. 2015;262(8):1909-17.
Ando S, Tanaka Y, Toyoda Y, Kon K. Turnover of myelin lipids in aging brain. Neurochemical Research. 2003;28(1):5-13.
Armstrong CL, Traipe E, Hunter JV, Haselgrove JC, Ledakis GE, Tallent EM, et al. Agerelated, regional, hemispheric, and mediallateral differences in myelin integrity in vivo in the normal adult brain. American Journal of Neuroradiology. 2004;25(6):977-84.
Arunachalam A. Enhancing the performance of accelerated MRI through preservation of acquisition SNR: An "aliased" k-space approach. Magnetic Resonance in Medicine. 2015;74(1):150-61.
Bando Y, Nomura T, Bochimoto H, Murakami K, Tanaka T, Watanabe T, et al. Abnormal morphology of myelin and axon pathology in murine models of multiple sclerosis. Neurochemistry International. 2015; 81:16-27.
Barbier EL, Marrett S, Danek A, Vortmeyer A, van Gelderen P, Duyn J, et al. Imaging cortical anatomy by high-resolution MR at 3.0T: Detection of the stripe of Gennari in visual area 17. Magnetic Resonance in Medicine. 2002;48(4):735-8.
Bartzokis G, Lu PH, Geschwind DH, Tingus K, Huang D, Mendez MF, et al. Apolipoprotein e affects both myelin breakdown and cognition: Implications for age-related trajectories of decline into dementia. Biological Psychiatry. 2007;62(12):1380-7.
Billiet T, Vandenbulcke M, Madler B, Peeters R, Dhollander T, Zhang H, et al. Agerelated microstructural differences quantified using myelin water imaging and advanced diffusion MRI. Neurobiology of Aging. 2015;36(6):2107-21.
Bjork M, Zachariah D, Kullberg J, Stoica P. A Multicomponent T-2 Relaxometry Algorithm for Myelin Water Imaging of the Brain. Magnetic Resonance in Medicine. 2016;75(1):390-402.
Bouhrara M, Spencer RG. Improved determination of the myelin water fraction in human brain using magnetic resonance imaging through Bayesian analysis of mcDESPOT. Neuroimage. 2016;127:456-71.
Branzoli F, Ercan E, Valabregue R, Wood ET, Buijs M, Webb A, et al. Differentiating between axonal damage and demyelination in healthy aging by combining diffusion-tensor imaging and diffusion-weighted spectroscopy in the human corpus callosum at 7 T. Neurobiology of Aging. 2016; 47:210-7.
Callaghan MF, Freund P, Draganski B, Anderson E, Cappelletti M, Chowdhury R, et al. Widespread age-related differences in the human brain microstructure revealed by quantitative magnetic resonance imaging. Neurobiology of Aging. 2014;35(8):1862-72.
Campbell, G. R., Smith, K. J., & Mahad, D. J. (2011). Mitochondrial Changes Associated with Demyelination: Consequences for Axonal Integrity. Mitochondrial Dysfunction in Neurodegenerative Disorders, 175-190. doi:10.1007/978-0-85729-701-3_11 10.1007/978-0-85729-701-3_11.
Carneiro AAO, Vilela GR, de Araujo DB, Baffa O. MRI relaxometry: Methods and applications. Brazilian Journal of Physics. 2006;36(1A):9-15.
Cercignani M, Embleton K, Parker GJM, Bozzali M. Group-averaged anatomical connectivity mapping for improved human white matter pathway visualisation. Nmr in Biomedicine. 2012;25(11):1224-33.
Cercignani M, Giulietti G, Dowell NG, Gabel M, Broad R, Leigh PN, et al. Characterizing axonal myelination within the healthy population: a tract-by-tract mapping of effects of age and gender on the fiber g-ratio. Neurobiology of Aging. 2017;49:109-18.
Chen YZ, Yi Q, Liu G, Shen X, Xuan LH, Tian Y. Cerebral white matter injury and damage to myelin sheath following whole-brain ischemia. Brain Research. 2013; 1495:11-7.
Clare S, Bridge H. Methodological issues relating to in vivo cortical myelography using MRI. Human Brain Mapping. 2005;26(4):240-50.
Cover KS, de Graaf W, Soriano AL, Kuijer JPA, Steenwijk MD, Geurts JJG, et al. Direct comparison of the quality of 32 echo MRI T2 decays used to measure myelin water in vivo at 3T and 1.5T using the decay roughness measure. Multiple Sclerosis Journal. 2011;17:S371-S2. p. 835.
Daneshi KE, Delva ML, Sparrey CJ. The Effects of Myelin Retraction and Detachment On Signal Conduction In A Computational Model of Damaged Axons. Journal of Neurotrauma. 2014;31(12):A8-A.
Davids M, Ruttorf M, Zollner FG, Schad LR. Fast and Robust Design of Time-Optimal k-Space Trajectories in MRI. IEEE Transactions on Medical Imaging. 2015;34(2):564-77.
De Santis S, Assaf Y, Jeurissen B, Jones DK, Roebroeck A. T-1 relaxometry of crossing fibres in the human brain. Neuroimage. 2016; 141:133-42.
Donahue CJ, Sotiropoulos SN, Jbabdi S, Hernandez-Fernandez M, Behrens TE, Dyrby TB, et al. Using Diffusion Tractography to Predict Cortical Connection Strength and Distance: A Quantitative Comparison with Tracers in the Monkey. Journal of Neuroscience. 2016;36(25):6758-70.
Elshafeey N Hi, Zinn PO, Colen RR. From K-space to Nucleotide: Insights Into the Radiogenomics of Brain Tumors. Magn Reson Imaging. 2017.
Fritz J, Raithel E, Thawait GK, Gilson W, Papp DF. Six-Fold Acceleration of High-Spatial Resolution 3D Space MRI of the Knee Through Incoherent k-Space Undersampling and Iterative ReconstructionFirst Experience. Investigative Radiology. 2016;51(6):400-9.
Gay CT, Rauch RA, Lancaster JL, Plaetke R, Dupont BR, Cody JD, et al. Magneticresonance-Imaging Relaxometry Of Delayed Myelination In The 18qsyndrome-Correlation With Myelin Basic-Protein Genotype. Annals of Neurology. 1995;38(3): on p. 520. Abstract 72.
Glasser MF, Goyal MS, Preuss TM, Raichle ME, Van Essen DC. Trends and properties of human cerebral cortex: Correlations with cortical myelin content. Neuroimage. 2014;93:165-75.
Glasser MF, Smith SM, Marcus DS, Andersson JLR, Auerbach EJ, Behrens TEJ, et al. The Human Connectome Project's neuroimaging approach. Nature Neuroscience. 2016;19(9):1175-87.
Glasser MF, Van Essen DC. Mapping Human Cortical Areas In Vivo Based on Myelin Content as Revealed by T1- and T2-Weighted MRI. Journal of Neuroscience. 2011;31(32):11597-616.
Grydeland H, Westlye LT, Walhovd KB, Fjell AM. Intracortical Posterior Cingulate Myelin Content Relates to Error Processing:

(56) References Cited

OTHER PUBLICATIONS

Results from T-1- and T-2-Weighted MRI Myelin Mapping and Electrophysiology in Healthy Adults. Cerebral Cortex. 2016;26(6):2402-10.

Harrison DM, Li X, Liu HJ, Jones CK, Caffo B, Calabresi PA, et al. High Field, Multiparametric Susceptibility MRI Measures of Myelin and Iron Loss in Multiple Sclerosis. Annals of Neurology. 2014;76:S113-S. M1716.

Hosny O, Highley JR, Simpson JE, Forster G, Wharton SB, Ince PG. Axonal number and myelin sheath degeneration in MRI hyperintense white matter lesions in the aging brain. Neuropathology and Applied Neurobiology. 2007;33(2):266-7.

Hunt BAE, Tewarie PK, Mougin OE, Geades N, Jones DK, Singh KD, et al. Relationships between cortical myeloarchitecture and electrophysiological networks. Proceedings of the National Academy of Sciences of the United States of America. 2016;113(47):13510-5.

Jbabdi S, Sotiropoulos SN, Haber SN, Van Essen DC, Behrens TE. Measuring macroscopic brain connections in vivo. Nature Neuroscience. 2015;18(11):1546-55.

Jelescu IO, Zurek M, Winters KV, Veraart J, Rajaratnam A, Kim NS, et al. In vivo quantification of demyelination and recovery using compartment-specific diffusion MRI metrics validated by electron microscopy. Neuroimage. 2016; 132:104-14.

Jonkman LE, Fleysher L, Steenwijk MD, Koeleman JA, de Snoo TP, Barkhof F, et al. Ultra-high field MTR and qR2*differentiates subpial cortical lesions from normal-appearing gray matter in multiple sclerosis. Multiple Sclerosis Journal. 2016;22(10):1306-14.

Kochunov P, Williamson DE, Lancaster J, Fox P, Cornell J, Blangero J, et al. Fractional anisotropy of water diffusion in cerebral white matter across the lifespan. Neurobiology of Aging. 2012;33(1):9-20.

Kulikova S, Hertz-Pannier L, Dehaene-Lambertz G, Poupon C, Dubois J. A New Strategy for Fast MRI-Based Quantification of the Myelin Water Fraction: Application to Brain Imaging in Infants. Plos One. 2016;11(10), 24 pages.

Kumar D, Nguyen T, Vartanian T, Gauthier S, Raj A. A spatially regularised approach to myelin water fraction imaging using T2 relaxometry. Multiple Sclerosis Journal. 2011; 17: S391-S2. p. 877.

Larson PEZ, Han MS, Krug R, Jakary A, Nelson SJ, Vigneron DB, et al. Ultrashort echo time and zero echo time MRI at 7T. Magnetic Resonance Materials in Physics Biology and Medicine. 2016;29(3):359-70.

Lasiene J, Matsui A, Sawa Y, Wong F, Horner PJ. Age-related myelin dynamics revealed by increased oligodendrogenesis and short internodes. Aging Cell. 2009;8(2):201-13.

Laule C, Vavasour IM, Kolind SH, Li DKB, Traboulsee TL, Moore GRW, et al. Magnetic resonance imaging of myelin. Neurotherapeutics. 2007;4(3):460-84.

Levesque IR, Chia CLL, Pike GB. Reproducibility of In Vivo Magnetic Resonance Imaging-Based Measurement of Myelin Water. Journal of Magnetic Resonance Imaging. 2010;32(1):60-8.

Li Y, Yang R, Zhang ZP, Wu YX. Chaotic-Like K-Space Trajectory for Compressed Sensing MRI. Journal of Medical Imaging and Health Informatics. 2015;5(2):415-21.

Liu F, Duan Y, Peterson BS, Kangarlu A. Compressed sensing MRI combined with Sense in partial k-space. Physics in Medicine and Biology. 2012;57(21):N391-N403.

Lublin, F. D. & Reingold, S. C. Defining the clinical course of multiple sclerosis: results of an international survey. National Multiple Sclerosis Society (USA) Advisory Committee on Clinical Trials of New Agents in Multiple Sclerosis. Neurology 46, 907-911 (1996).

Luo JH, Zhu YM, Li WQ, Croisille P, Magnin IE. MRI reconstruction from 2D truncated k-space. Journal of Magnetic Resonance Imaging. 2012;35(5):1196-206.

Markl M, Hennig J. Phase contrast MRI with improved temporal resolution by view sharing: k-space related velocity mapping properties. Magnetic Resonance Imaging. 2001;19(5):669-76.

Markus Kipp BS, Daphne Y.S. Vogel, Fabiola Puentes, Paul vander Valk, David Baker, Sandra Amor. Experimentalinvivoandinvitromodelsofmultiple sclerosis: EAE andbeyond. Multiple Sclerosis and Related Disorders. 2012;1:15-28.

McGuire C, Beyaert R, van Loo G. Death receptor signalling in central nervous system inflammation and demyelination. Trends in Neurosciences. 2011;34(12):619-28.

McCreary CR, Bjarnason TA, Skihar V, Mitchell JR, Yong VW, Dunn JF. Multiexponential T(2) and magnetization transfer MRI of demyelination and remyelination in murine spinal cord. Neuroimage. 2009;45(4):1173-82.

Pajevic S, Basser PJ, Fields RD. Role of Myelin Plasticity In Oscillations And Synchrony of Neuronal Activity. Neuroscience. 2014;276:135-47.

Peters A, Sethares CF. The fine structure of the aging brain. 72 East Newton Street, Boston, MA 02118: Boston University School of Medicine. Available from: http://www.bu.edu/agingbrain.

Petiet A, Aigrot MS, Stankoff B. Gray and White Matter Demyelination and Remyelination Detected with Multimodal Quantitative MRI Analysis at 11.7T in a Chronic Mouse Model of Multiple Sclerosis. Frontiers in Neuroscience. 2016;10pages.

Piedzia WI, Jasinski K, Kalita K, Bartel Z, Weglarz WP. Detection of Myelin Changes in Vivo Using High Field MRI. Multiple Sclerosis Journal. 2016;22(3):413. p. 20.

Pirko I, Johnson AJ. Neuroimaging of demyelination and remyelination models. Advances in Multiple Sclerosis and Experimental Demyelinating Diseases. 2008; 318:241-66. 33.

Powers BE, Lasiene J, Plemel JR, Shupe L, Perlmutter SI, Tetzlaff W, et al. Axonal Thinning and Extensive Remyelination without Chronic Demyelination in Spinal Injured Rats. Journal of Neuroscience. 2012;32(15):5120-5.

Preziosa, P. et al. Structural MRI correlates of cognitive impairment in patients with multiple sclerosis: A Multicenter Study. Hum Brain Mapp 37, 1627-1644 (2016).

Raddassi K, Yang JB, Kent S, Bradshaw E, Bourcier K, Seyfert-Margolis V, et al. Detection of Myelin Reactive CD4+Cells in the Peripheral Blood of Patients with Multiple Sclerosis using MHC Class II Tetramers. Clinical Immunology. 2009; 131:S150-S1.

Rovira, À. et al. Evidence-based guidelines: MAGNIMS consensus guidelines on the use of MRI in multiple sclerosis—clinical implementation in the diagnostic process. Nature Reviews Neurology 11, 471-482 (2015).

Samsonov AA. On optimality of parallel MRI reconstruction in k-space. Magnetic Resonance in Medicine. 2008;59(1):156-64.

Schulz BR, Vavasour I, Zhang J, MacKay A, Porter S, Fawcett D, et al. Evaluation of white matter in mild-to-moderate traumatic brain injury: Myelin water imaging and relationship with cognition. Brain Injury. 2016;30(5-6): on p. 496. Abstract 0045.

Serbruyns L, Leunissen I, van Ruitenbeek P, Pauwels L, Caeyenberghs K, Solesio-Jofre E, et al. Alterations in brain white matter contributing to age-related slowing of task switching performance: The role of radial diffusivity and magnetization transfer ratio. Human Brain Mapping. 2016;37(11):4084-98.

Shimony JS, Smyser CD, Wideman G, Alexopoulos D, Hill J, Harwell J, et al. Comparison of cortical folding measures for evaluation of developing human brain. Neuroimage. 2016; 125:780-90.

Spencer Noakes TL HR, Nieman BJ. Partitioning k-space for cylindrical threedimensional rapid acquisition with relaxation enhancement imaging in the mouse brain. NMR Biomed. 2017.

Sriram S. Role of glial cells in innate immunity and their role in CNS demyelination. Journal of Neuroimmunology. 2011;239(1-2):13-20.

Staal J, Fields RD, Kilpatrick T. Mechanisms underlying activity-dependent myelin plasticity. Multiple Sclerosis Journal. 2015;21(14):NP6-NP.

Stankoff B, Jadasz JJ, Hartung HP, Kury P, Zalc B, Lubetzki C. Repair strategies for multiple sclerosis: challenges, achievements and perspectives. Current Opinion in Neurology. 2016;29(3):286-92.

(56) References Cited

OTHER PUBLICATIONS

Steiger TK, Weiskopf N, Bunzeck N. Iron Level and Myelin Content in the Ventral Striatum Predict Memory Performance in the Aging Brain. Journal of Neuroscience. 2016;36(12):3552-8.

Stikov N, Campbell JSW, Stroh T, Lavelee M, Frey S, Novek J, et al. In vivo histology of the myelin g-ratio with magnetic resonance imaging. Neuroimage. 2015;118:397-405.

Ugurbil K, Xu JQ, Auerbach EJ, Moeller S, Vu AT, Duarte-Carvajalino JM, et al. Pushing spatial and temporal resolution for functional and diffusion MRI in the Human Connectome Project. Neuroimage. 2013;80:80-104.

Van Essen DC, Glasser MF. In vivo architectonics: A cortico-centric perspective. Neuroimage. 2014;93:157-64.

van Gelderen P, Jiang X, Duyn JH. Effects of magnetization transfer on T-1 contrast in human brain white matter. Neuroimage. 2016;128:85-95.

Velikina JV, Alexander AL, Samsonov A. Accelerating MR Parameter Mapping Using Sparsity-Promoting Regularization in Parametric Dimension. Magnetic Resonance in Medicine. 2013;70(5):1263-73.

Wender M, Adamczewskagoncerzewicz Z, Dorszewska J. Myelin Proteins In Aging Human Brain. Molecular and Chemical Neuropathology. 1991;14(1):1-10.

Wild JM, Paley MNJ, Viallon M, Schreiber WG, van Beek EJR, Griffiths PD. k-space filtering in 2D gradient-echo breath-hold hyperpolarized He-3 MRI: Spatial resolution and signal-to-noise ratio considerations. Magnetic Resonance in Medicine. 2002;47(4):687-95.

Wilhelm MJ, Ong HH, Wehrli SL, Li C, Tsai PH, Hackney DB, et al. Direct magnetic resonance detection of myelin and prospects for quantitative imaging of myelin density. Proceedings of the National Academy of Sciences of the United States of America. 2012;109(24):9605-10.

Woodruff RH, Franklin RJM. Demyelination and remyelination of the caudal cerebellar peduncle of adult rats following stereotaxic injections of lysolecithin, ethidium bromide, and complement/anti-galactocerebroside: A comparative study. Glia. 1999;25(3):216-28.

Wooten EW. Spectroscopic Lineshapes, k-Space Coverage, and Image Properties in MRI. Concepts in Magnetic Resonance Part A. 2010;36A(3):187-209.

Yeh FC, Verstynen TD, Wang YB, Fernandez-Miranda JC, Tseng WYI. Deterministic Diffusion Fiber Tracking Improved by Quantitative Anisotropy. Plos One. 2013;8(11).

Zhang G, Xiao G, Dai Z, Shen Z, Li S, Wu R. Accelerated reconstruct MRI T2 map from sub-sampled K-space Data using compressed sensing at 7.0 Tesla. Journal of Neurology 2014. Abstract pp. 3195.

Zhao TD, Cao M, Niu HJ, Zuo XN, Evans A, He Y, et al. Age-Related Changes in the Topological Organization of the White Matter Structural Connectome Across the Human Lifespan. Human Brain Mapping. 2015;36(10):3777-92.

\* cited by examiner

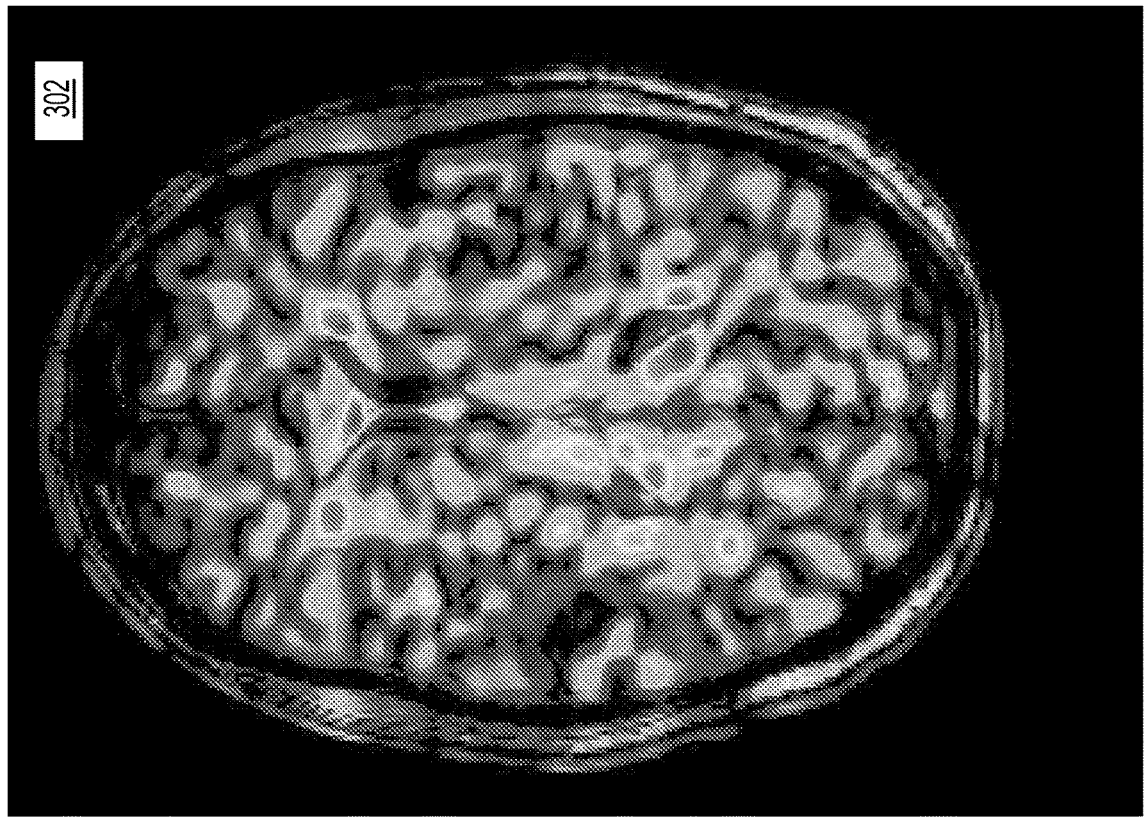
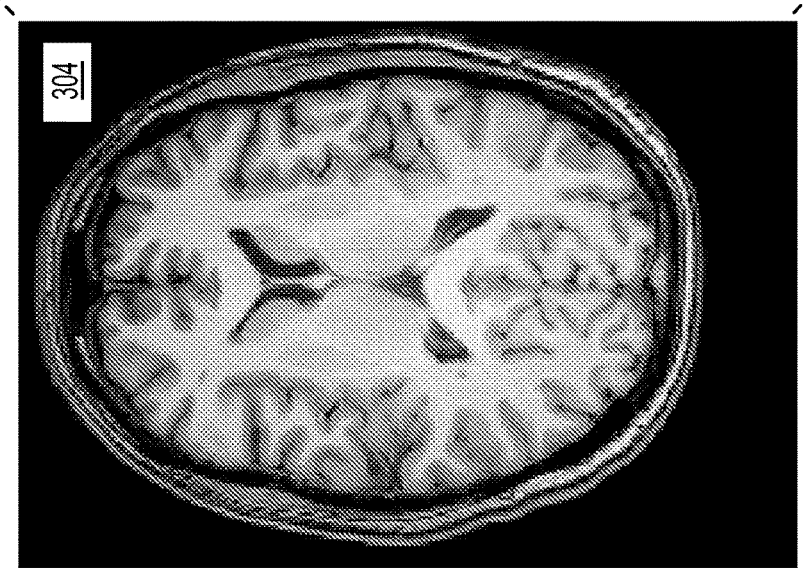
FIG. 3

T1-WEIGHTED MRI
LYSOLECTHIN
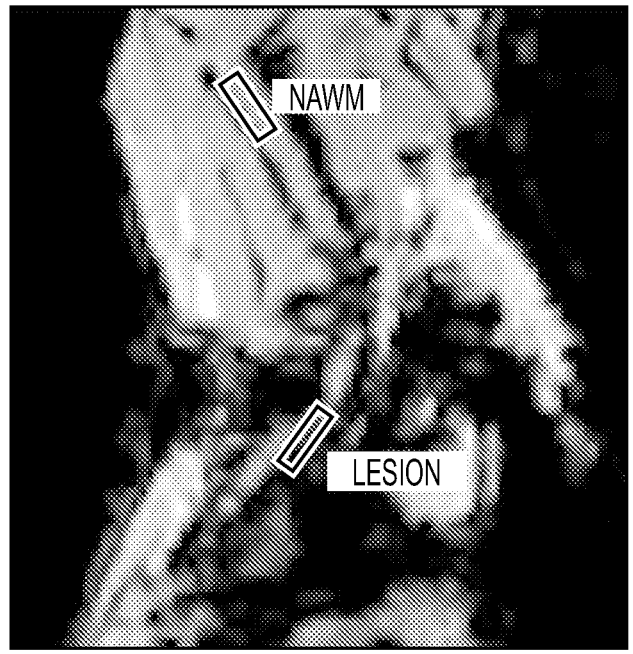
SALINE
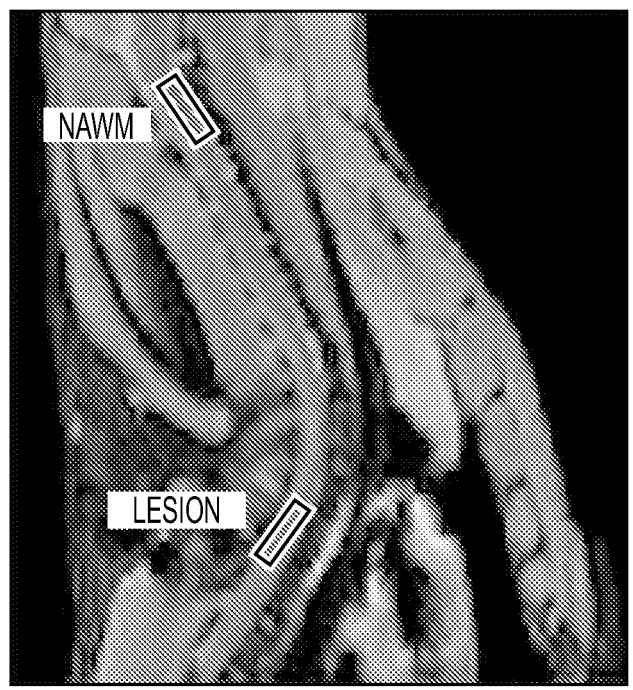
*FIG. 15A*

| T2 RELAXOMETRY OF INDIVIDUAL k-SPACE COMPARTMENTS (SUBJECT'S AGE = 50 y) | | | |
|---|---|---|---|
| FOURIER SPECTRAL LINE (ky; MATRIX 256x256) | FIT TYPE | $R^2$ | $T_2$ (ms) |
| CENTRAL, 128 | 1ST ORDER EXP. | 0.9995 | 58.8 |
| 130 | 1ST ORDER EXP. | 0.9993 | 58.7 |
| 135 | 1ST ORDER EXP. (>=20 ms) | 0.9747 | 51.3 |
| 137 | 1ST ORDER EXP. (<=60 ms) | 0.9994 | 10.0 * |
| 140 | 2ND ORDER EXP. | 0.9680 | 18.9 * |
| 144 | 1ST ORDER EXP. (<=120 ms) | 0.9864 | 35.6 |
| 144 | 2ND ORDER EXP. (<=160 ms) | 0.9996 | 23.3 * / 154.8 |
| 149 | 1ST ORDER EXP. (<=160 ms) | 0.9879 | 26.5 * |
| 154 | 1ST ORDER EXP. (>=20 ms) | 0.9974 | 93.0 |
| 158 | 1ST ORDER EXP. (20<TE<160 ms) | 0.9932 | 47.3 |
| 160 | 1ST ORDER EXP. (<=100 ms) | 0.9717 | 29.9 |
| 164 | 1ST ORDER EXP. (<=80 ms) | 0.9984 | 16.4 * |
| 168 | 1ST ORDER EXP. (<=60 ms) | 0.9831 | 18.5 * |

*SPECTRAL LINES WITH INTER-MYELIN WATER CHARACTERISTICS T2 (i.e. 10-30 ms/$R^2$>0.96).

FIG. 19

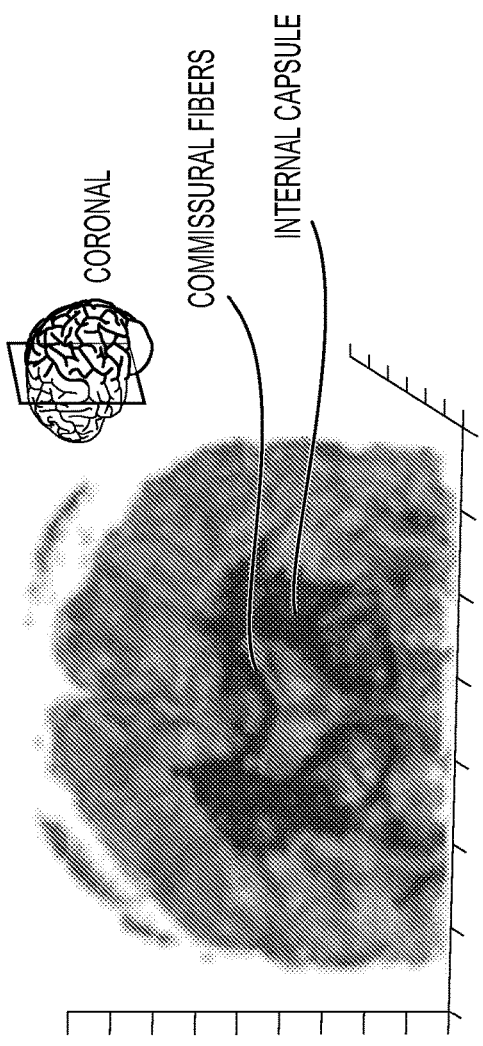
FIG. 21

MYELIN COMPACTION MAP {2D ISOCONTOURS}
(WHOLE BRAIN, RELATIVE SCALE 1 - 4)

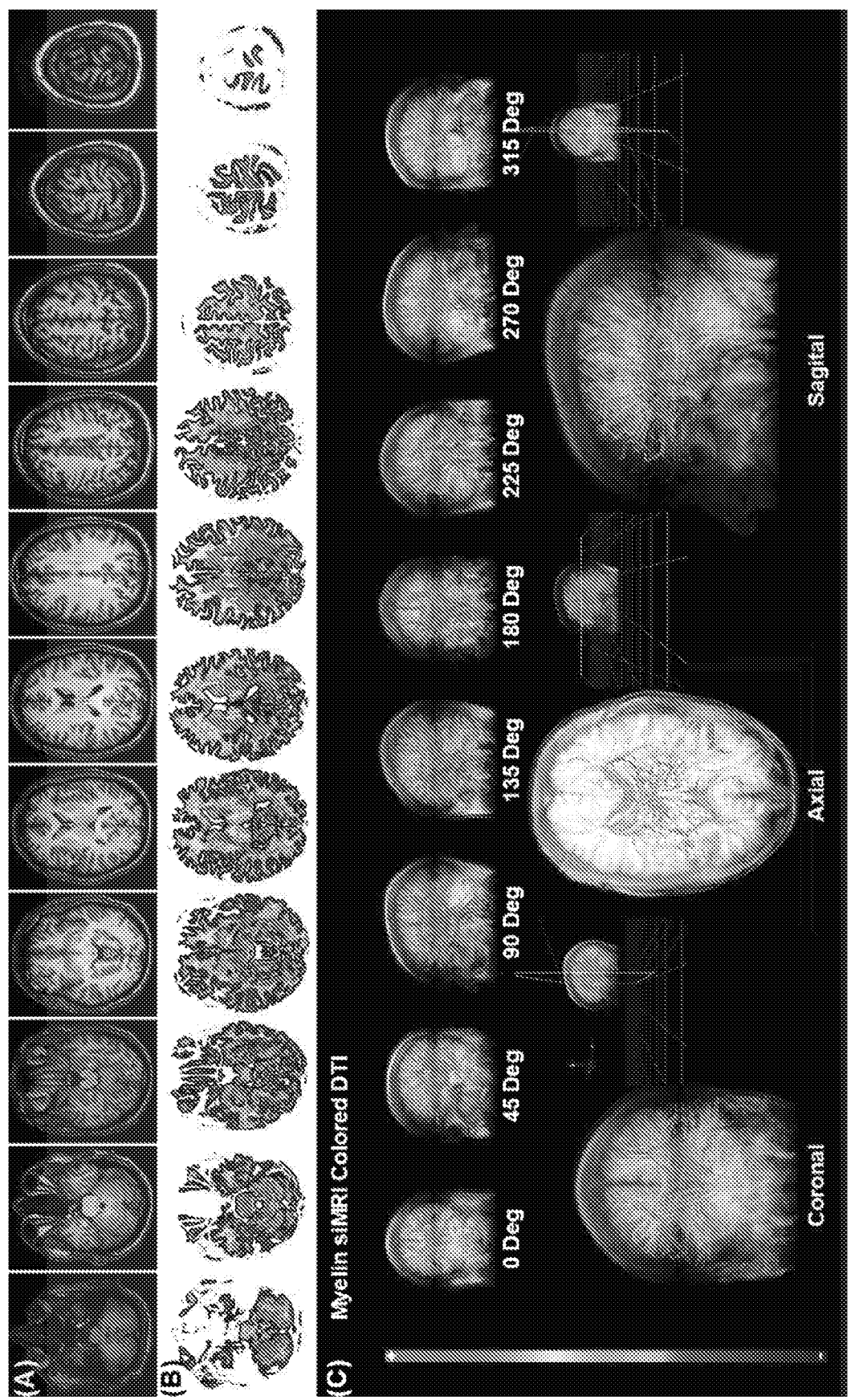
FIG. 25A-C

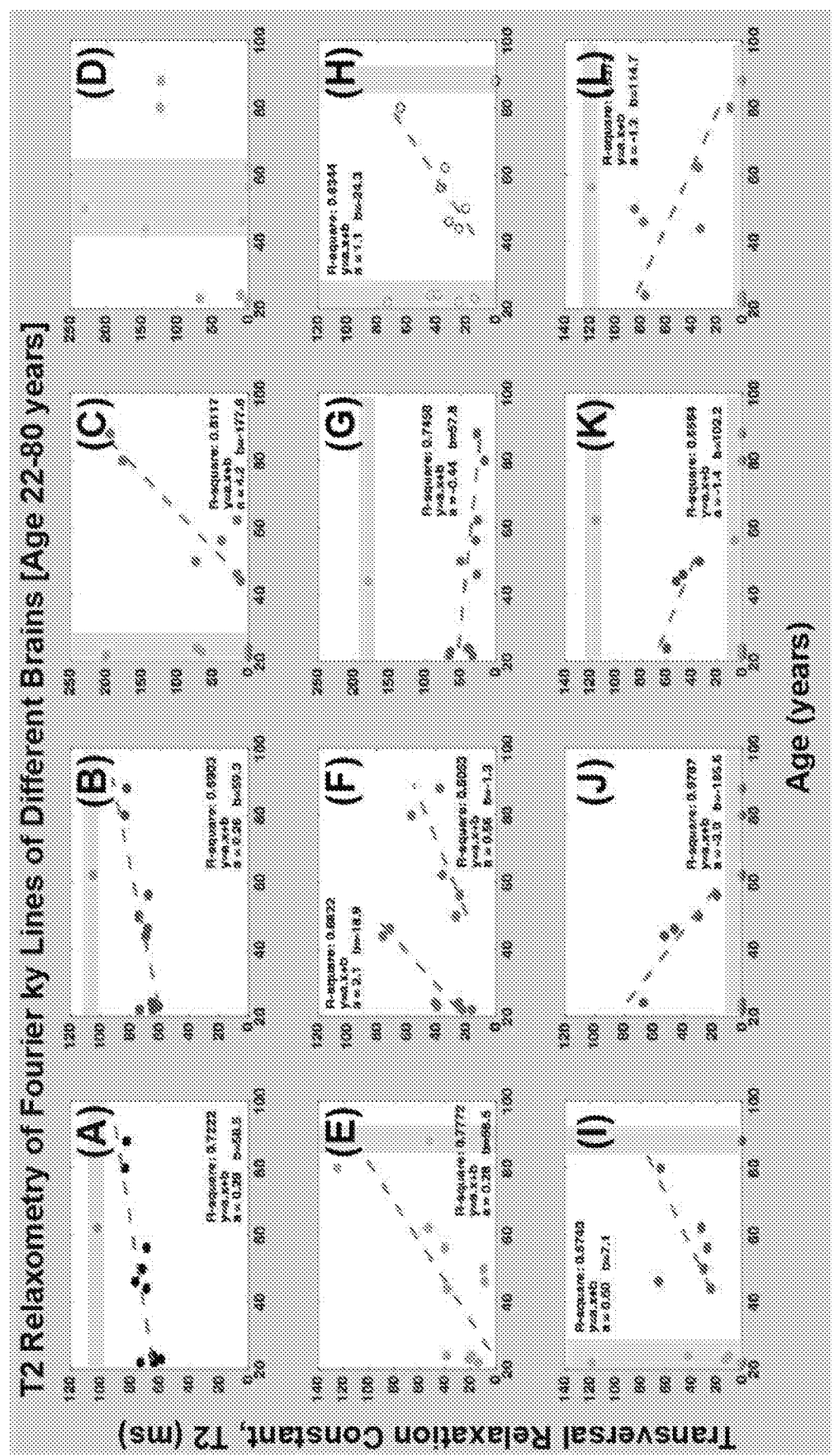
FIG. 26A-L

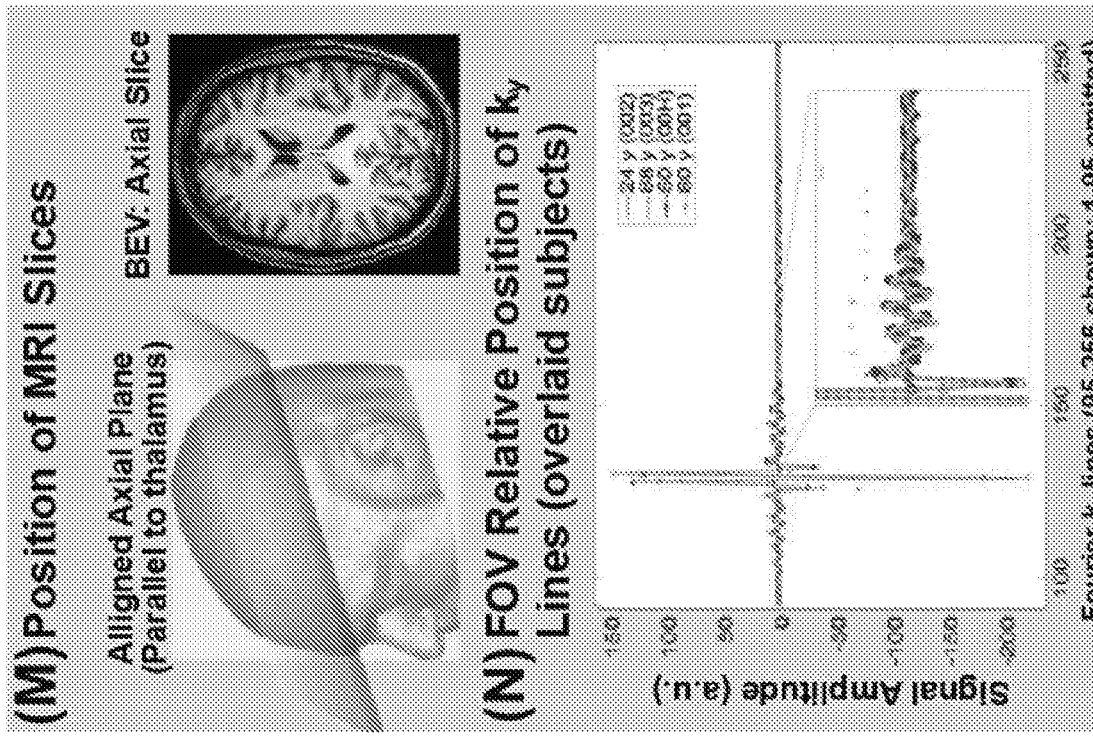
FIG. 26M-N

SIGNAL ISOLATION MAGNETIC RESONANCE IMAGE (SIMRI) AND METHODS THEREOF

RELATED APPLICATION

This application is a national stage application filed under 35 U.S.C. § 371 of PCT/US2019/051442 filed Sep. 17, 2019, which claims priority to, and the benefit of, U.S. Provisional Patent Application No. 62/732,181, filed Sep. 17, 2018, entitled "Signal Isolation Magnetic Resonance Image (SIMRI) and Methods thereof," each of which is incorporated by reference herein in its entirety.

BACKGROUND

Myelin is a protein that forms insulation necessary for conduction of signals between neurons in the brain. Healthy myelin is essential for proper neurological function. Myelin structure changes in order to allow appropriately timed and coordinated information exchange between different areas of the brain. Impairment of myelination is clinically associated with neural dysfunction in development, aging, diseases, and injury, including neurodegenerative diseases such as multiple sclerosis (MS), concussion, stroke, spine, brain trauma, metabolic diseases, among others. Recovery from any of these conditions requires repair of myelin.

Impartial, direct detection and imaging of the myeloarchitecture of living systems is a challenge even for researchers seeking insight into the relevance of myelin integrity, degeneration and plasticity in human behavior. Current measurements of myelin in humans are based on indirect or analytic interpretations of radiologic signals, e.g., via magnetic resonance (MR) images that collect macroscopic information of lipid content and distribution, and positron emission tomography (PET) that rely on molecular radioactive markers that, if penetrated into the brain, bind to popular proteins in external myelin layers. Discrete structural details of the myeloarchitecture remain intangible even with high-field MR imaging due to the inherent noise associated with microscale compartments of intermyelin water in gray and white matters (WM). Hence the field of human studies lacks a direct imaging assessment that can discriminate between intact, degenerating and regenerating myelin.

SUMMARY

The exemplified system and method facilitate an objective, non-invasive measurement of myelin quality and integrity in living brains, spinal cords, and/or nerves of the body based on isolation of myelin-associated magnetic relaxation constants in k-space. The system uses, in some embodiments, magnetic resonance (MR) signals to select signatures specific to myelin and its structure and to then encode the selected signatures into an image or model to which the myelin health information can be co-registered with 2D/3D visualization, and/or tractography of the myelin-signal isolated MR information.

In an aspect, a method is disclosed for in-vivo imaging of myelin. The method includes obtaining, by one or more processors, magnetic resonance data (e.g., raw MR data, DICOM data or image files) (e.g., wherein the magnetic resonance data comprises one or more echo measurements and/or one or more weighted MR maps each having one or more magnetic-resonance data selected from the group consisting of, but not limited to, T1 data, T2 data, T2* data, MR diffusion data, MPRAGE data, gradient-echo data, spin-echo data, EPI data, BOLD data, proton density data, susceptibility data, magnetization transfer data, spin labeling data, flow data, and combination thereof) acquired from a magnetic resonance system (e.g., a MRI system having T1 and T2 measurements); generating, by the one or more processors, at least one k-space map (e.g., having magnitude and/or phase components of a raw k-space or a Fourier transform performed on the raw image data associated with a slice) of the obtained magnetic resonance data; amplifying, by the one or more processors, spatiotemporal signatures of magnetic relaxation associated with myelin-restricted water (including intermyelin water/intermyelin water fraction) in the at least one k-space map, or components thereof, (e.g., magnitude component having associated T2 measurement values between about 5 milliseconds and about 35 milliseconds for a 3-Tesla acquired image) (e.g., wherein the amplification is based on an amplification profile that is inversely proportional to the T2 measurement values) to generate a myelin-amplified k-space map (e.g., of each echo and/or of one or more magnetic-resonance measurement) (e.g., to directly detect myeloarchitecture in the scanned tissue); and reconstructing, by the one or more processors, in part, the myelin-amplified k-space map to generate a MRI quantification and/or visualization dataset of myelin associated tissue structure (e.g., wherein the reconstruction includes application of Inverse Fourier Transform (e.g., IFFT) to the myelin-amplified k-space map combined with a phase component of the k-space map); wherein the generated MRI quantification and/or visualization dataset of the myelin associated tissue structure are outputted to a display or to storage)(e.g., for subsequent display or analysis or optimizing sequences of coil design, e.g., organized, classified, and/or stored on a data library/collection for learning, comparative learning, machine learning, or digital memory of research or medically relevant knowledge buildup).

In some embodiments, the step of amplifying the spatiotemporal signatures of magnetic relaxation associated with myelin-restricted water includes amplifying based on an amplification profile of the T1 measurement values (e.g., wherein the amplification profile comprises weight values that are applied to one or more region selected from the group consisting of k-space points, regions, patterns, patches) (e.g., wherein the weights are determined by a machine learning algorithm, artificial intelligence, Monte Carlo simulation, and/or analytically). In some embodiments, the step of amplifying the spatiotemporal signatures of myelin-restricted water further includes suppressing at least one non-myelin related signature in the image.

In some embodiments, the spatiotemporal signatures of magnetic relaxation associated with myelin-restricted water in the at least one generated k-space map is spatially located at myelin-associated regions of the at least one k-space map, wherein the at least one generated k-space map comprises data associated with one or more echoes of one or more magnetic contrast.

In some embodiments, the myelin-associated regions of the k-space map are determined by evaluating and removing, by the one or more processors, portions of the at least one k-space map that does affect measured values (e.g., measured image intensity in evaluated region of interests (ROIs)) associated with myelin-associated or associated regions of interests (e.g., wherein the affected values associated with myelin-associated or associated regions can be identified and accepted/rejected by a human expert, a machine learning algorithm, a database comparison or by artificial intelligence, hardware or wetware).

In some embodiments, the myelin-associated regions of the k-space map are determined by: iteratively applying, by the one or more processors, (e.g., in successive stages), a plurality of evaluative patches (e.g., a nulling patch or a saturating patch to iteratively remove, null, saturate, distinguish, contrast) to the at least one k-space map (i.e., magnitude component of the raw k-space data or Fourier transform, or other forward transforms such as Laplacian, Hough, Radon, wavelet, sine or cosine, of the obtained raw image data), wherein in each successive stage, one of the plurality of evaluative patches is applied (e.g., in a pre-defined scanning sequence or random sampling manner) to the at least one k-space map to produce a modified k-space map; reconstructing, by the one or more processors, at each iteration of the successive stages, an MRI image or dataset from the modified k-space map; evaluating, by the one or more processors, at each iteration of the successive stages, an intensity value (e.g., total intensity) associated with one or more myelin-specific or associated regions of interest in the reconstructed MRI image or dataset; selecting, by the one or more processors, one or more evaluative patches of the plurality of evaluative patches, wherein the selected patches are global maximum or global minimum of intensity values among a set of intensity values determined from the plurality of evaluative patches; and shaping, by the one or more processors, the selected patch to correspond to the myelin-associated region of the at least one k-space map (e.g., wherein the shaping is performed by (i) calculating a T2 relaxometry value for a plurality of points (e.g., each of the points in the selected patch) in the selected patch, (ii) evaluating a fit, via a fit function (e.g., mono-exponential fit function), of each of the calculated T2 relaxometry value among the plurality of calculated T2 relaxometry values associated with the points, and (ii) adding one or more points in the selected patch to the myelin-specific region of the k-space map based on the evaluated fit).

In some embodiments, the evaluative patch has a spiral, an asymmetric distribution shape, or a polygonal shape (e.g., wherein the polygonal shape is selected from the group consisting of a square, a rectangle, a circle, a toroid, a point, triangle, pie-wedge, and an oval).

In some embodiments, the method further includes generating, by the one or more processors, at least one k-space map of the obtained magnetic resonance data for each slice of a magnetic resonance data set; amplifying, by the one or more processors, spatiotemporal signatures of myelin-restricted water magnetic relaxation in the at least one k-space map based on the amplification profile to generate a myelin-amplified k-space map for each slice of the magnetic resonance dataset; and reconstructing, by the one or more processors, the myelin-amplified k-space map to generate a given MRI quantification and/or visualization dataset of myelin associated tissue structure of each slice of the raw image dataset, wherein the generated MRI quantification and/or visualization dataset of a plurality of slices are used to generate a three-dimensional MRI visualization and/or analysis.

In some embodiments, the method includes co-registering, by the one or more processors, the generated MRI quantification and/or visualization dataset of the myelin associated structure with a second MRI modality (e.g., a high resolution T1-weighted map), wherein the generated MRI quantification and/or visualization dataset of the myelin associated structure is subsequently overlaid over the visualization of the second MRI modality.

In some embodiments, the method further includes calculating, by the one or more processors, one or more metrics (e.g., correlation power, machine-learned comparative indices, tissue classification indices, and/or tissue modeling coefficients, etc.) between i) one or more myelin compaction indices derived from the generated MRI quantification and/or visualization dataset of the myelin associated structure and ii) other MRI quantities (e.g., diffusion tensor components associated with the T1 echoes, gray level components associated with the T1 echoes, etc.); wherein the calculated one or more metrics is outputted to the display or to the storage (e.g., for subsequent display and/or analysis).

In some embodiments, the generated MRI quantification and/or visualization dataset includes a myelin compaction map or a myelin compaction dataset.

In some embodiments, the method further includes generating, by the one or more processors, a colored myelin compaction map by applying a color profile (e.g., S-shaped profile) across intensity values of the myelin compaction map, wherein the colored myelin compaction map is outputted to the display or to the storage (e.g., for subsequent display and/or analysis).

In some embodiments, the method includes generating, by the one or more processors, a fiber tractography image based on the generated MRI quantification and/or visualization dataset of the myelin associated tissue structure (e.g., wherein the generated fiber tractography image is used for neuro navigation (e.g., for surgical planning), for neuro-functional constructs (e.g., for therapy assessments), and for metrics (e.g., for nerve restoration therapies, including optical and other brain nerves as well as peripheral nerve de- and regeneration imaging)).

In some embodiments, the MRI quantification and/or visualization dataset includes visualization of myelin integrity including visualization and/or quantified data of intact myelin, degenerating myelin, and regenerating myelin when present in a subject (e.g., animal model, patients, harvested or cultured tissues) associated with the obtained magnetic resonance data.

In some embodiments, the MRI quantification and/or visualization dataset includes visualization and/or quantified data of myelin degeneration when myelin degeneration is present in a subject associated with the obtained magnetic resonance data.

In some embodiments, the MRI quantification and/or visualization dataset includes visualization and/or quantified data of myelin plasticity, or associated degradation thereof (e.g., from an inflammation or inflammatory process).

In some embodiments, the generated MRI quantification and/or visualization dataset of the myelin associated tissue structure is used to detect a myelin structure-related pathology or condition selected from the group consisting of, including but not limited to, multiple sclerosis, Parkinson's disease, Alzheimer's disease, spinal cord injury, brain injury, concussion, mild repeated neural injury, cancer of the nervous system, myelopathy, white matter/axonal damage after surgery of the nervous system, age-related cognitive decline, and age-related motor decline.

In some embodiments, the generated MRI quantification and/or visualization dataset of the myelin associated tissue structure is used to detect a myelin structure-related evaluation of post tumor resection margins, post-surgery and/or post radiotherapy in the nervous system or in nerves of the body (e.g. the optical nerve alone, the femoral head nerve branch, the hepatic nerves etc.).

In some embodiments, the generated MRI quantification and/or visualization dataset of the myelin associated tissue structure is used to detect and/or inform myelin-related developmental assessments, myelin-related developmental disorders, improvements of life style changes, exercise performance, drug addiction, drug efficacy, neuronal function in developmental population (young adults), motor learning, therapy, games, behavioral, prenatal assessment of neurological development, athletic performance.

In some embodiments, the generated MRI quantification and/or visualization dataset of the myelin associated tissue structure is used alone or in combination with other biomedical imaging systems.

In some embodiments, at least one of the one or more processors is a component (e.g., a part of the imaging engine) of the magnetic resonance system.

In some embodiments, at least one of the one or more processors is external to the magnetic resonance system.

In another aspect, a system (e.g., analysis system) is disclosed. The system includes one or more processors; and a memory having instructions stored thereon, wherein execution of the instructions by the one or more processors cause the one or more processors to perform the steps of any one of the above method.

In some embodiments, the instructions, when executed by the one or more processors, cause the one or more processors to obtain magnetic resonance data (e.g., raw MR data, DICOM data or image files) (e.g., wherein the magnetic resonance data comprises one or more echo measurements and/or one or more weighted MR maps each having one or more magnetic-resonance data selected from the group consisting of, but not limited to, T1 data, T2 data, T2* data, MR diffusion data, MPRAGE data, gradient-echo data, spin-echo data, EPI data, BOLD data, proton density data, susceptibility data, magnetization transfer data, spin labeling data, flow data, and combination thereof) acquired from a magnetic resonance system (e.g., a MRI system having T1 and T2 measurements); generate at least one k-space map (e.g., having magnitude and/or phase components of the raw k-space data or a Fourier transform, or other forward transforms such as Laplacian, Hough, Radon, wavelet, sine or cosine, performed on the raw image data associated with a slice) of the obtained magnetic resonance data; amplifying, by the one or more processors, spatiotemporal signatures of magnetic relaxation associated with myelin-restricted water (including intermyelin water/intermyelin water fraction) in the at least one k-space map, or components thereof, to generate a myelin-amplified k-space map (e.g., of each echo and/or of one or more magnetic-resonance measurement contrasts) (e.g., to directly detect myeloarchitecture in the scanned tissue); and reconstructing, by the one or more processors, in part, the myelin-amplified k-space map to generate a MRI quantification and/or visualization dataset of myelin associated tissue structure (e.g., wherein the reconstruction includes application of Inverse Fourier Transform (e.g., IFFT), or other inverse transforms or operations such as inverse Laplacian transform, inverse Hough transform, inverse Radon transform, inverse wavelet operations, inverse sine or cosine, operations, to the myelin-amplified k-space map combined with a phase component of the k-space map); wherein the generated MRI quantification and/or visualization dataset of the myelin associated tissue structure are outputted to a display or to storage (e.g., for subsequent display or analysis or optimizing sequences of coil design, e.g., organized, classified, and/or stored on a data library/collection for learning, comparative learning, machine learning, or digital memory of research or medically relevant knowledge buildup).

In another aspect, a non-transitory computer readable medium is disclosed having instructions stored thereon, wherein execution of the instructions by a processor cause the one or more processors to perform steps of any one of the above-recited method. In some embodiments, the instructions, when executed by the one or more processors, cause the one or more processors to obtain magnetic resonance data (e.g., raw MR data, DICOM data or image files) (e.g., wherein the magnetic resonance data comprises one or more echo measurements and/or one or more weighted MR maps each having one or more magnetic-resonance contrast data selected from the group consisting of, but not limited to, T1 data, T2 data, T2* data, MR diffusion data, MPRAGE data, gradient-echo data, spin-echo data, EPI data, BOLD data, proton density data, susceptibility data, magnetization transfer data, spin labeling data, flow data, and combination thereof) acquired from a magnetic resonance system (e.g., a MRI system having T1 and T2 measurements); generate at least one k-space map (e.g., having magnitude and/or phase components of a Fourier transform, or other forward transforms such as Laplacian, Hough, Radon, wavelet, sine or cosine, performed on the raw image data associated with a slice) of the obtained magnetic resonance data; amplifying, by the one or more processors, spatiotemporal signatures of magnetic relaxation associated with myelin-restricted water (including intermyelin water/intermyelin water fraction) in the at least one generated k-space map, or components thereof, to generate a myelin-amplified k-space map (e.g., of each echo and/or of one or more magnetic-resonance measurement contrasts) (e.g., to directly detect myeloarchitecture in the scanned tissue); and reconstructing, by the one or more processors, in part, the myelin-amplified k-space map to generate a MRI quantification and/or visualization dataset of myelin associated tissue structure (e.g., wherein the reconstruction includes application of Inverse Fourier Transform (e.g., IFFT) or other inverse transforms or operations such as inverse Laplacian transform, inverse Hough transform, inverse Radon transform, inverse wavelet operations, inverse sine or cosine, operations, to the myelin-amplified k-space map combined with a phase component of the generated k-space map); wherein the generated MRI quantification and/or visualization dataset of the myelin associated tissue structure are outputted to a display or to storage (e.g., for subsequent display or analysis or optimizing sequences of coil design, e.g., organized, classified, and/or stored on a data library/collection for learning, comparative learning, machine learning, or digital memory of research or medically relevant knowledge buildup).

In another aspect, a magnetic-resonance imaging (MRI) system is disclosed comprising: a magnetic-field source (e.g., high-magnetic field source); a radio-frequency emitter; and a controller having one or more processors and a memory, wherein the memory has instructions stored thereon, wherein execution of the instructions by the one or more processors cause the one or more processors to perform any of the above-recited method.

In another aspect, a method (a general discovery methodology for signal isolation in magnetic-resonance-imaging and other modalities) is disclosed of isolating a biologically controlled measurand for in-vivo imaging of a physiological system. The method includes obtaining, by one or more processors, raw image data of a biologically controlled measurand acquired from a non-invasive imaging system (e.g., ultrasound, computed tomography, PET, laser, optical tomography and fiber optical imaging, photoacoustic, reflection of visible, NIR or UV light or X-rays or Gamma-rays); generating, by the one or more processors, at least one k-space map (e.g., a k-space map data set associated with a slice), of a real and/or imaginary component thereof, of the obtained raw image data; amplifying, by the one or more processors, a pre-defined signature of the biologically controlled measurand (e.g., a signature of the biologically controlled measurand in a spatial frequency domain, a signature of relaxation of the biologically controlled measurand, or a spatiotemporal signature of the biologically controlled measurand) in the at least one k-space map to generate a measurand-amplified k-space map; and reconstructing, by the one or more processors, based on the generated measurand-amplified k-space map to generate a quantification and/or visualization dataset of an isolated measurand associated tissue structure; wherein the generated quantification and/or visualization dataset of the isolated measurand associated tissue structure is outputted to a display or to storage (e.g., for subsequent display).

In some embodiments, the pre-defined signature of the biologically controlled measurand has a predominantly spatiotemporal signal-component-of-interest signature.

In some embodiments, the pre-defined signature of the biologically controlled measurand are determined by evaluating and removing, by the one or more processors, portions of the at least one k-space map that does not affect measured values associated with the biologically controlled measurand or associated regions of interests.

In some embodiments, the pre-defined signature is determined by: iteratively applying, by the one or more processors (e.g., in successive stages), a plurality of evaluative patches (e.g., a nulling patch or a saturation patch, wherein a patch has one or more pixels) to the k-space map (e.g., a magnitude component of the raw k-space data or a Fourier transform, or other forward transforms such as Laplacian, Hough, Radon, wavelet, sine or cosine, of the obtained raw data), wherein in each successive stage, one of the plurality of evaluative patches is applied to the k-space map; reconstructing, by the one or more processors, at each iteration, an imaging dataset; selecting, by the one or more processors, one or more evaluative patches of the plurality of evaluative patches, wherein the selected patches have a best metric selected from among a set of determined metrics for the plurality of evaluative patches; and shaping, by the one or more processors, the selected patch to correspond to the measurand-specific region of the k-space map.

In some embodiments, the pre-defined signature of the biologically controlled measurand has a predominantly signal-of-relaxation and/or magnetic energy loss in the signal-component-of-interest signature.

In some embodiments, the pre-defined signature of the biologically controlled measurand has a predominantly proton density shift in the signal-component-of-interest signature.

In some embodiments, the pre-defined signature of the biologically controlled measurand has a predominantly magnetization transfer (from fat carbon-hydrogen to water molecules, or from iron to water, etc.) in the signal-component-of-interest signature.

In some embodiments, the pre-defined signature of the biologically controlled measurand has a predominantly precession change (e.g., in T1) in the signal-component-of-interest signature.

In some embodiments, the pre-defined signature of the biologically controlled measurand has a predominantly spatiotemporal frequency signal-component-of-interest signature.

In some embodiments, the pre-defined signature is determined by: iteratively applying, by the one or more processors, varying gains in a selected echo, to the k-space map (e.g., a magnitude component of the raw k-space data or a Fourier transform, or other forward transforms such as Laplacian, Hough, Radon, wavelet, sine or cosine, of the obtained raw data); reconstructing, by the one or more processors, at each iteration, an imaging dataset; and selecting, by the one or more processors, a gain of the evaluated gains, wherein the selected gain has a best metric selected from among a set of determined metrics for the plurality of evaluative gains.

In some embodiments, the pre-defined signature of the biologically controlled measurand has a predominantly spatial-frequency signal-component-of-interest signature.

In some embodiments, the pre-defined signature is determined by: applying, by the one or more processors, varying gains to the k-space map (e.g., a magnitude component of the raw k-space data or a Fourier transform, or other forward transforms such as Laplacian, Hough, Radon, wavelet, sine or cosine, of the obtained raw data); reconstructing, by the one or more processors, at each iteration, an imaging dataset; and selecting, by the one or more processors, a gain of the evaluated gains, wherein the selected gain has a best metric selected from among a set of determined metrics for the plurality of evaluative gains.

In some embodiments, the generated quantification and/or visualization dataset of an isolated measurand associated tissue structure provides a contrast for an isolation of the signature of relaxation of the biologically controlled measurand (e.g., wherein the contrast is determined by machine learning analysis, multi-dimensional analysis, pattern analysis, multi-contrast comparison analysis, and/or feature classification analysis).

In some embodiments, the biologically controlled measurand is selected from the group consisting of myelin sheaths and blood.

In some embodiments, isolation of the biologically controlled measurand is used to image and/or quantify blood oxygen-level dependent (BOLD) contrast in the brain, spinal cord, other body organs, and/or tumor.

In some embodiments, isolation of the biologically controlled measurand is used to segment tissue for diagnosis of cancer and immune disorders.

In some embodiments, isolation of the biologically controlled measurand is used to image and/or quantify water diffusion and/or diffusion of dissociated drugs.

In some embodiments, the biologically controlled measurand comprises highly metabolic areas in living systems surrogated by mitochondrial membranes pooled in small compartments.

In some embodiments, the biologically controlled measurand comprises deoxygenated blood in concussed tissue.

In some embodiments, isolation of the biologically controlled measurand is used to image and/or quantify cancerous tissue dispersion.

In some embodiments, the biologically controlled measurand comprises metabolic and/or structural surrogates of neuronal function or other biological functions.

In some embodiments, the biologically controlled measurand is confined fluids in a living system.

In some embodiments, isolation of the biologically controlled measurand is used to image and/or quantify dispersion and/or accumulation of drugs in the physiological system.

In some embodiments, the non-invasive imaging system comprises a magnetic resonance system.

In some embodiments, the non-invasive imaging system is selected from the group consisting of, and not limited to, ultrasound, computed tomography, PET, laser, optical tomography and fiber optical imaging, photoacoustic, reflection of visible, NIR, UV light, X-rays or Gamma-rays, and electroencephalogram (EEG).

In another aspect, a system (e.g., analysis system) is disclosed comprising one or more processors; and a memory having instructions stored thereon, wherein execution of the instructions by the one or more processors cause the one or more processors to perform the method of any one of above-recited steps.

In another aspect, a non-transitory computer readable medium is disclosed having instructions stored thereon, wherein execution of the instructions by a processor cause the one or more processors to perform the method of any one of above-recited steps.

In another aspect, a medical or biomedical imaging system is disclosed (i.e. ultrasound, focused ultrasound (FUS), computed tomography, PET, laser, optical tomography and fiber optical imaging, photoacoustic, reflection of visible, NIR or UV light or X-rays or Gamma-rays), the system having memory with instructions stored thereon, wherein execution of the instructions by one or more processors of the system cause the one or more processors to perform the method of any one of above-recited steps.

In another aspect, a head or body radiofrequency (RF) coil apparatus of a magnetic resonance system, the apparatus having coil elements designed or optimized based on myelin-specific information acquired in the method of any one of above method or system.

BRIEF DESCRIPTION OF DRAWINGS

The patent or application file contains at least one drawing executed in color. Copies of this patent or patent application publication with color drawing(s) will be provided by the Office upon request and payment of the necessary fee.

The color drawings are necessary as the only practical medium by which aspects of the claimed subject matter may be accurately conveyed. For example, the claimed invention relates to medical imaging technology. Color drawings of the output of the medical imaging system and methodologies and corresponding experimental results may be necessary to illustrate features of the claims.

Figure 1:
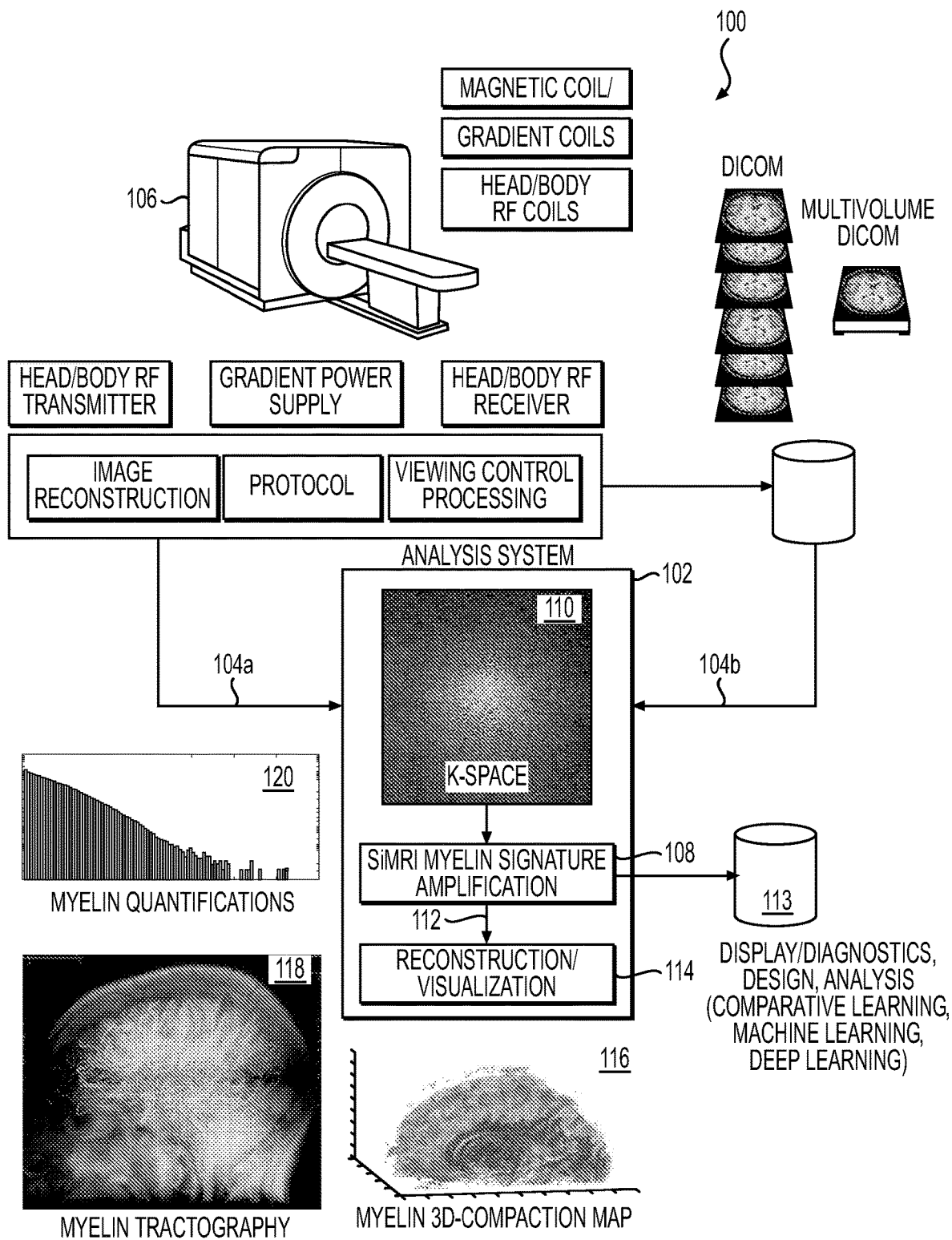

Embodiments of the present invention may be better understood from the following detailed description when read in conjunction with the accompanying drawings. Such embodiments, which are for illustrative purposes only, depict novel and non-obvious aspects of the invention. The drawings include the following figures:

FIG. 1 is a diagram of a myelin-signal isolated magnetic resonance system (siMRI) configured for in-vivo imaging of myelin and its associated structure, in accordance with an illustrative embodiment.

Figure 2:
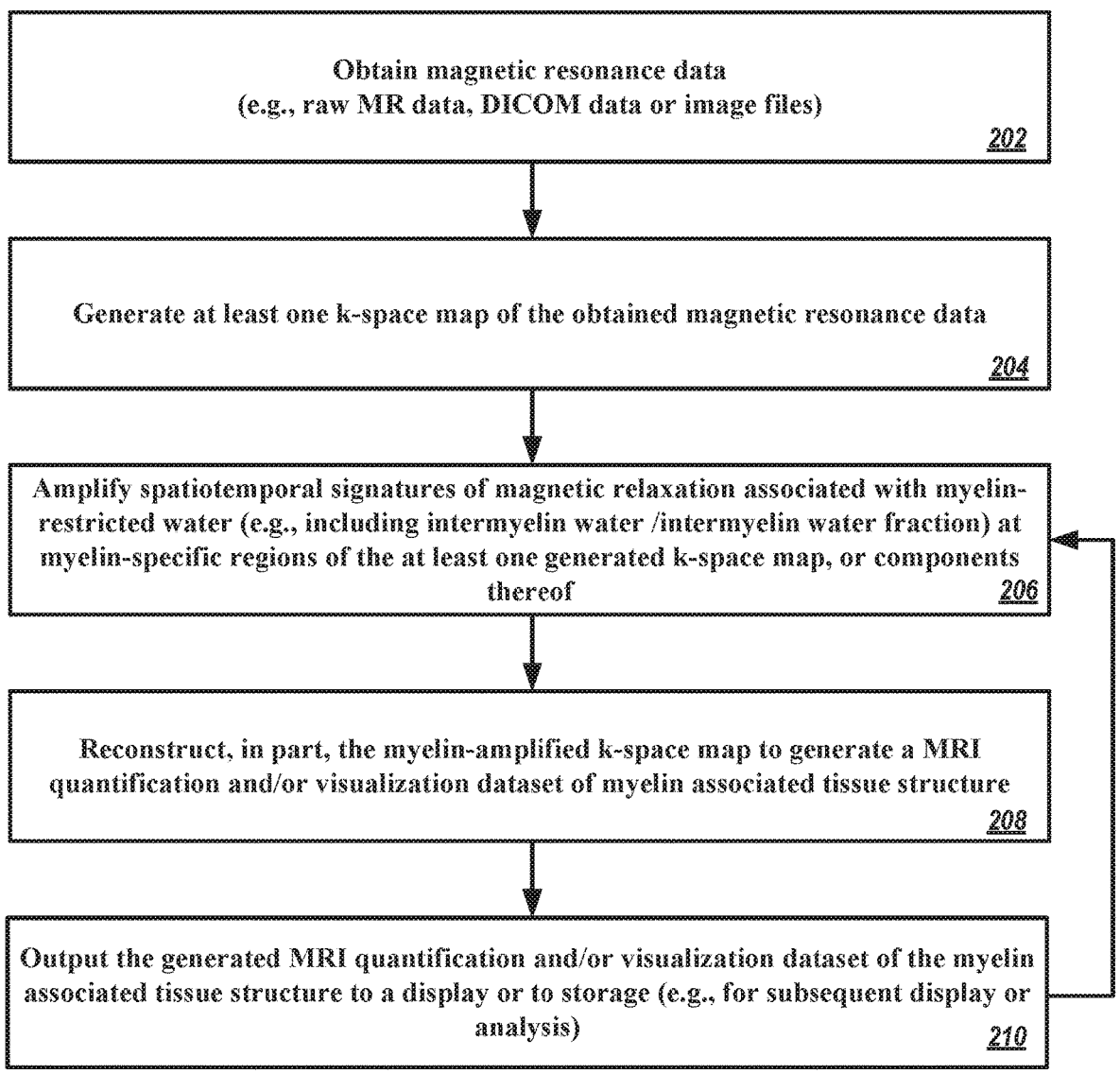

FIG. 2 is a flow diagram of a method of operating a myelin-signal isolated Magnetic Resonance System for in-vivo imaging of myelin and its associated structure, in accordance with an illustrative embodiment.

FIG. 3 is a diagram of a myelin compaction heat map generated by the myelin-signal isolated Magnetic Resonance System of FIG. 1, in accordance with an illustrative embodiment.

Figure 4:

FIG. 4 is a computer-generated three-dimensional (3D) visualization of a myelin compaction heat map dataset generated from results outputted by the myelin-signal isolated Magnetic Resonance System of FIG. 1, in accordance with an illustrative embodiment.

Figure 5:
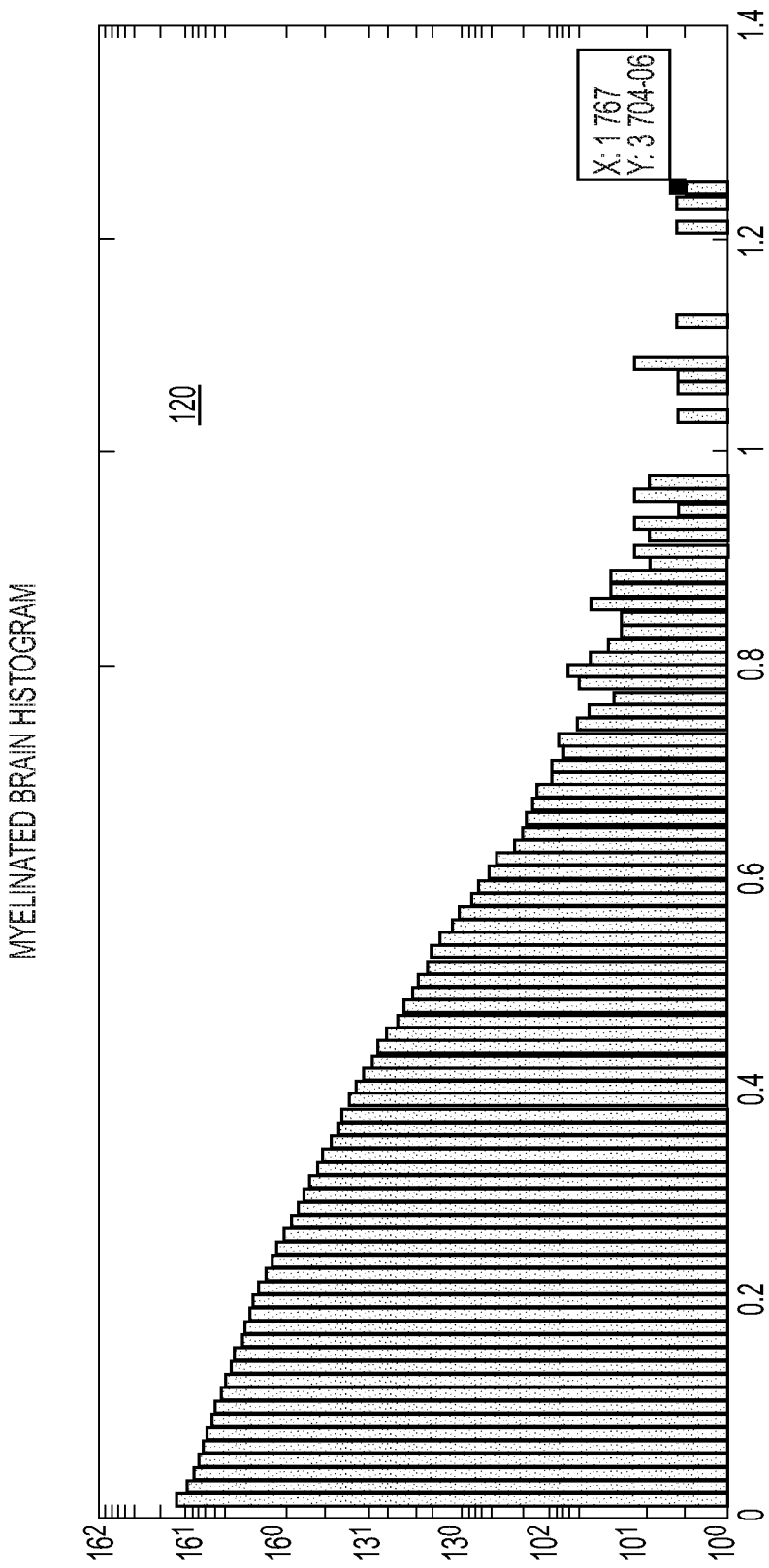

FIG. 5 is a diagram of a myelin volume histogram of a quantification dataset showing distribution of myelin volume generated from results outputted by the myelin-signal isolated Magnetic Resonance System of FIG. 1, in accordance with an illustrative embodiment.

Figure 6:
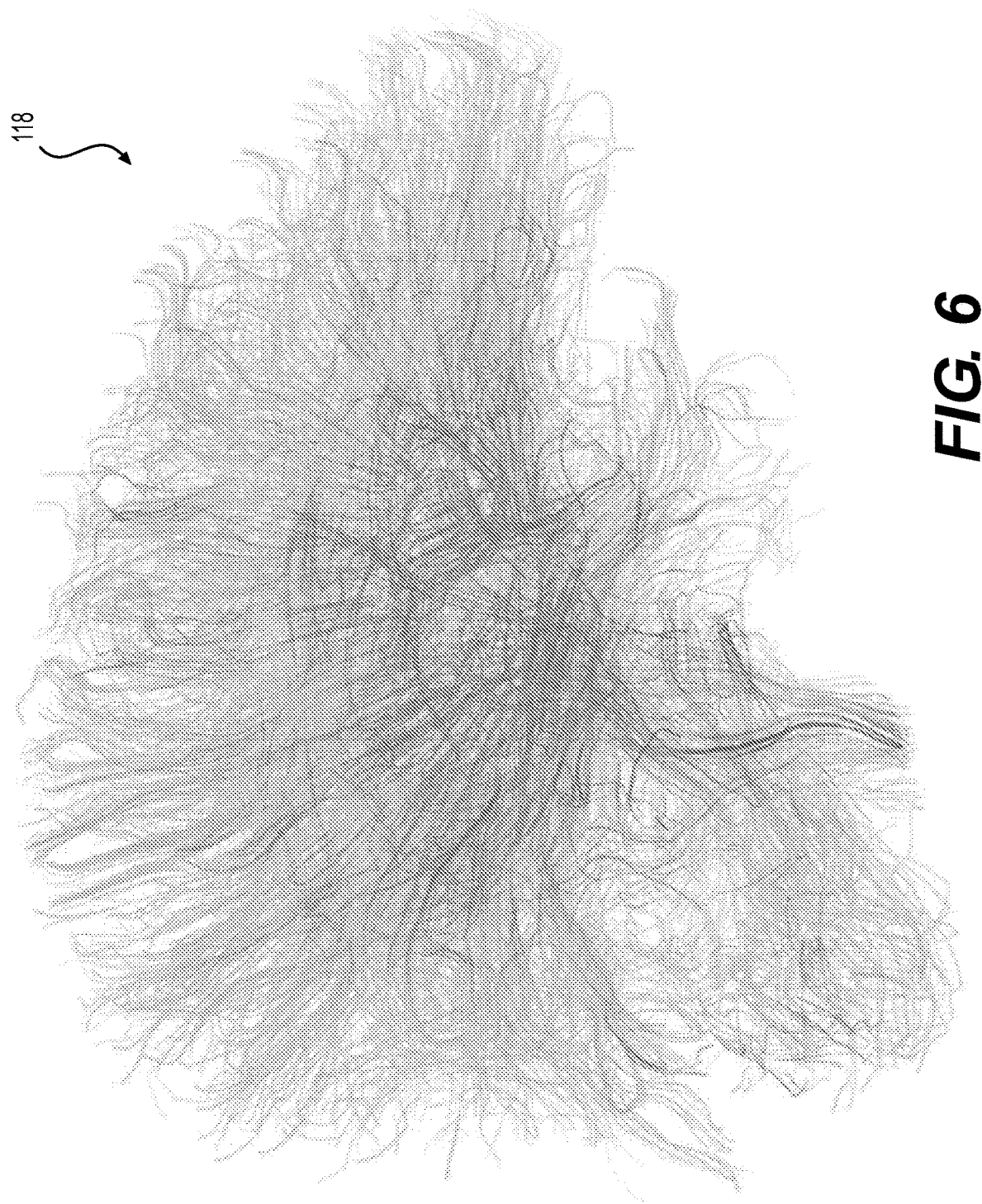

FIG. 6 is another computer-generated tractography of isolated myelin of results outputted by the myelin-signal isolated Magnetic Resonance System of FIG. 1, in accordance with an illustrative embodiment.

Figure 7:
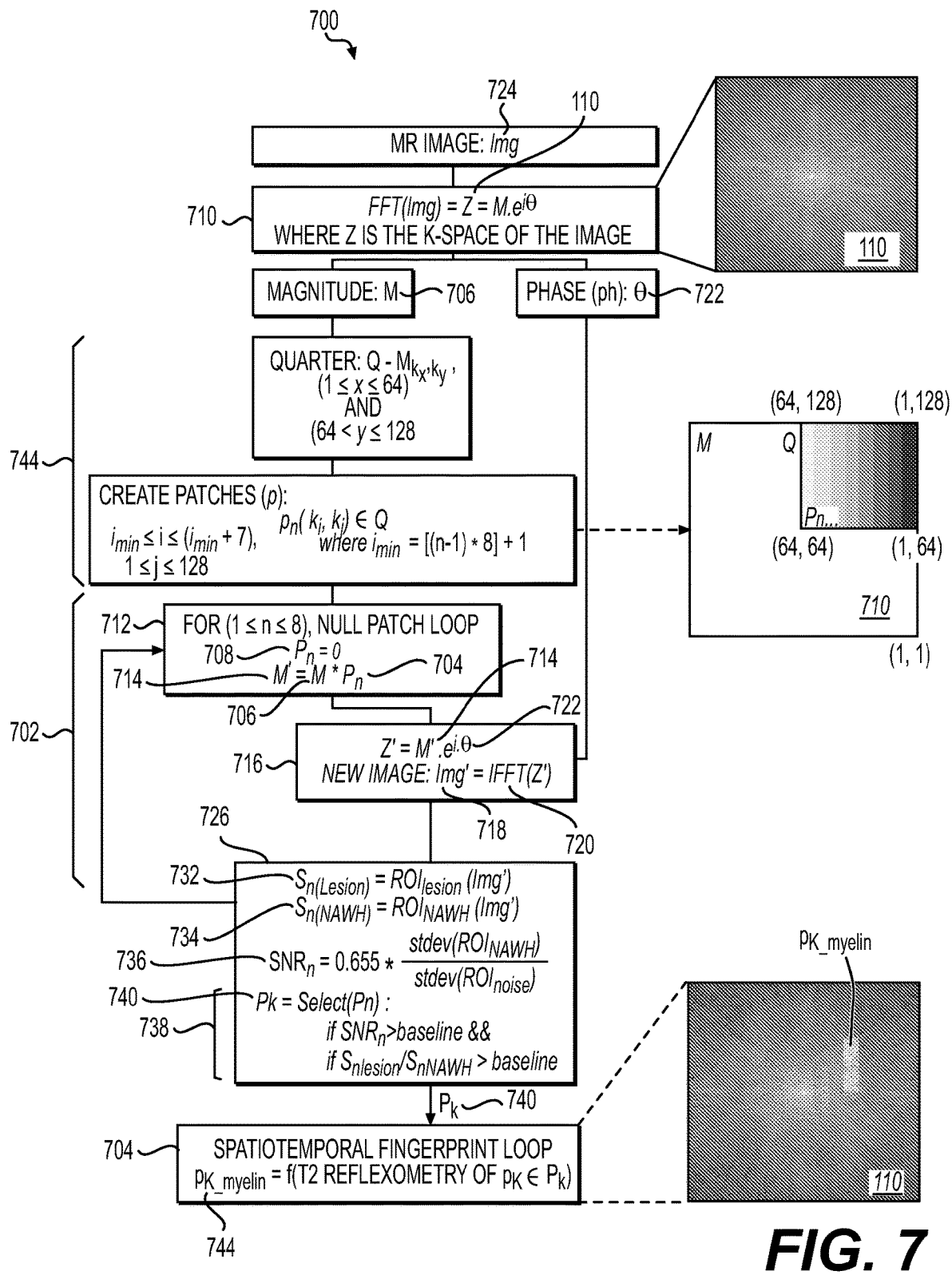

FIG. 7 is a flow diagram of a method of isolating spatiotemporal signatures of myelin-restricted water in myelin-specific regions of a k-space map, or components thereof, in accordance with an illustrative embodiment.

Figure 8:
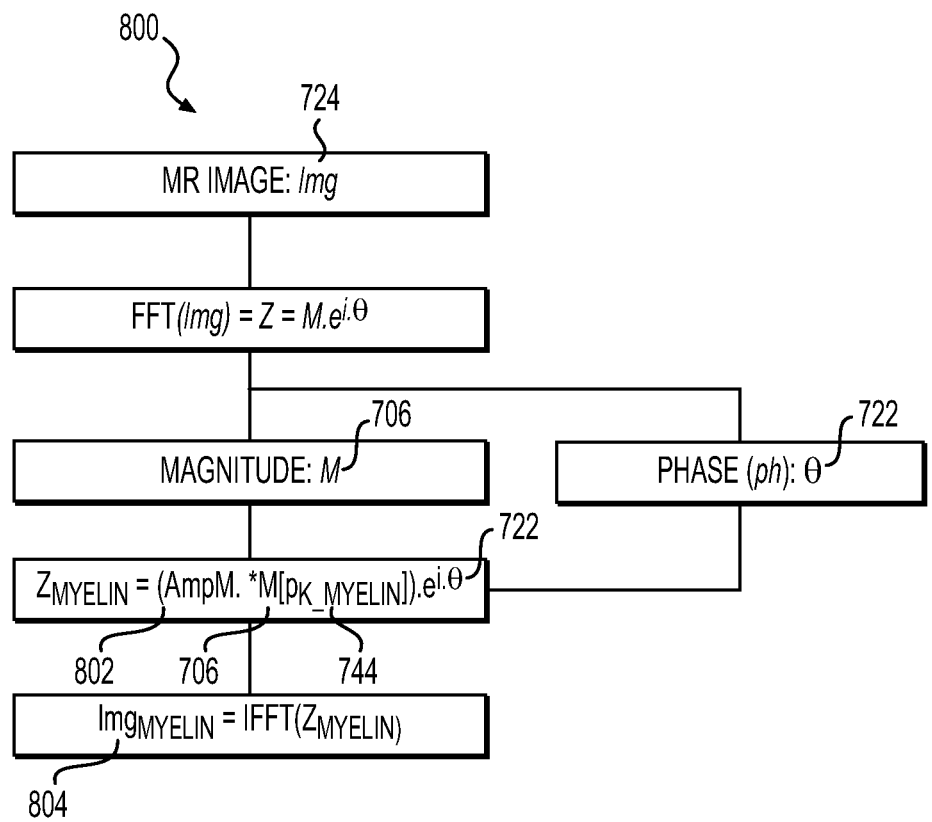

FIG. 8 is a flow diagram of a Myelin signal-amplification loop for generating a myelin compaction image, in accordance with an illustrative embodiment.

Figure 9:
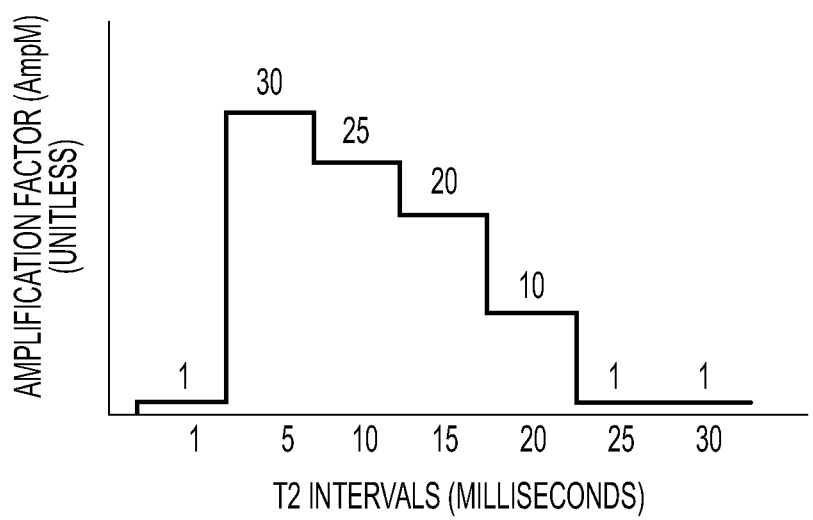

FIG. 9 is a diagram of an exemplary myelin amplification factors (MAFs), in accordance with an illustrative embodiment.

Figure 10:
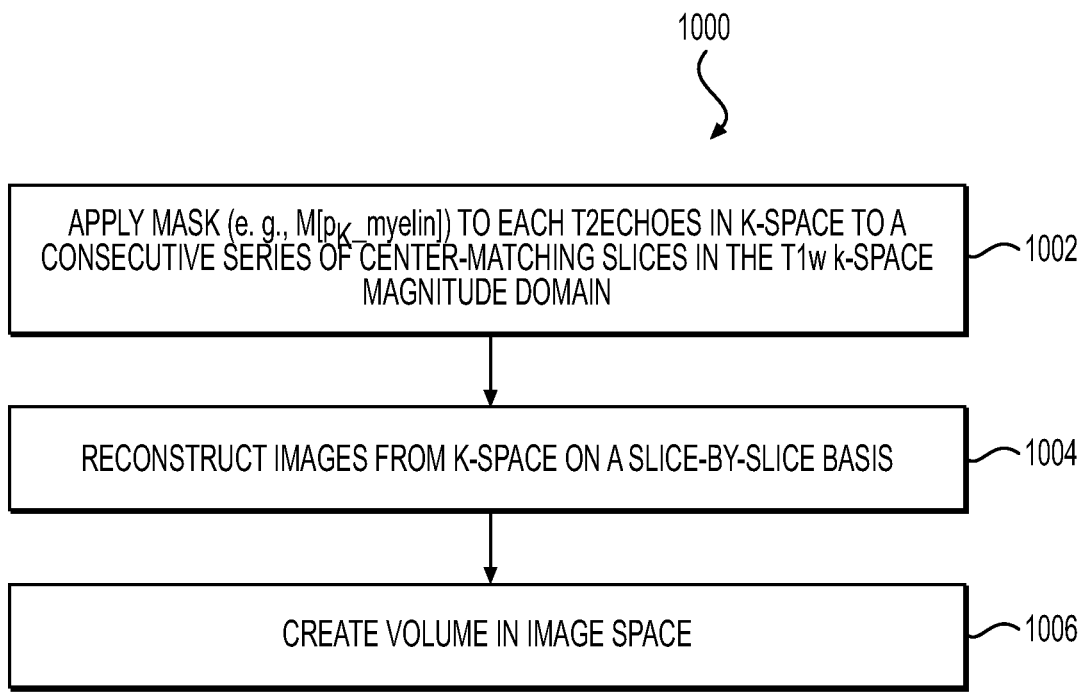

FIG. 10 is a flow diagram of a method to generate the 3D myelin siMRI compaction map of FIG. 4, in accordance with an illustrative embodiment.

Figure 11:
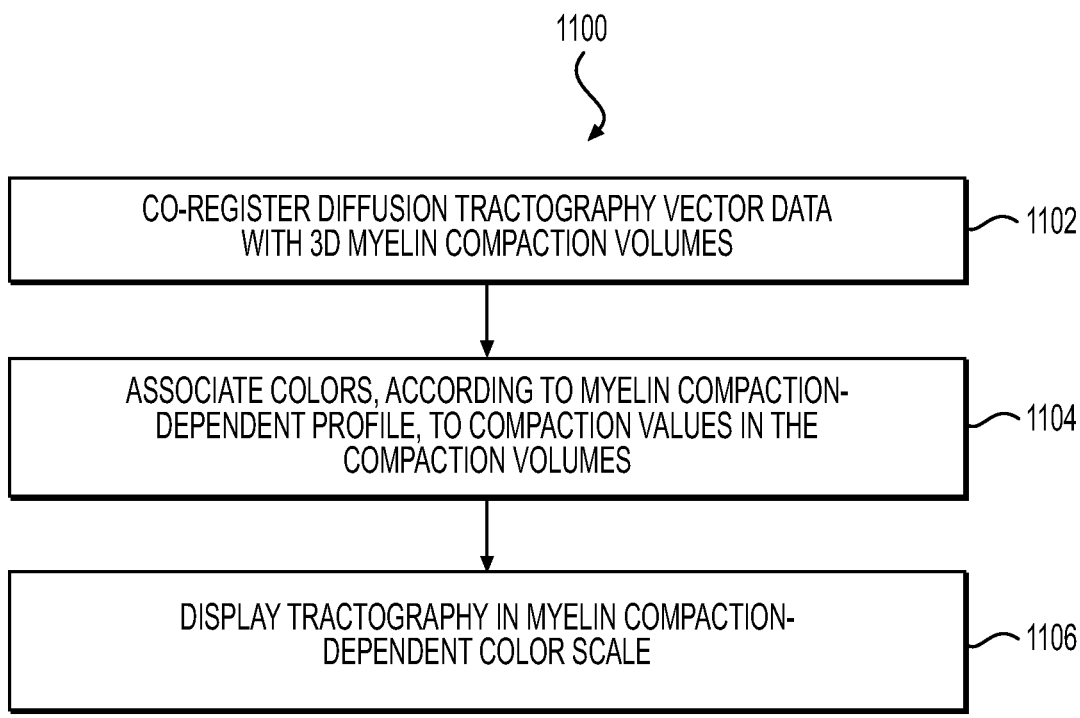

FIG. 11 is a diagram to generate a fiber tractography image based on the generated MRI quantification and/or visualization dataset of the myelin associated tissue structure, in accordance with an illustrative embodiment.

Figure 12:
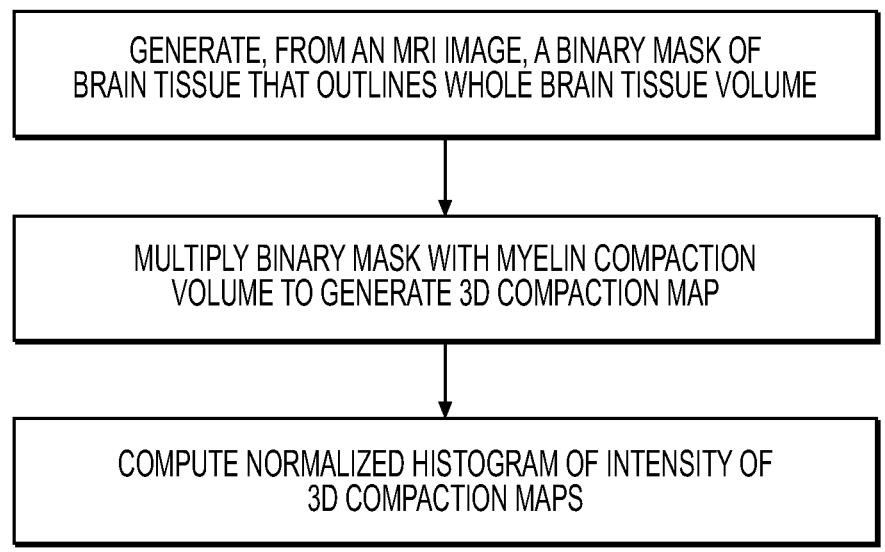

FIG. 12 is a diagram of a method to generate myelin-volume histograms in accordance with an illustrative embodiment.

Figure 13:
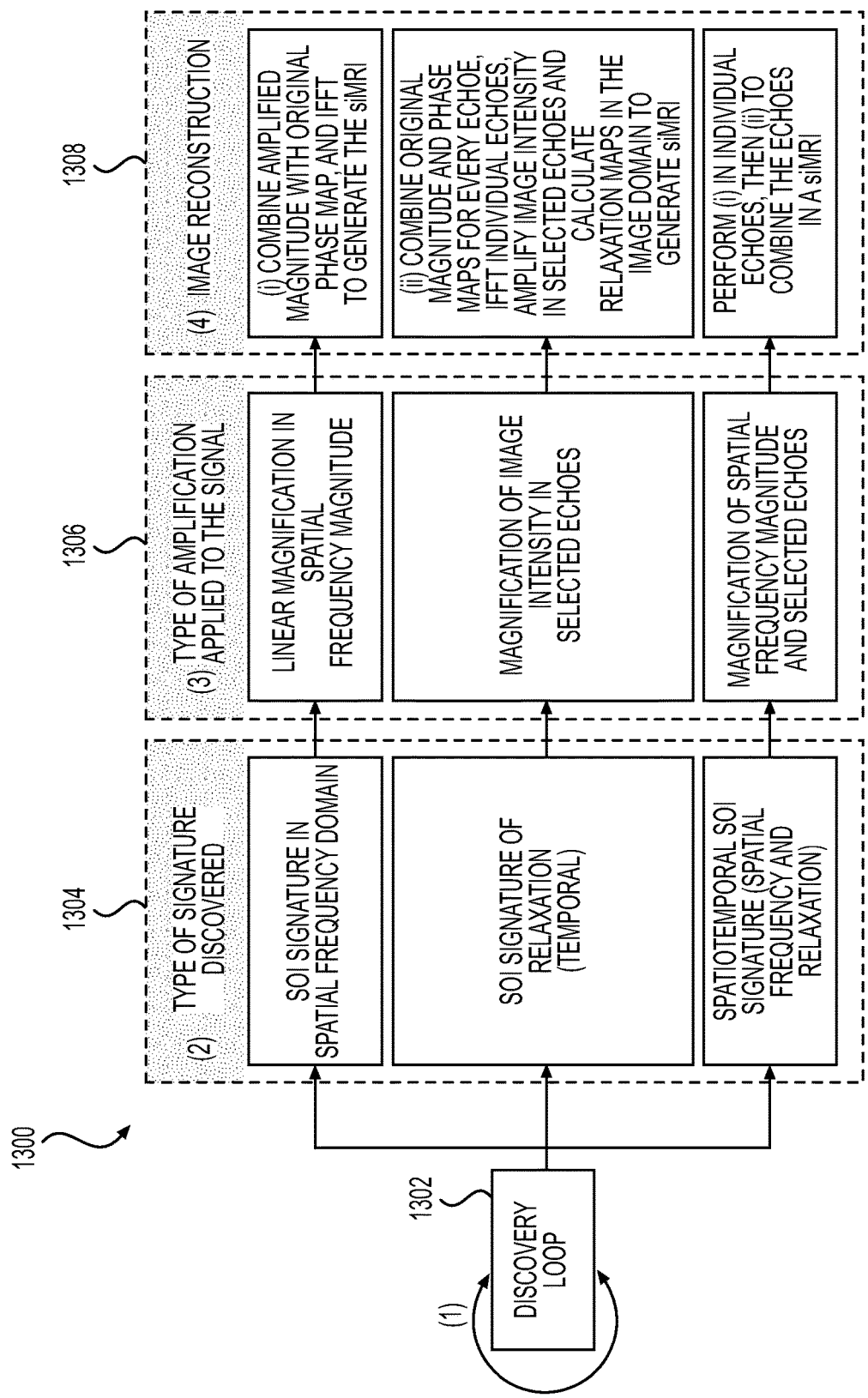

FIG. 13 is a diagram of a method of performing siMRI, in accordance with an illustrative embodiment.

Figure 14:
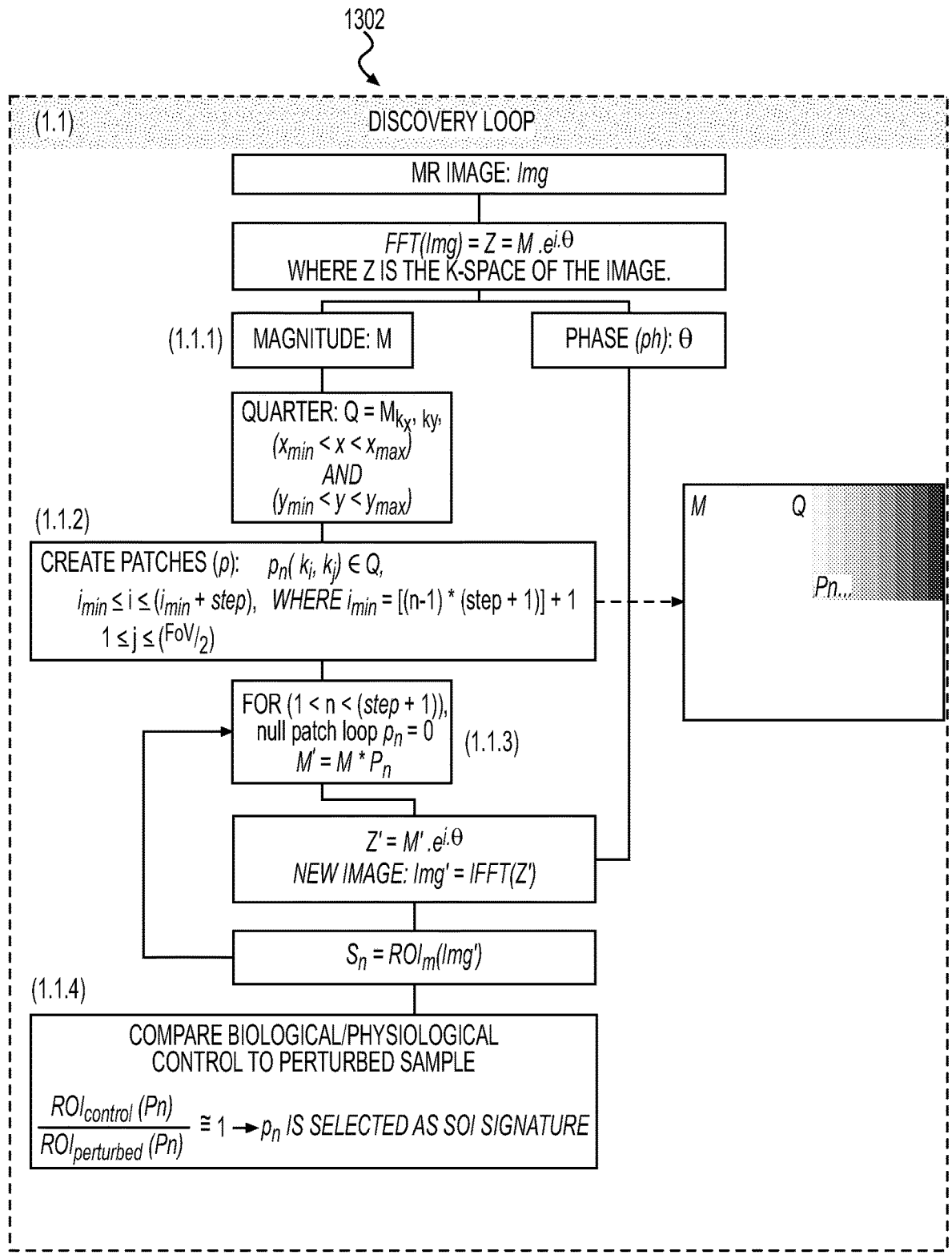

FIG. 14 is a diagram of the discovery phase method, in accordance with an illustrative embodiment.

FIG. 15A (top and bottom) show MRI T1w images regions-of-interest associated with myelin-restricted water used as learning ROIs, in accordance with an illustrative embodiment.

Figure 15B:
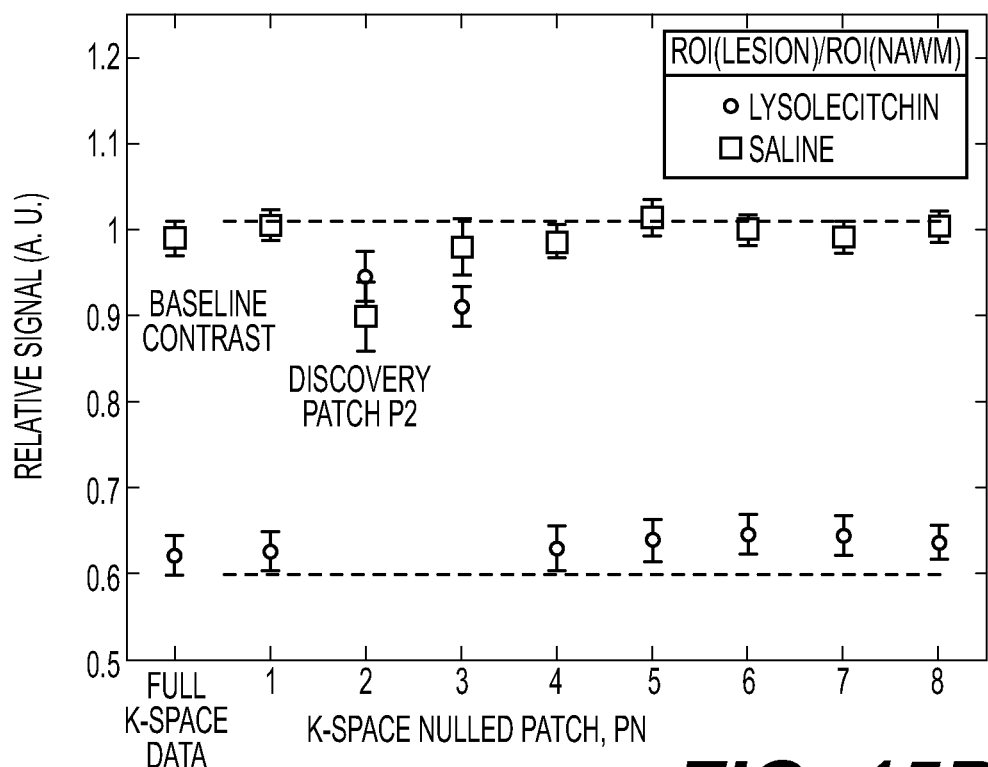
Figure 15C:
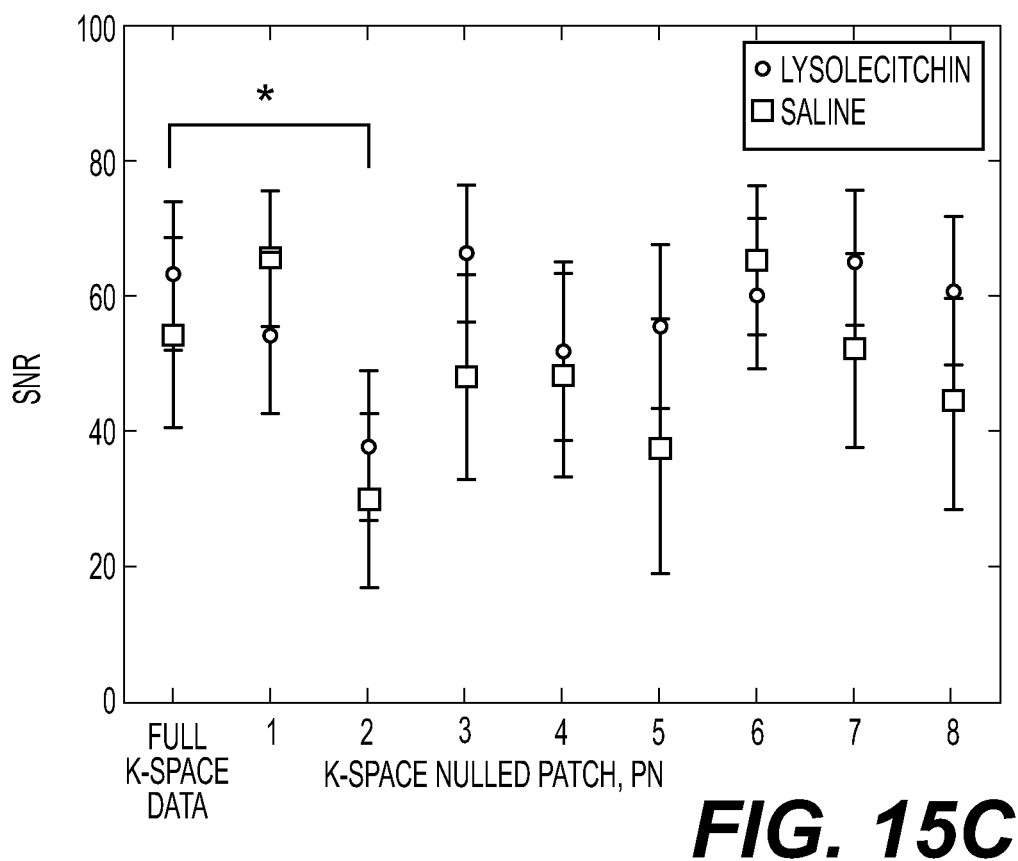

FIGS. 15B and 15C show biologically-derived signal that inputs the 'Myelin siMRI Discovery Loop' illustrated in FIG. 14, in accordance with an illustrative embodiment.

FIGS. 16A, 16B, 16C, 16D, 16E, 16F, 16G, 16H, 16I, and 16K show various aspects of a cross-species validation study conducted to validate the discovery patch, in accordance with an illustrative embodiment.

Figures 17A, 17B:
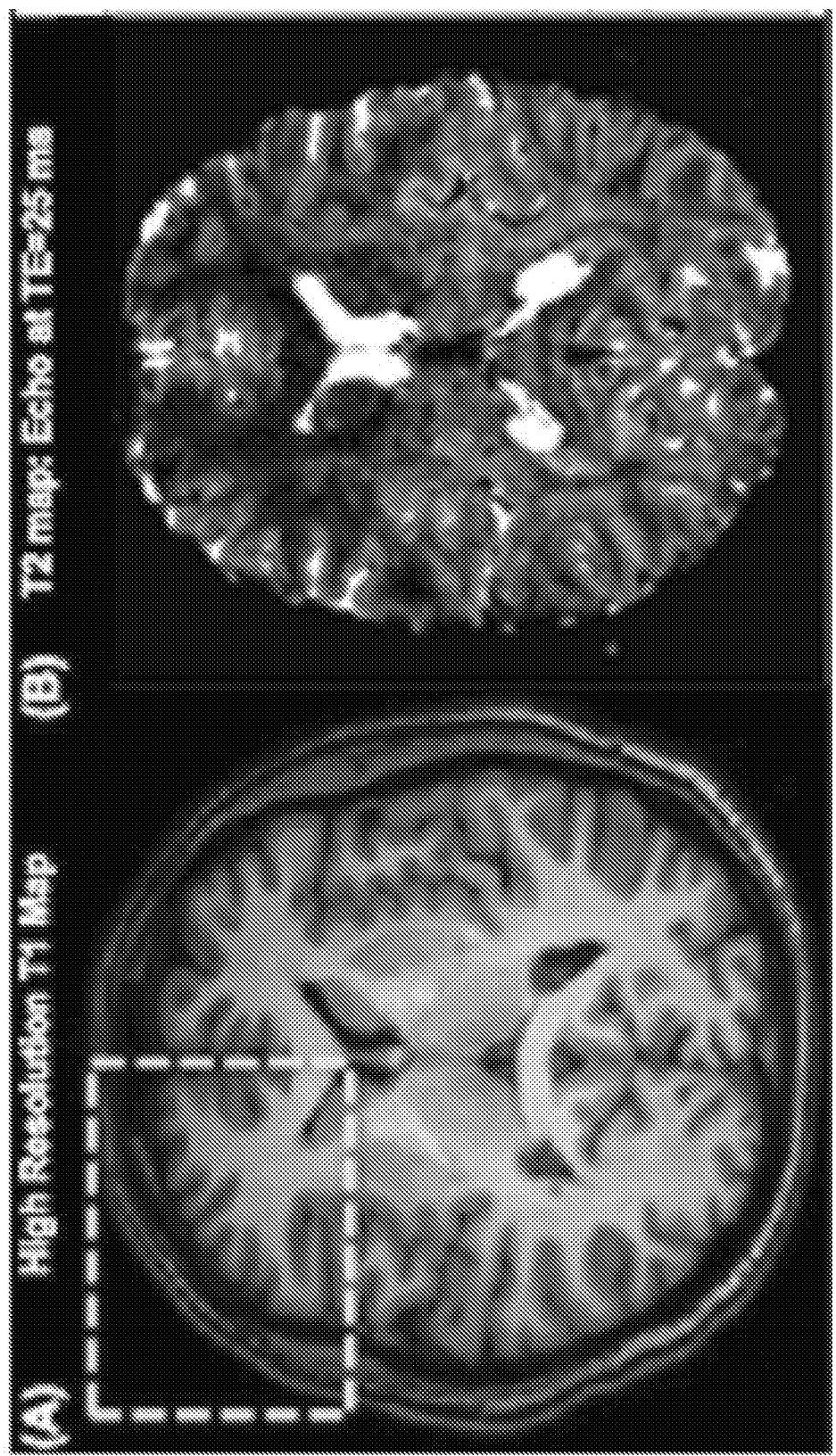

FIGS. 17A and 17B show matching planes of one T1-weighted map and a T2* single echo image of a subject to which spatiotemporal fingerprint and the myelin signal-amplification loops are applied in an aging study, in accordance with an illustrative embodiment.

Figure 18:
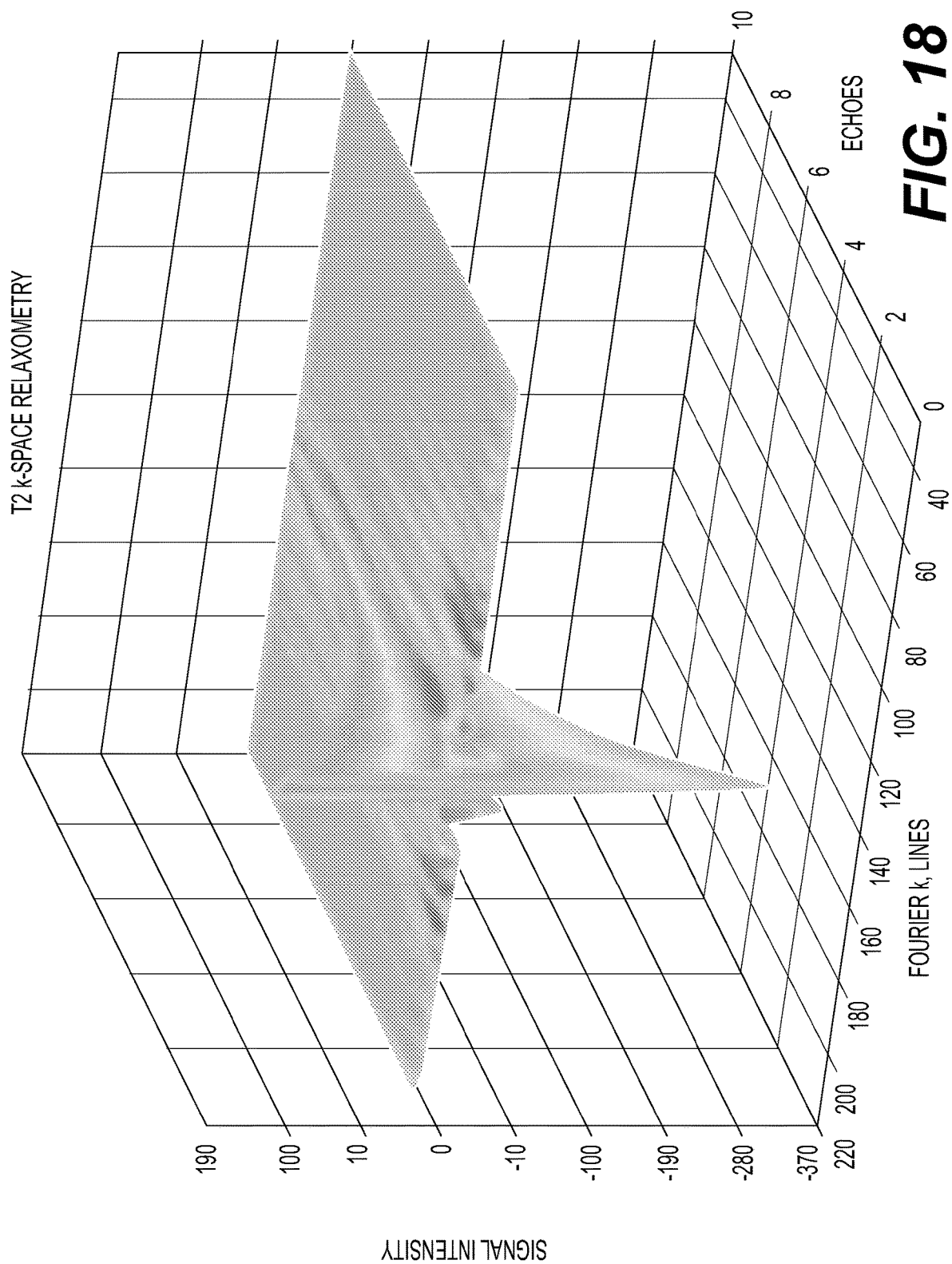

FIG. 18 shows relaxation data of individual spatial frequencies in k-space points over time in 3-dimensions used in an aging study.

FIG. 19 is a table of Myelin-specific T2* stratification in individual k-space compartments of the brain for a subject, in accordance with an illustrative embodiment.

Figure 20:
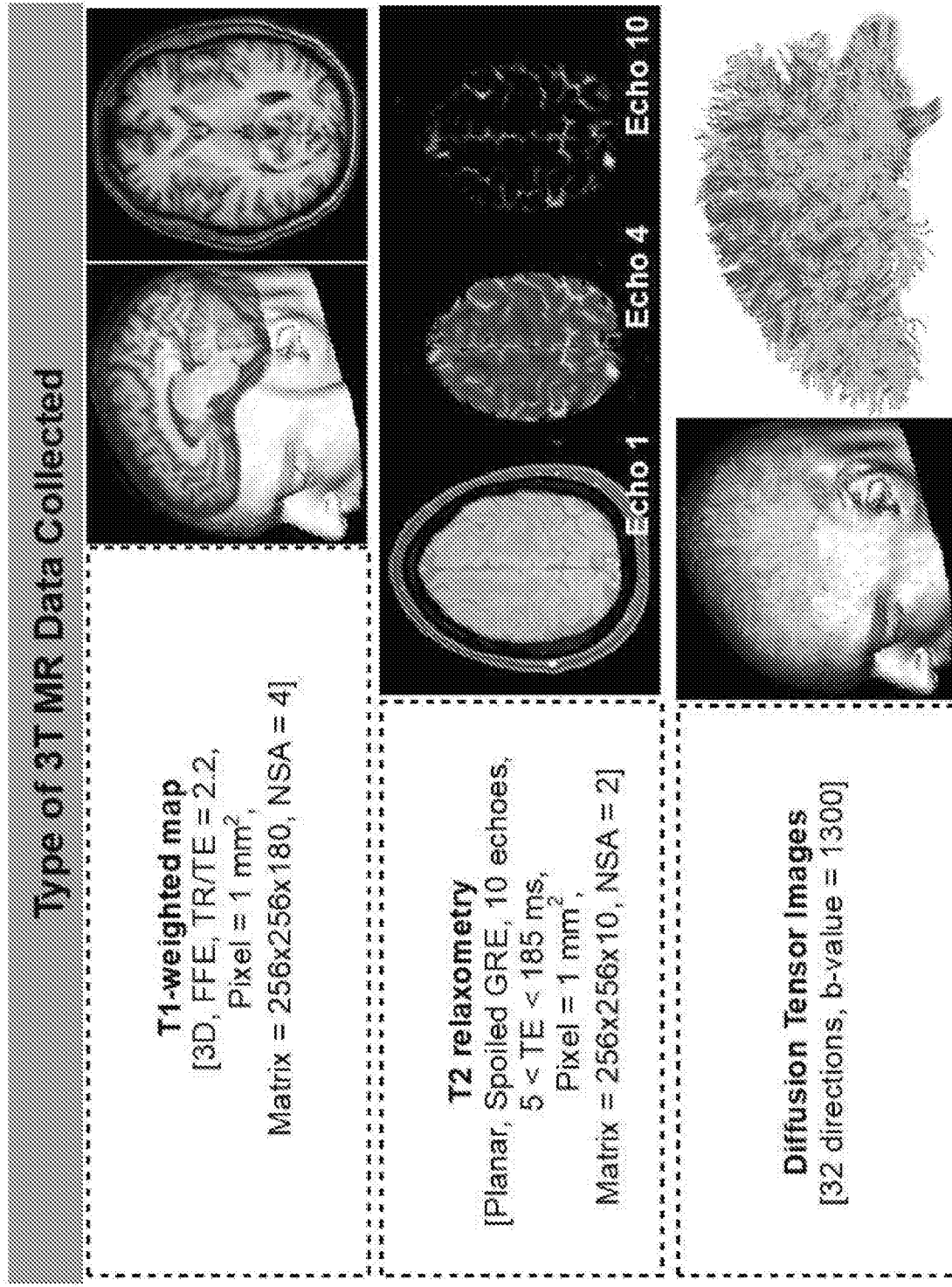

FIG. 20 shows description of magnetic resonance sequences and illustration of images acquired in a 3T Philips Ingenia scanner, in accordance with an illustrative embodiment.

FIG. 21 shows 3D views of the same and shows the leveraged information of the brain myeloarchitecture obtained by siMRI, in accordance with an illustrative embodiment.

Figure 22:
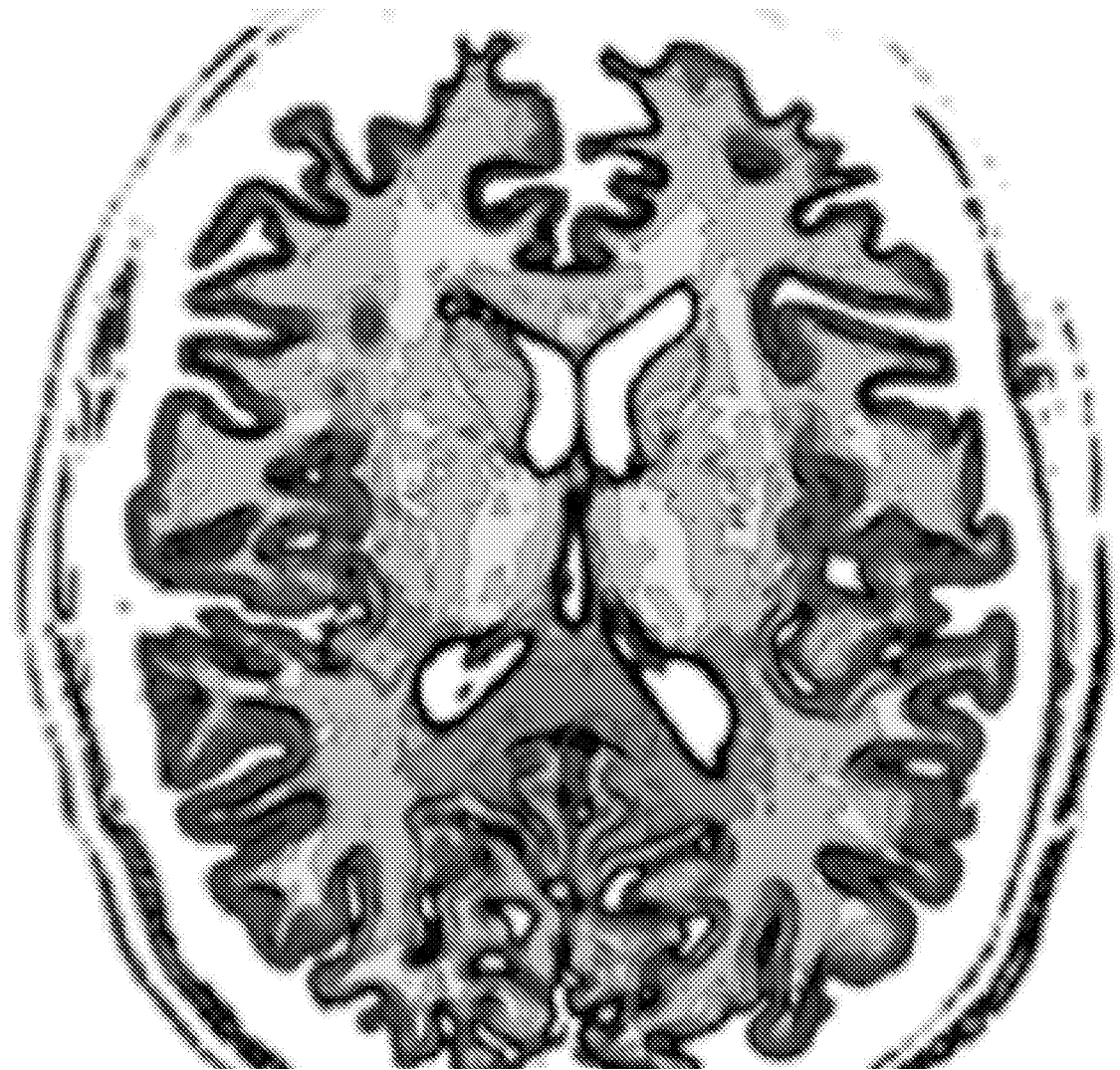

FIG. 22 shows a myelin compaction map of the myelin compaction data, in accordance with an illustrative embodiment.

FIGS. 23A, 23B, 23C, and 23D show generated myelin-related quantitative data, in accordance with an illustrative embodiment.

Figure 24A:
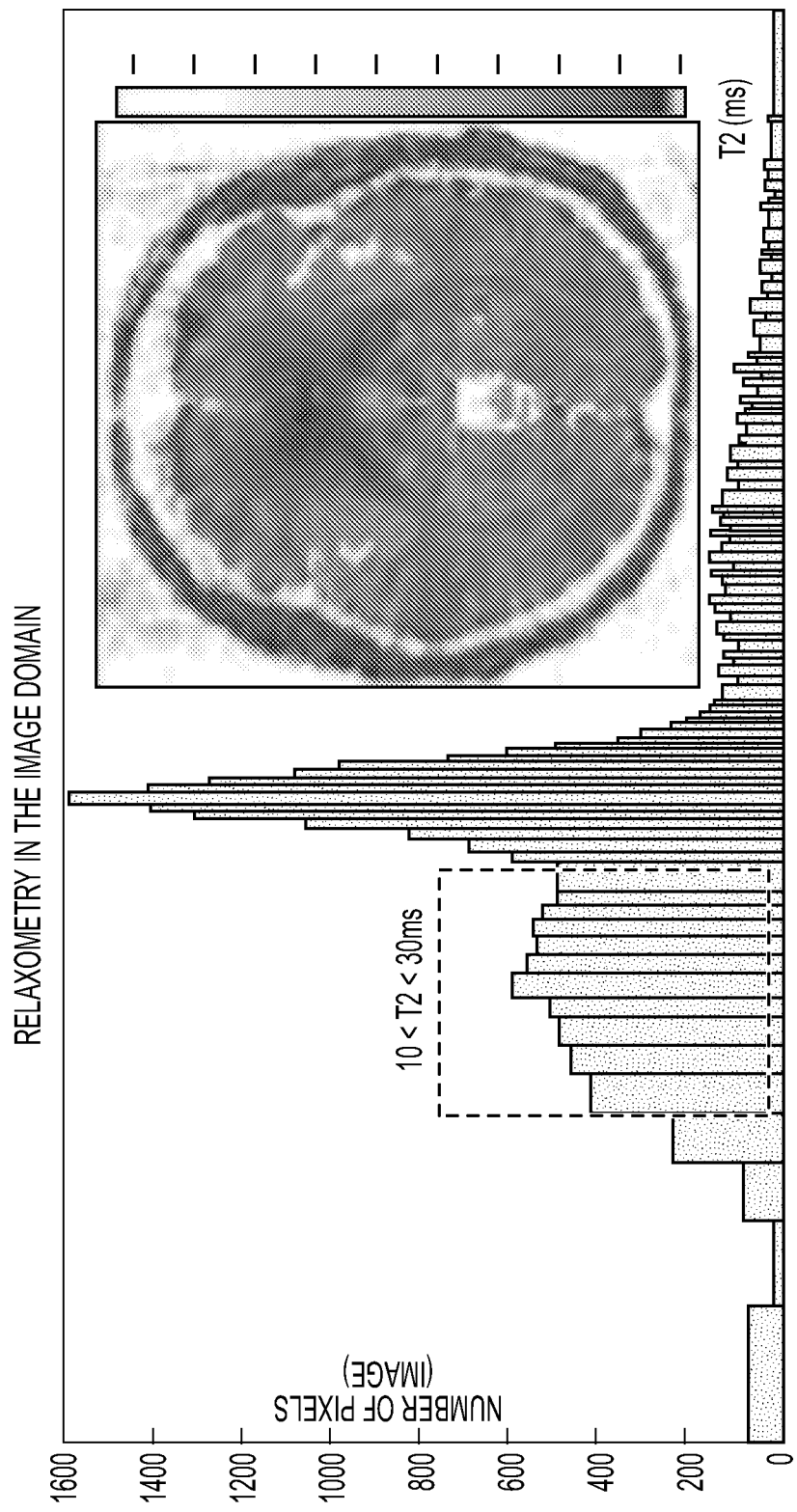
Figure 24B:
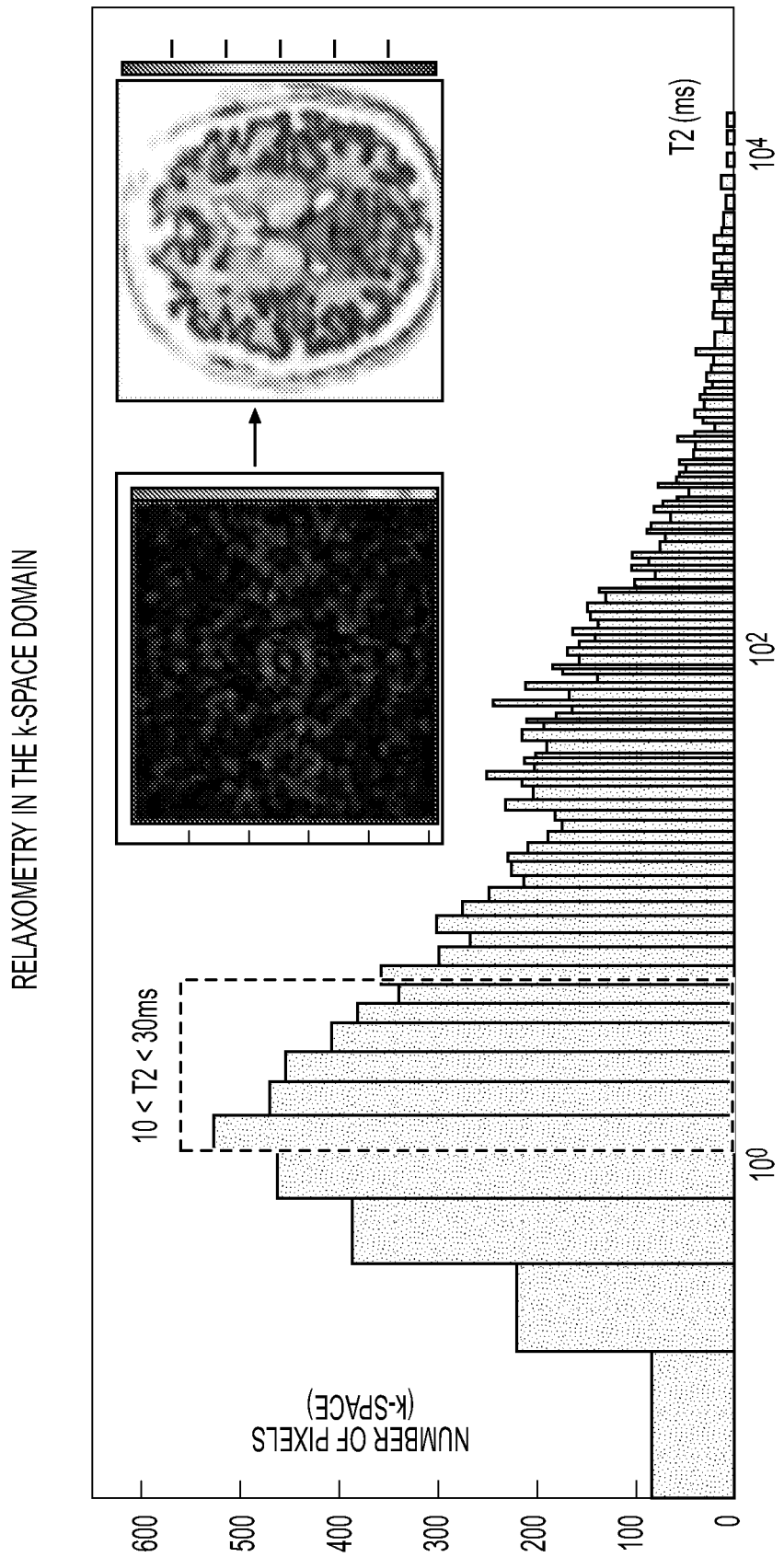

FIGS. 24A and 24B show relaxometry data in the image domain and in the magnitude of the k-space domain, and myelin maps generated from both, in accordance with an illustrative embodiment.

FIG. 25A shows a series of sequential brain slices of T1 contrast acquired from the brain of a normal control subject.

FIG. 25B shows isocontours within corresponding myelin maps calculated from siMRI, in accordance with an illustrative embodiment.

FIG. 25C shows diffusion-based tractography (DTI) colored by the siMRI myelin compaction indices, in accordance with an illustrative embodiment. Remarkable anatomical continuity in fiber traces, matching known fiber tracts, is shown both coronal and sagittal.

FIGS. 26A, 26B, 26C, 26D, 26E, 26F, 26G, 26H, 26I, 26J, 26K, 26L, 26M, and 26N show signatures of k-space relaxation that correlate to aging across a small population of normal control brains, in accordance with an illustrative embodiment.

Figure 27:
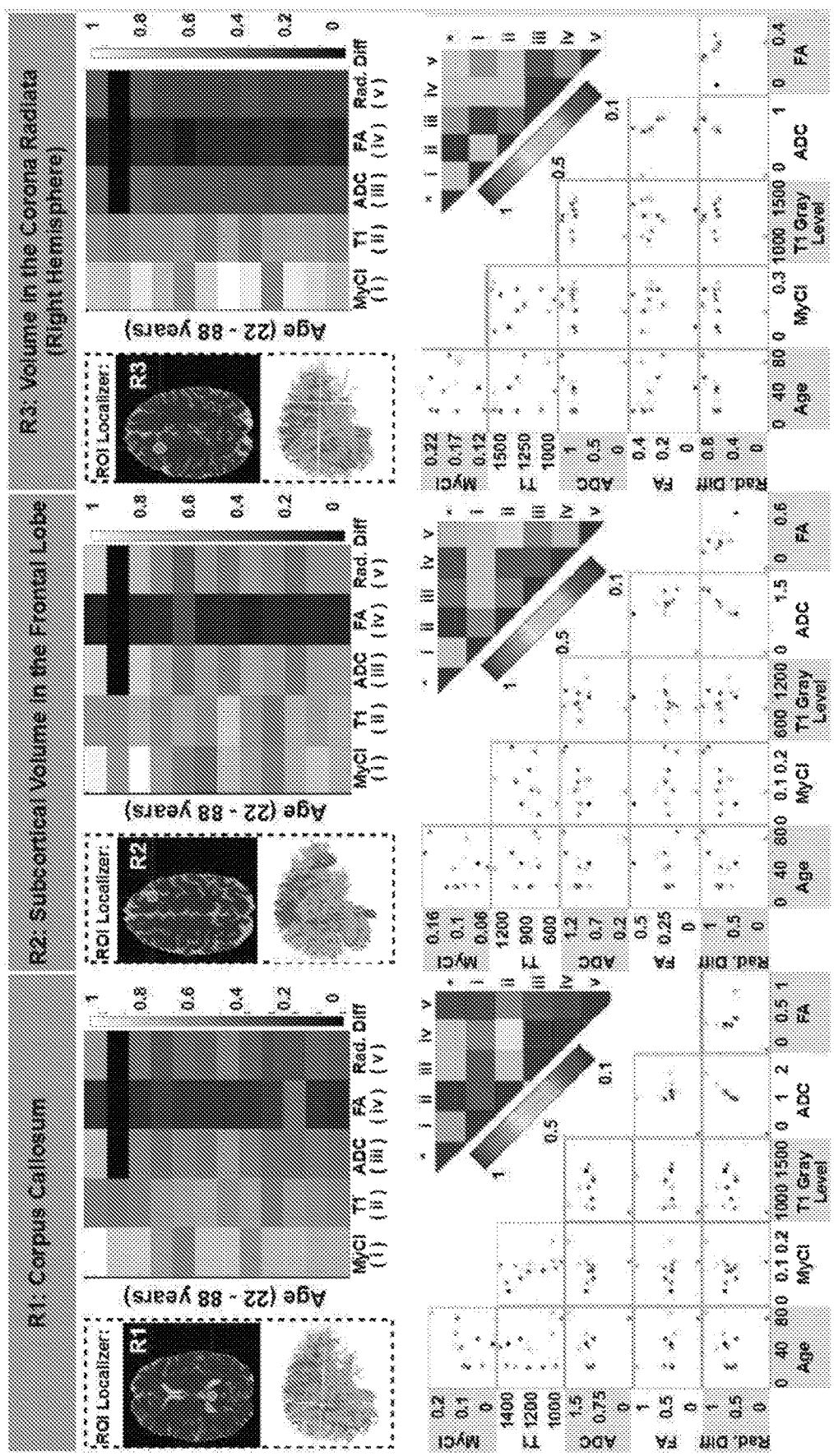

FIG. 27 shows detailed statistical analysis to determine if the quantitative loss of myelin compaction in aging by siMRI analysis was comparably less or more sensitive to established MRI methods, in accordance with an illustrative embodiment.

Figure 28:
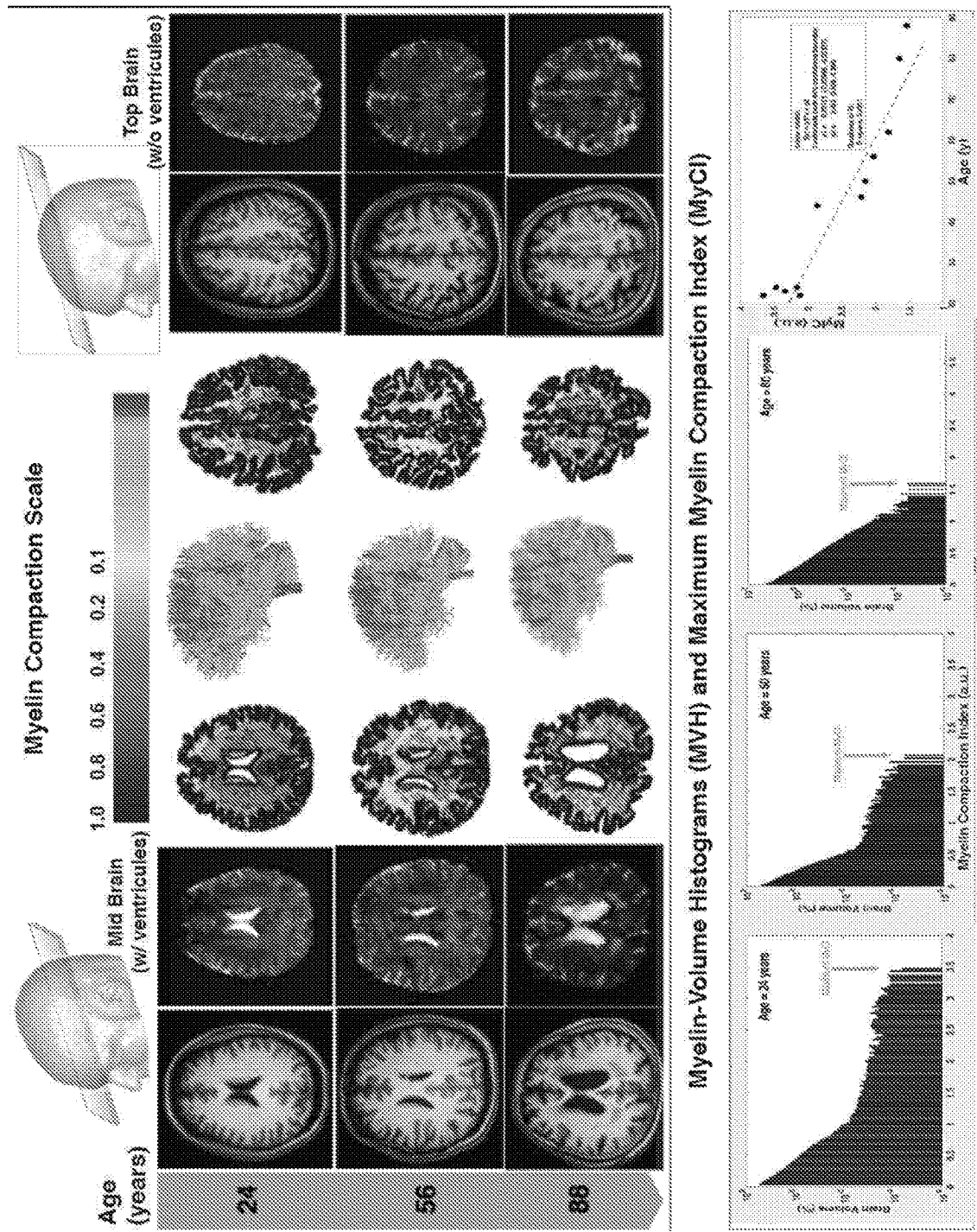

FIG. 28 shows relative myelin compaction maps obtained from siMRIs illustrating detailed image information of brain aging, in accordance with an illustrative embodiment.

Figure 29:
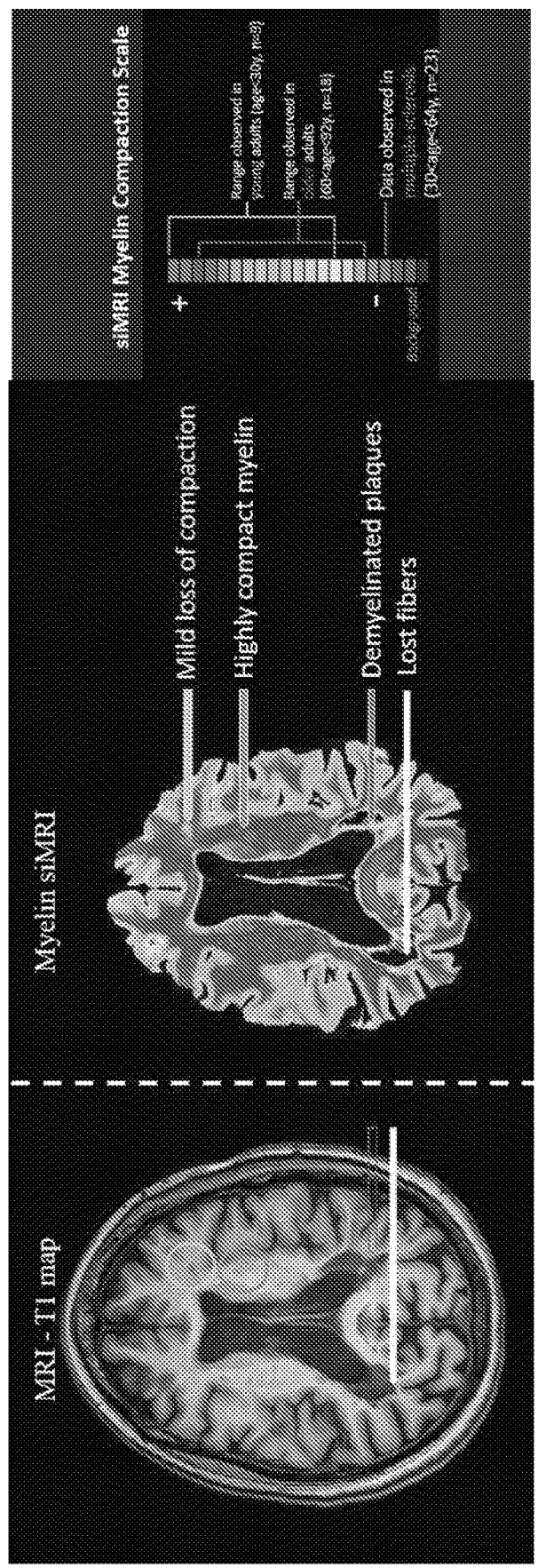

FIG. 29 shows advantage of myelin siMRI in the MS context, in accordance with an illustrative embodiment.

Figure 30:
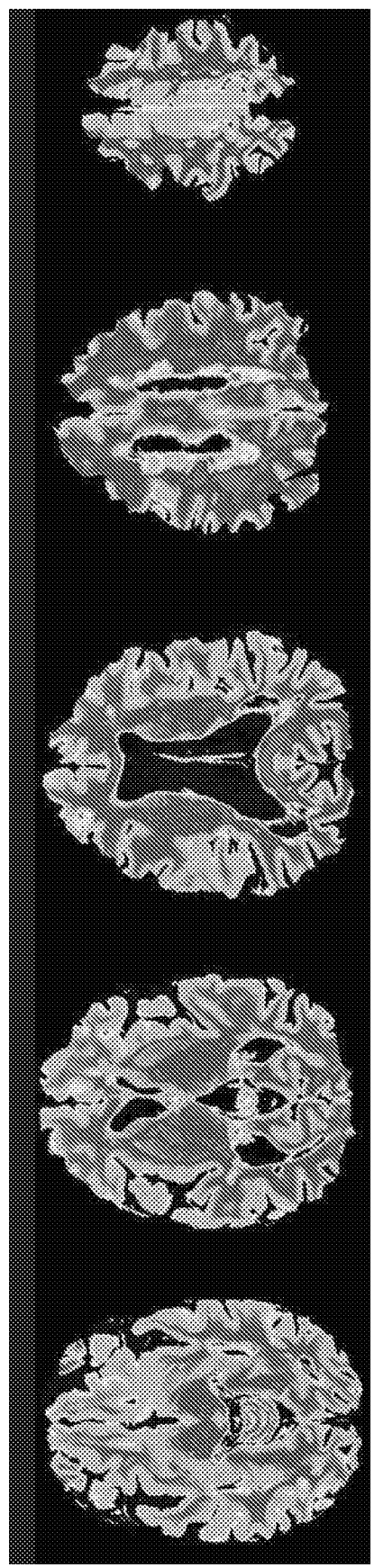

FIG. 30 show a longitudinal sequence of the whole brain amplified with myelin siMRI in accordance with an illustrative embodiment.

Figure 31:
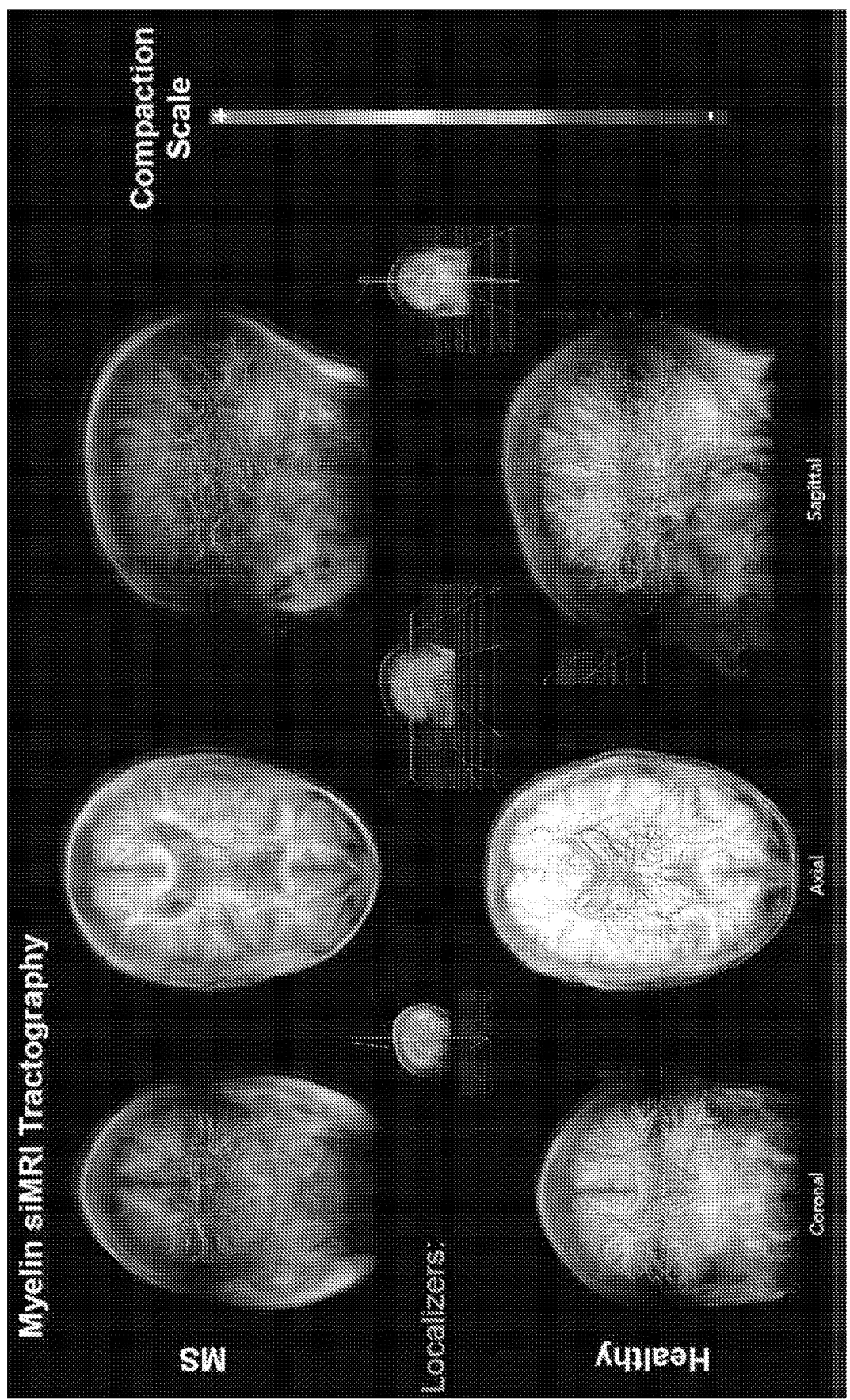

FIG. 31 shows a comparison between Myelin siMRI tractography for multiple-sclerosis and age matched healthy subjects, in accordance with an illustrative embodiment.

Figure 32:
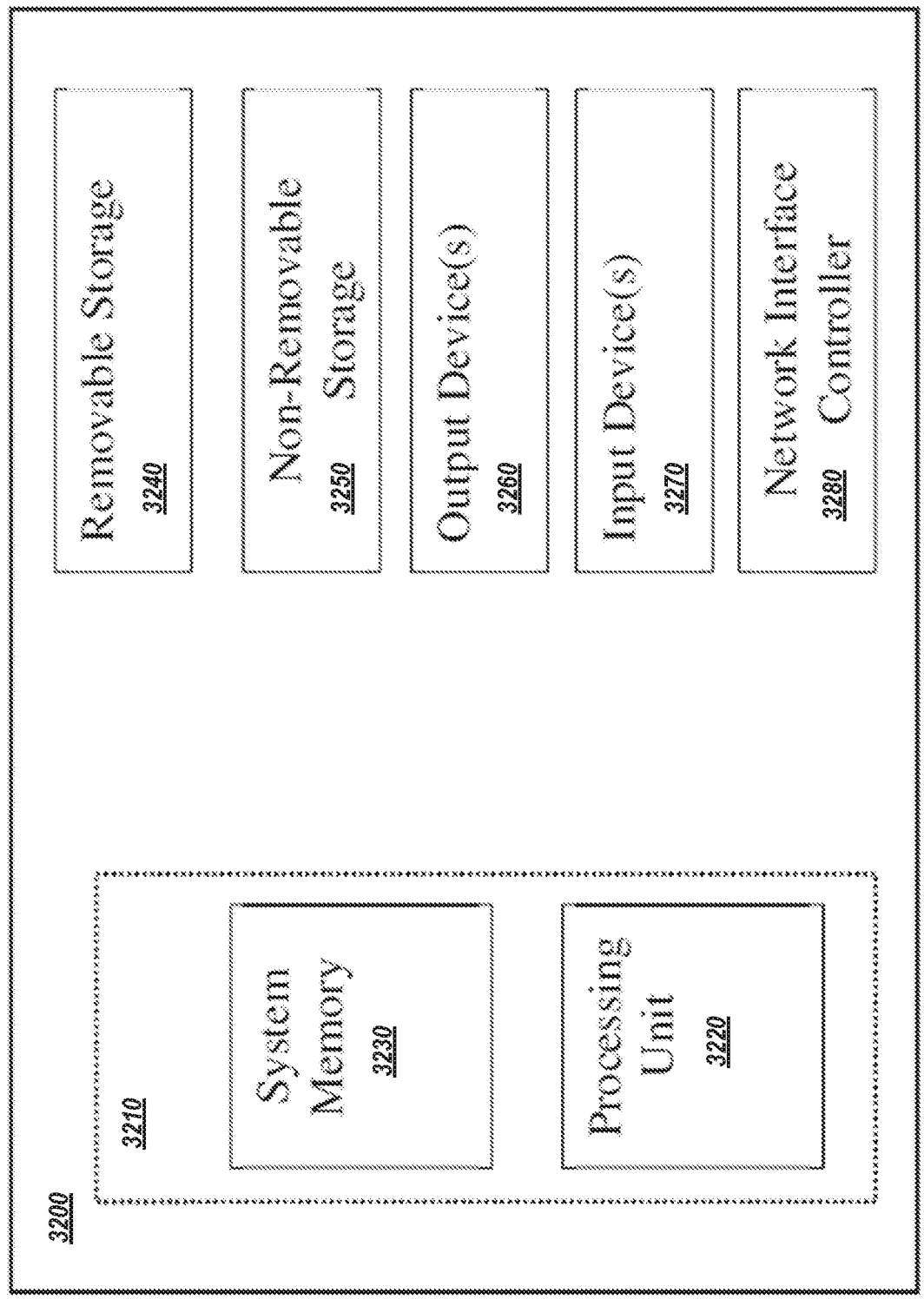

FIG. 32 is a diagram of an example computing device upon which embodiments may be implemented, in accordance with an illustrative embodiment.

DETAILED SPECIFICATION

Each and every feature described herein, and each and every combination of two or more of such features, is included within the scope of the present invention provided that the features included in such a combination are not mutually inconsistent.

FIG. 1 is a diagram of a myelin-signal isolated magnetic resonance system 100 (siMRI) configured for in-vivo imaging of myelin and its associated structure, in accordance with an illustrative embodiment. FIG. 2 is a flow diagram of a method 200 of operating a myelin-signal isolated Magnetic Resonance System for in-vivo imaging of myelin and its associated structure, in accordance with an illustrative embodiment. FIG. 2 is described in conjunction with FIG. 1.

As shown in FIG. 1, the system 100 includes an analysis system 102 configured to obtain (step 202) magnetic resonance data 104 (e.g., raw magnetic resonance data shown as 104a from a magnetic resonance imaging system 106 or magnetic resonance data in DICOM files 104b generated from the magnetic resonance imaging system 106). In some embodiments, the magnetic resonance data includes one or more echo measurements and/or one or more weighted MR maps each having one or more magnetic-resonance contrast data.

To perform the in-vivo imaging, the analysis system 102 includes a processing module 108 configured to amplify (206) portions (i.e., myelin-specific regions) of a k-space map 110 associated with the spatiotemporal signatures of magnetic relaxation associated with myelin-restricted water to generate a myelin-amplified k-space map. The k-space map 110, in some embodiments, is generated (step 204) from the DICOM file 104b locally, or remotely, stored from the magnetic resonance imaging system 106. In other embodiments, the k-space map 110 is generated (step 204) from raw magnetic resonance data internal to the magnetic resonance imaging system 106. During an acquisition, the signal accumulated for every pixel is organized in the spatial frequency domain, mathematically termed k-space. The k-space is a quantitative data map of correlative populations of resonating spins that represent gross-to-fine tissue and sub-tissue features.

As used herein, the term "myelin-restricted water" refers to isolatable water in a water environment formed by myelin and its associated structure that affects relaxation characteristics of the isolatable water. Myelin-restricted water can include water in intra/extracellular spaces that relaxes more slowly than intermyelin water trapped between myelin sheaths as well as, in some embodiments, intermyelin water.

Referring still to FIG. 1, the analysis system 102, via the processing module 108, is configured, in some embodiments, to amplify T1w magnitude components of the k-space map 110 having associated T2 measurement values for myelin-restricted water. For a 3-Tesla MRI system, it is observed that the T2 measurement values for myelin-restricted water can be between about 5 milliseconds and about 35 milliseconds (which differs from those of lipids having values greater than 60 milliseconds). These numbers can vary among different MRI systems with different magnetic coil, gradient coil, and radiofrequency configuration and magnetic field strength and even among MRI system of the same configuration. In some embodiments, the processing module 108 performs the amplification using an amplification profile that is defined as being inversely proportional to the T2 measurement values. Other amplification profile can be used. In some embodiments, the processing module 108 is configured to suppress at least one non-myelin related signature in the image when amplifying the T1w magnitude components of the k-space map.

In other embodiments, the analysis system 102, via the processing module 110, is configured to amplify other data associated with one or more echoes of one or more magnetic contrast in the k-space map 108 as a substitute for, or in combination with, the amplification to the T1w magnitude components. Examples of these magnetic contrast data can include, but not limited to, T1 data, T2 data, T2* data, MR diffusion data, MPRAGE data, gradient-echo data, spin-echo data, EPI data, BOLD data, proton density data, susceptibility data, magnetization transfer data, spin labeling data, flow data, and combination thereof) acquired from a magnetic resonance system (e.g., an MRI system having T1 and T2 measurements).

Referring still to FIG. 1, the analysis system 102 then reconstructs (step 208) the myelin-amplified k-space map 112 to generate (step 210) an MRI quantification dataset and/or visualization dataset of myelin associated tissue structure. In some embodiments, the MRI quantification and/or visualization datasets are stored in a database 113, for example, for subsequent display or analysis. These analyses can include, for example, but not limited to, classification learning, comparative learning, deep learning, and machine learning.

The MRI quantification and/or visualization datasets can also be used in the optimizing of sequences of coil designs for MRI systems.

In some embodiments, the reconstruction involves the application of an inverse Fourier transform (e.g., IFFT) to the myelin-amplified k-space map combined with a phase component of the generated k-space map. In other embodiments, the reconstruction involves other mathematical transformation of the data, including for example, but not limited to, Laplacian, Hough, Radon, wavelet, sine or cosine transformations, etc., to take the data to a biologically isolatable space (e.g., biologically-isolatable image space) to which the isolating process, e.g., as described in relation to FIG. 7, can be applied. Indeed, the use of FFT and IFFT is only an example of the various types of transformations and corresponding reciprocal transformations that can be used to isolate myelin-signals and/or other biological signals-of-interest to reveal in vivo myelin compaction in MRI system and other transformations including those recited herein can be used.

The generated MRI quantification and/or visualization dataset of the myelin associated tissue structure is outputted to a display or to storage (e.g., for subsequent display or analysis or optimizing sequences of coil design, e.g., organized, classified, and/or stored on a data library/collection for learning, comparative learning, machine learning, or digital memory of research or medically relevant knowledge buildup). As shown in FIG. 1, the analysis system 102 includes a reconstruction/visualization module 114 configured to reconstruct the myelin-amplified k-space map 112 to generate the MRI quantification dataset and/or visualization dataset and to generate a visualization of the MRI quantification and/or visualization dataset compaction. The reconstruction/visualization module 114 can be performed in a single module or in multiple modules. FIG. 1 shows a compaction heat map 116 of myelin and its associated structure, a tractography image 118 of myelin and its associated structure, and/or a histogram 120 density of myelin and its associated structure, as an example.

FIG. 3 is a diagram of a myelin compaction heat map 116 generated by the myelin-signal isolated Magnetic Resonance System of FIG. 1, in accordance with an illustrative embodiment. The heat map 302 shows the isolated myelin-signal components in a source T1w image (shown as 304).

FIG. 4 is a computer-generated three-dimensional (3D) visualization 116 of a myelin compaction heat map dataset generated from results outputted by the myelin-signal isolated Magnetic Resonance System of FIG. 1, in accordance with an illustrative embodiment.

As used herein, the term "myelin compaction" refers to the physicochemical restriction imposed to intermyelin water by myelin membranes redundant to neuronal axons. The degree of compaction of myelin membranes can regulate the capacitance of the myelin sheath and drives conduction velocity in neurophysiological systems. Biologically, the loss of compaction of myelin sheaths can indicate nervous system and nerve fiber aging, degeneration, pathology whereas increased compaction can indicate youthful myelin and myelin regeneration. Myelin compaction can correlate to nerve fiber integrity as highly compact layers are observed in remyelinating/regenerating axons, while injured, aging or malfunctioning nerve fibers are observed to have disintegrated sheath cross-sections. The siMRI-obtained myelin compaction index can be a measure of the voxel-predominant degree of sheath compaction to directly assess intermyelin water restriction, including, e.g., in the axon and/or periaxonal compartments, and can be used to rescale differences between regions that are intermyelin-water restricted and regions that are not to form a new image contrast that displays myelin compaction maps.

FIG. 5 is a diagram of a myelin volume histogram (e.g., 120) of a quantification dataset showing distribution of myelin volume generated from results outputted by the myelin-signal isolated Magnetic Resonance System of FIG. 1, in accordance with an illustrative embodiment.

FIG. 6 is another computer-generated tractography of isolated myelin from results outputted by the myelin-signal isolated Magnetic Resonance System of FIG. 1, in accordance with an illustrative embodiment.

It is contemplated that the generated MRI quantification and/or visualization dataset includes visualization and/or quantified data of myelin plasticity, or associated degradation thereof (e.g., from an inflammation or inflammatory process). In some embodiments, the generated MRI quantification and/or visualization dataset includes visualization of myelin integrity including visualization and/or quantified data of intact myelin, degenerating myelin, and regenerating myelin when present in a subject (e.g., animal model, patients, harvested or cultured tissues) associated with the obtained magnetic resonance data.

It is also contemplated that the generated MRI quantification and/or visualization dataset of the myelin associated tissue structure can be used to detect a myelin structure-related pathology or condition. Examples of such pathologies and conditions include, but not limited to, multiple sclerosis (MS), Parkinson's disease, Alzheimer's disease, spinal cord injury, brain injury, concussion, mild repeated neural injury, cancer of the nervous system, myelopathy, white matter/axonal damage after surgery of the nervous system, age-related cognitive decline, age-related motor decline, among others.

The generated MRI quantification and/or visualization dataset, in some embodiments, is used to detect a myelin structure-related evaluation of post tumor resection margins, post-surgery and/or post radiotherapy in the nervous system or in nerves of the body (e.g. the optical nerve alone, the femoral head nerve branch, the hepatic nerves, etc.).

The generated MRI quantification and/or visualization dataset, in some embodiments, is used to detect and/or inform myelin-related developmental assessments, myelin-related developmental disorders, improvements of life style changes, exercise performance, drug addiction, drug efficacy, neuronal function in developmental population (young adults), motor learning, therapy, games, behavioral, prenatal assessment of neurological development, athletic performance.

Spatiotemporal Signatures of Myelin: k-Space Discovery Loop

FIG. 7 is a flow diagram of a method 700 of isolating spatiotemporal signatures of myelin-restricted water in myelin-specific regions of a k-space map, or components thereof, in accordance with an illustrative embodiment. In FIG. 7, the analysis system 102 (or another system) iteratively evaluates (702) spatial regions in the k-space map in successive stages n (e.g., $1 \leq n \leq 8$, as shown in FIG. 7) to identify and remove k-space regions that do not affect or contribute to measured values in a biologically-induced region-of-interest associated with myelin-restricted water and associated regions of interests (e.g., within a reconstructed image generated from a modified k-space with specific k-space regions nulled). The k-space regions that are not removed from further consideration (i.e., deem relevant to myelin and its associated structure) are subjected to a spatiotemporal fingerprint loop analysis (712) that assesses, on a point-by-point basis, whether the T2-relaxometry characteristics at a given k-space point within the identified myelin-relevant k-space region has a characteristic (e.g. mono-exponential characteristics) associated with myelin-restricted water.

Although various image transformation methods could be used to generate the spatial k-space or its equivalent (e.g. the Laplacian-transformed space, Hough-transformed space, Radon-transformed space, wavelet-transformed space, sine or cosine-transformed space, among others), temporal relaxation of interest can have an exponential signature that can be mono (pure) or of higher order (interfering with others). The siMRI system can use a combination of spatial representation and corresponding forward/reverse transform that allows the most accurate temporal fingerprinting associated with a particular biological feature. Indeed, for myelin compaction, the use FFT/IFFT and mono-exponential provides results suitable for clinical and research use. The selection of the spatial representation and corresponding forward/reverse transform can be used in the design, for example, of new radiofrequency systems for MRI, as well as to drive custom hardware design dedicated to the quantitative imaging of particular biological measurand.

Indeed, the system applies in successive stages one of the evaluative patches (e.g., in a pre-defined scanning sequence or random sampling manner) to the k-space map (e.g., 110) to produce a modified k-space map (e.g., 112). The evaluative patches, in some embodiments, include null portions having global maximum or global minimum values. The system, in some embodiments, records the intensity (e.g., total intensity) in one or more region-of-interest (ROIs) in resulting images reconstructed using the modified magnitude component of the k-space map (e.g., 706) combined with a phase map (θ) (e.g., 722) of the k-space map 110. The system uses the intensity, or associated metrics, to evaluate whether to reject or accept the k-space regions for further consideration.

As shown in FIG. 7, in some embodiments, the system iteratively applies (702), in 8 iterative loops (n=1 . . . 8), a plurality of evaluative patches $p_n$ (704) (e.g., a nulling patch or a saturating patch, $p_1$ . . . $p_8$) to an associated magnitude component M (706) of the k-space map 110. The evaluative patch $p_n$ (704) is configured as a nulling patch in FIG. 7 having a value $p_n$=0 (708). The system applies (712) an evaluative patch $p_n$ (704), on a point-by-point basis, to the k-space magnitude M (706) at each of the successive stages of n (702) in which the patch $p_n$ (704) has a pre-defined geometry or distribution to produce a modified k-space map M' (714).

To record the intensity (e.g., total intensity) in the one or more region-of-interest (ROIs), the system performs a reconstruction (716) of the modified k-space map M' (714) to generate a modified image Img' (718). The system, as shown in this example, performs an inverse Fourier transform (720) of the modified k-space map M' (714) combined with the phase component θ (722) (of the original image Img (724)) to perform the reconstruction (716). The system records (726), at each iteration n, the total signal intensities $S_n$ (728) associated with a $ROI_m$ (730) located at a specified location within the modified image Img' (718). In some embodiments, three regions-of-interest ($ROI_m$) are, at least, defined in each of the images for calculation of the signal in each iteration of the signal isolation process, including a surgically-induced demyelination site in the spinal cord (referred to as $ROI_{lesion}$); an area in the spinal cord having normal appearing white matter (referred to as $ROI_{NAWM}$); and a region of noise outside of the sample for reference (referred to as $ROI_{noise}$).

As shown in FIG. 7, the system performs eight evaluations n=1 . . . 8 using 8 patch configurations ($p_1$ . . . $p_8$) and records the ROI signal intensities $S_1$ . . . $S_8$. The system determines $S_{n(lesion)}$ (732) for biologically-induced region-of-interest associated with myelin-restricted water and associated regions of interest and $S_{n(NAWH)}$ (734) for a control region corresponding to normal-appearing white matter (NAWM). The system also determines a signal-to-noise ratio $SNR_n$ (736) of the standard deviation of the ROI associated with NAWM (shown as "stdev($ROI_{NAWM}$)") over a standard deviation of a ROI associated with noise (shown as "stdev($ROI_{noise}$)"), as shown in Equation 1.

$$SNR_n = 0.655 * \frac{stdev(ROI_{NAWH})}{stdev(ROI_{noise})} \quad \text{(Equation 1)}$$

An evaluative patch $p_n$ (704), and its corresponding spatial location in the k-space map 108, is considered relevant for myelin-restricted water and associated regions of interests based on two criteria: (i) if the ratio ($S_{n(Lesion)}/S_{n(NAWH)}$) was significantly greater than a baseline in a myelin-delamination-induced image only (e.g., lysolecitin-induced) and (ii) if the $SNR_n$ was significantly lower than a baseline in both a control image (e.g., saline-induced) and myelin-delamination-induced (e.g., lysolecitin-induced) images, as shown in Equation 2. The baseline, in some embodiments, is a value of the calculated ratio when no patches are removed (i.e., an intact k-space).

$$P_k = \text{select } (P_n), \quad \text{(Equation 2)}$$
$$\text{if } SNR_n \gg \text{baseline \&\& if } \frac{S_{n(lesion)}}{S_{n(NAWM)}} \gg \text{baseline}$$

In some embodiments, lysolecithin and saline are used to establish learning region of interests (ROIs). Other pharma-active compounds can be used to induce learning region of interests (ROIs), e.g., by surgically-induced myelin delamination.

The system can select and reject (738) an evaluative patch $p_n$ (704) as being a k-space patch-of-interest for myelin $P_k$ (740) based on the two criteria.

Spatiotemporal Fingerprint of Myelin Loop

As noted above, k-space regions that are not removed from further consideration (i.e., deem relevant to myelin and its associated structure) are subjected to a spatiotemporal fingerprint loop analysis (using patch 704) that assesses, on a point-by-point basis, whether the T2-relaxometry characteristics at a given k-space point within the identified myelin-relevant k-space region has a characteristic (e.g. mono-exponential characteristics) associated with myelin-restricted water.

Referring still to FIG. 7, within the k-space patch of interest for myelin $P_k$ (740), the system runs every-point $p_K$ in the patch-of-interest $P_k$ (740) through a spatiotemporal fingerprint loop analysis (712). In the loop analysis (712), the system calculates, using a mono-exponential function, point-by-point T2 relaxometry for each $p_K$ point within each k-space patch-of-interest $P_k$ (740). The system records the goodness of the fit and accepts the $p_K$ point as being a part of the spatiotemporal signatures (shown as $p_{K\_myelin}$ point (744)) of myelin-restricted water when the fit has a R-squared greater than 0.95. That is, only k-space points with mono-exponential behavior of relaxation were included as part of the spatiotemporal signatures of magnetic relaxation associated with myelin-restricted water.

Each point ($p_K$) in the patch $P_k$ can be described in either T1w or individual T2-echo maps as described in Equations 3 and 4, where $M_{T1W}$ and $M_{TE}$ are the intensity in the magnitude maps of T1w and $T2_{Echoes}$, respectively.

$$p_K = M_{T1W}(k_x, k_y) \text{ in } T1w \text{ If } M_{T1W} \in T1w \quad \text{(Equation 3)}$$

$$p_K = M_{TE}(k_x, k_y) \text{ in } T2_{TE} \text{ If } M_{TE} \in T2_{Echoes} \quad \text{(Equation 4)}$$

To validate the results, the system performs (726) a myelin temporal signature test by evaluating at every $p_K$ point of patch $P_k$ for a degree of compaction that will modulate the myelin-specific contrast of the images once reconstructed. The system then tests the inverse of relaxation constant calculated by the fit, e.g., the T2 constant of each $p_K$ point of patch $P_k$, to the interval of myelin-restricted water relaxation experimentally observed elsewhere as 5≤TE≤35 ms. Points $p_K$ of patch $P_k$ are considered to pass a myelin temporal signature test if $T2_{p_K} \in [5 \text{ ms-}35 \text{ ms}]$. The system divided this temporal window in six intervals equally spaced (i.e. 5-10 milliseconds, 10-15 milliseconds, etc) for further amplification.

As shown in FIG. 7, a set of evaluative patches is generated that corresponds to different spatial location in the k-space map (110). In FIG. 7, for a k-space map having a dimension of 128×128, the patches include a patch n=1 having a region defined by x=1 . . . 8 and y=1 . . . 128; a patch n=2 having a region defined by x=9 . . . 16 and y=1 . . . 128; a patch n=3 having a region defined by x=17 . . . 24 and y=1 . . . 128; a patch n=4 having a region defined by x=25 . . . 32 and y=1 . . . 128; a patch n=5 having a region defined by x=33 . . . 40 and y=1 . . . 128; a patch n=6 having a region defined by x=41 . . . 48 and y=1 . . . 128; a patch n=7 having a region defined by x=49 . . . 56 and y=1 . . . 128; and a patch n=8 having a region defined by x=57 . . . 64 and y=1 . . . 128.

It is contemplated that other patch configurations may be used, including different patch sizes and patch topology and geometry. In some embodiments, the evaluative patch has a spiral pattern. In some embodiments, the evaluative patch has an asymmetric distribution pattern. In some embodiments, the evaluative patch has a polygonal shape. Examples of polygonal shapes that may be used include, but not limited to, a square, a rectangle, a circle, a toroid, a point, triangle, pie-wedge, and an oval.

In FIG. 7, the k-space map 108 is shown as the output of a Fast Fourier transform 710 of an inputted image Img (712) (for example, from a DICOM file), though it is appreciated that other forward and corresponding reverse transform, such as those based on Laplacian, Hough, Radon, wavelet, sine or cosine, can be used to provide a biologically isolatable space (e.g., image space) at which myelin-associated regions can be directly interrogated and evaluated. Though discussed with respect to MRI images and systems, it is contemplated that the method of FIG. 7 can be used to image contrast in other types of biomedical imaging systems. The method 700 may be performed with an analysis system external and remote to the acquisition system. In other embodiments, the method 700 may be performed within the MRI system.

Myelin Compaction Images

FIG. 8 is a flow diagram 800 of a Myelin signal-amplification loop for generating a myelin compaction image, in accordance with an illustrative embodiment. As shown in FIG. 8, the system can reconstruct a myelin compaction map (e.g., as shown in FIG. 2) by amplifying, by the one or more processors, spatiotemporal signatures of magnetic relaxation associated with myelin-restricted water (e.g., including intermyelin water/intermyelin water fraction) at myelin-specific regions of the at least one k-space map, or components thereof. As shown, the system in some embodiments applies an amplification mask AmpM (802) by multiplying the amplification mask with T1w magnitude M (706) of myelin-specific points in the k-space map $P_{k\_myelin}$ (744) that forms the spatiotemporal signatures of magnetic relaxation associated with myelin-restricted water for a given MRI dataset. The system then applies an inverse Fourier transform to a complex dataset $Z_{myelin}$ generated by combining the result of the amplification with the phase component θ (722) to generate the new myelin-isolated image $Img_{new}$ (804) as shown in Equations 5 and 6.

$$Z_{myelin} = (AmpM \cdot {}^*M[pK_{myelin}]) \cdot e^{i\theta} \quad \text{(Equation 5)}$$

$$Img_{new} = IFFT(Z_{new}) \quad \text{(Equation 6)}$$

The amplification mask AmpM (802), in some embodiments, is derived from myelin amplification factors (MAFs), which can be defined as a decreasing multiplicative ratio among 30-fold and 2-fold with respect to intervals of T2 relaxation having an inverse relationship between the intensity of $p_K$ points (corresponding to certain spatial frequencies) and myelin water restriction (which can be interpreted as myelin compaction). To this end, the amplification mask AmpM (802) can be derived from the T2 relaxometry map and contains MAFs in each $p_K$ point that passed the temporal signature test, and 1 otherwise. FIG. 9 is a diagram of an exemplary Myelin amplification factors (MAFs), in accordance with an illustrative embodiment. As shown in FIG. 9, $p_K$ points significantly loaded with $5 < T2_{p_K} < 10$ milliseconds would be ultimately amplified by the highest MAF; and a lower MAF would be applied to $p_K$ points significantly loaded with $30 < T2_{p_K} < 35$ milliseconds.

To improve the amplified contrast (e.g., as shown in FIG. 2), the system applies in the myelin compaction images, a color code (e.g., with seven colors representing equally-spaced, increasing levels of intensity) to represent varying degree of myelin compaction levels.

3D Myelin Compaction Images

As noted above, FIG. 4 is a computer-generated three-dimensional (3D) visualization 116 (also referred to as a "3D myelin siMRI compaction map") of a myelin compaction heat map dataset generated from results outputted by the myelin-signal isolated Magnetic Resonance System of FIG. 1, in accordance with an illustrative embodiment. Myelin compaction refers to the cross-sectional sheath compaction that wraps neuronal axons in living systems.

FIG. 10 is a flow diagram 1000 of a method to generate the 3D myelin siMRI compaction map of FIG. 4, in accordance with an illustrative embodiment.

Given the physical gap between each slice in $T2_{Echoes}$ and T1w, the system can compute myelin amplification three-dimensionally by applying (step 1002) $AmpM_{slice}$ mask generated from each $T2_{Echoes}$ slice to a consecutive series of center-matched slices of the T1w magnitude maps in the k-space domain. The system can generate $AmpM_{slice}$ mask for each T2 slice which spatially describes on a point-by-point basis the synthetic contrast attributed to the detected prevalent myelin compaction level encoded in each ($k_x$, $k_y$) point of the Fourier-transformed T1w image. The system can reconstruct (step 1004) the images from k-space on a slice-by-slice basis in which each slice is processed according to the process described in relation to FIG. 8 (e.g., where the amplified magnitude and original phase maps are used for the reconstruction in every plane). The resulting reconstructed kernel is a 3D myelin siMRI compaction map (also referred to herein as "myelin siMRI"). The system can save the siMRI file in DICOM and/or NIFTI formats, among others.

The system can create (step 1006) a volume in image space by interpolating, smoothing, and/or recoloring the 3D myelin siMRI compaction map. In some embodiments, the system applies a profile comprising a S-shaped curve to the compaction values. In some embodiments, the profile has a range corresponding to the amplification factors (e.g., between about 1 and about 30). In some embodiments, the system sets compaction values associated with cortical myelin as blue; compaction values associated with highly compacted myelin as red; compaction values associated with diseased myelin (e.g., as found in multiple sclerosis plaque) as magenta and/or purple; and various other colors for intermediate values, for example, as shown in FIG. 29.

Myelin Tractography

As noted above, FIG. 6 shows computer-generated tractography of isolated myelin from results outputted by the myelin-signal isolated Magnetic Resonance System of FIG. 1, in accordance with an illustrative embodiment.

FIG. 11 is a diagram 1100 to generate a fiber tractography image based on the generated MRI quantification and/or visualization dataset of the myelin associated tissue structure. In some embodiments, the fiber tractography is generated by co-registering (step 1102) a diffusion tensor imaging (DTI) (e.g., diffusion tractography vector data) with the myelin compaction map (e.g., determined myelin compaction volumes), and coloring/display (steps 1104 and 1106) the visualization using a color map based on the myelin compaction indices from the generated MRI quantification and/or visualization dataset.

The fiber tractography provides a partially transparent 3D representation of myelin compaction in cortical and the subcortical (very compact brain areas) regions. As shown, FIG. 6 shows a complete myeloarchitecture from which fine brain structures can be observed in terms of their relative degree of myelin compaction. In this figure, it is observed that Myelin sheaths in the commissural fibers are observed to be about 3 times more redundant than the fibers in the frontal lobe. Further there appears to be right/left tract myelin asymmetry.

The generated fiber tractography image can be used for neuro navigation (e.g., for surgical planning), neuro-functional constructs (e.g., for therapy assessments), metrics (e.g., for nerve restoration therapies, including optical and other brain nerves as well as peripheral nerve de- and regeneration imaging)), as well as to inform DTI-based tractography to illustrate the density of myelin on large fiber trajectories.

Myelin-Volume Histograms

As noted above, FIG. 5 is a diagram of a myelin volume histogram (e.g., 120) of a quantification dataset showing distribution of myelin volume generated from results outputted by the myelin-signal isolated Magnetic Resonance System of FIG. 1, in accordance with an illustrative embodiment.

FIG. 12 is a diagram of a method to generate myelin-volume histograms in accordance with an illustrative embodiment. To calculate volume information, brain extraction is performed in an original T1w images using FSL, a library of analysis tools for fMRI, MRI and DTI brain imaging data. Additional description of FSL can be found at https://fsl.fmrib.ox.ac.uk/fsl/fslwiki/BET/UserGuide.

Besides FSL, other algorithms can be used, including, for example, but not limited to Brain Extraction Tool (BET).

Default BET2 command line may be used in FSL. The BET2 (brain extraction tool) deletes non-brain tissues from an image of the whole head. The output of BET2 is a binary mask that outlines the whole brain tissue volume. Right-left inversion of the data may be corrected, e.g., in Matlab. To generate the myelin specific image, the BET2 mask is multiplied to the myelin siMRI volume to extract myelin compaction information in brain tissues only.

Using the brain extracted myelin siMRIs, the system computed histograms of intensity from the 3D compaction maps, herein termed "myelin compaction-volume histograms" (MyVH). MyVHs representation quantifies the overall state of the myelin in the brain at an individual level, enabling objective comparisons across research samples and cohorts. In the MyVHs, the independent variable is the myelin compaction index (in the x axis) binned into a scale from 0-4.0 with bin-width of 0.1. This scale can be learned from observations of the contrast data from human brain analysis. The maximum observed signal was less than 4 in the myelin siMRIs. Kurtosis and skewness of MyVHs can also be calculated for each individual brain.

In addition to histograms, the system may calculate other metrics such as, but not limited to, correlation power, deep-learned, or machine-learned comparative indices, tissue classification indices, and/or tissue modeling coefficients, etc. between i) one or more myelin compaction indices derived from the generated MRI quantification and/or visualization data dataset of the myelin associated structure and ii) other MRI quantities (e.g., diffusion tensor components associated with the T1 echoes, gray level components associated with the T1 echoes, etc.)

Signal Isolation Magnetic Resonance Imaging (siMRI)—General Framework

Signal isolation magnetic resonance image (siMRI) is an iterative method of signal decomposition and image reconstruction that is combined with use of a biologically controlled measure to discover and isolate magnetic resonance (MR) signatures of direct biological correlates.

FIG. 13 is a diagram of a method 1300 of performing siMRI, in accordance with an illustrative embodiment. The method 1300 includes a discovery phase (referred to as a discovery loop) 1302, a signal amplification set of operations (referred to as a signal amplification loop) 1304, and an image reconstruction set of operations (referred to as an image reconstruction loop) 1306.

The discovery loop (1302): In this phase, a system is fed MR data of a "model" for use in a learning operation. FIG. 14 is a diagram of the discovery phase method 1302, in accordance with an illustrative embodiment.

As used herein, "model" refers to any biologically-controlled measurand to which contrasting regions of interests can be defined to isolate magnetic-resonance signal component-of-interest (hereinafter referred to as signal components-of-interest ("SOI")) of direct biological correlates. That is, an MR acquisition of model acquired in a laboratory setting would produce k-space properties that are invariant to a clinical application. In some embodiments, the model is a pre-clinical animal model (e.g., rodent or swine model of demyelination, for instance). The MR acquisition can be based on contrast data such as, but not limited to, T1 data, T2 data, T2* data, MR diffusion data, MPRAGE data, gradient-echo data, spin-echo data, EPI data, BOLD data, proton density data, susceptibility data, magnetization transfer data, spin labeling data, flow data, and combination thereof.

As used herein, the term "learning operation" refers to the isolation/identification of the magnetic-resonance signal component of interest in k-space or another transformed-image space. In some embodiments, the isolation step is performed by a person (e.g., to accept or reject the evaluative patch). In some embodiments, the isolation is performed by a machine, or deep-learning, algorithm, by a database comparison, by artificial intelligence, or by wetware. The signal component of interest can have a signature in the spatial frequency domain (which maps directly to spatial locations in k-space or the image-transformed space in use); a signature in temporal domain (relaxation); or a spatiotemporal signature that is a combination of both spatial frequency and relaxation. Myelin, as discussed, herein is an example of a biological measure having a spatiotemporal signature in MR k-space.

Referring still to FIG. 14, the method 1302 includes sequentially removing points in a transformed-image space, the k-space for example, to measure MR signal modulation upon image re-construction. A key parameter of removing k-space points or other transformed image-space points is the patch size. FIG. 14 is a more generalized version of FIG. 7 in which the patch size can be varied in accordance with the number of loops to be performed. The patch configuration of FIGS. 7 and 14 are observed to be suitable for discovering myelin SOI.

For other types of biologic measurand of interest, the patch size can be established as a function of the SOI-to-noise ratio (SNR) present in the k-space of the image. Different biological structures may have decreased SNR that require smaller patches for signal discovery. Examples of such biological structures include for example mitochondrial membranes pooled in highly metabolic areas, or deoxygenated blood perfused in concussion-related tissue.

Although shown as a polygonal shape, it is contemplated that other evaluative patch pattern may be used, including, but not limited to a spiral pattern and an asymmetric distribution pattern. Also, in addition to a rectangular polygonal shape, other shapes such as a square, circle, toroid, point, triangle, pie-wedge, and oval may be used.

The signal amplification loop (1304): The synthetic amplification of the SOI may occur in the magnitude of the MR spatial frequency domain, of the k-space, if the SOI is spatial only in nature; or it may occur in the temporal (or echoes' magnitude) if the SOI is temporal only in nature; or it may occur in both, the spatial frequencies and in the echoes, if the SOI signature is in the spatiotemporal domain. Once amplified, the system would synthetically create an enhanced fingerprint of the SOI in the new MR signal for reconstruction.

The image reconstruction step (1306): An image can be obtained from the amplified/fingerprinted k-space, or amplified/fingerprinted transformed image-space, directly or derived in two steps by mapping the temporal relaxation of amplified-and-reconstructed echoes, i.e., relaxometry maps derived from siMRI of individual echoes. In the former, the SOI is mapped out spatially. In the later, the SOI is mapped spatiotemporally. The main difference between the two is the applicability to physiological signals that exclude or include membranes (water restriction structures) or ferromagnetic/magnetizable components (i.e. blood or magnetic or membrane-type drugs).

In some embodiments, the system is configured to amplify more than one signal-components-of-interests. For example, in addition to amplifying spatiotemporal signatures of magnetic relaxation associated with myelin-restricted water, the system can also co-amplify, or amplify in a subsequent operation, a second signal-components-of-interest. Indeed, the isolating operation disclosed herein can be applied to any number of signal-components-of-interests individually, or in combination, upon image reconstruction so long as the SOI is identifiable in the temporal domain of an image. One example is to co-isolate deoxygenated-blood signals (e.g., by synthetically amplifying, in the individual echoes of a myelin siMRI map) to create a hybrid contrast of concussed tissue. As noted, other examples include mitochondrial membranes pooled in highly metabolic areas, quantifiable cancerous tissue dispersion, metabolic and/or structural surrogates of neuronal function or other biological functions, and various biologically controlled measurand in confined fluids in a living system.

Scope: siMRI can be employed to detect multi-contrast (i.e. spatiotemporal) MR signatures from specific biological structures, such as myelin sheaths or other fine membranes of physiological interest. siMRI can also be employed to detect other physiological components that have detectable MR relaxation signal, such as blood or other confined fluids in living systems. These detectable components may be of natural occurrence or may be synthetic pharmaceutical drugs, e.g., that disperse throughout the physiological system while maintaining an invariant and/or predictable magnetic resonance property.

Range of applications: Myelin-signal isolated imaging can be used to detect, diagnose, and/or evaluate myelin structure-related pathologies such as multiple sclerosis, spinal cord and brain injury, concussion or mild repeated neural injury, myelopathy and age-related cognitive and motor decline. Myelin detection for correction and informed enhancement of tractography can be used for education; neuro navigation (e.g., for surgical planning); neuro functional constructs for therapy assessments and metrics for nerve restoration therapies, including optical and other brain nerves; peripheral nerve de- and regeneration imaging, etc.

The siMRI techniques can be applied, e.g.: to the imaging of enhancement of blood oxygen-level dependent (BOLD) contrast in brain and tumor imaging, for improvements in tissue segmentation in MRI for diagnosis of cancer and immune disorders, for enhancement of water diffusion imaging and diffusion of dissociated drugs in physiological environment, for imaging of highly metabolic areas in living systems surrogated by mitochondrial membranes pooled in small compartments; for imaging of deoxygenated blood in concussed tissue, etc.

The siMRI techniques can be used to image water, fat, blood, or combinations thereof, in restricted regions within physiological or synthetic membranes. The technique can be applied to image intra- or extracellular distributed, ferromagnetic or fast relaxing materials. The techniques can be used to image human, animal, synthetic and/or metallic material. The techniques can be used to image micro or nano-scale structure.

Experimental Results

Myelin Discovery Loop

A study was conducted that performed an iterative learning algorithm as described in relation to FIGS. 7 and 14 to detect spatial frequency signatures of myelin. It is observed that the system can be used to discover the k-space patches that significantly modulates the contrast of NAWM in the spinal cord relative to a surgically induced WM lesion when our siMRI T1-weighted sequence is used.

Rodent Experiments: During the study, an abrupt demyelination experiment was performed to inject lysolecithin and saline in the spinal cord of rodents to establish learning region of interests (ROIs). Laminectomy was performed to remove the dorsal lamina of the 10$^{th}$ thoracic vertebra to visualize and inject 10 uL of either lysolecithin or saline solution (control).

FIG. 15A (top and bottom) show MRI T1w images regions-of-interest associated with myelin-restricted water used as learning ROIs, in accordance with an illustrative embodiment. FIGS. 15B and 15C show biologically-derived signal that inputs the 'Myelin siMRI Discovery Loop' illustrated in FIG. 14, in accordance with an illustrative embodiment.

Specifically, FIG. 15A shows two regions-of-interests (ROIs) in rodent images considered in a k-space discovery patch loop as described in relation to FIG. 7: (i) NAWM and (i) surgical-lesions induced with lysolecithin (top) and with saline (bottom). FIG. 15B shows relative signal intensities between the lesion ROI and the NAWM ROI as a ratio of the $S_n(ROI_{lesion})/S_n(ROI_{NAWM})$ for each of the patch configurations in each iteration of the k-space discovery loop (FIG. 15B). The image contrast between NAWM and lesion ROI is remarkably modified when patch $p_2$ is nulled, as observed in FIG. 15B. The inset boxes highlight the baseline contrast and the signal change when the discovery patch is nulled. FIG. 15C shows the signal-to-noise (SNR) ratio calculated between signals in NAWM and background noise in the image. The SNR reveals that white matter signal is significantly reduced (*) when $p_2$ is nulled.

The abrupt demyelination experiment, injecting lysolecithin in the spinal cord of rodents, shows that the baseline of MR contrast established in image is disturbed by removal (or nulling) of only one k-space patch $p_n$, the n=2. When the magnitude of the Fourier k-space patch $p_2$ is nulled and the image of the lysolecithin-injected animal is reconstructed (with intact phase map), the average intensity in NAWM ROI drops dramatically from 1054±14 to lesion intensity level 635±14. A similar signal drop is observed when nulling patch $p_3$ in the lysolecithin but not in the saline image. Nonetheless, SNR is not altered when $p_3$ is nulled, indicating that no significant portion of signal information is affected in NAWM (both in lysolecithin and control images). The mean intensity in the lesion ROI was not significantly affected for n=1 or 4<n<8, sustaining the signal within the standard deviation of the baseline 654±21. Upon removal of $p_2$, the mean intensity of the lesion ROI was significantly altered to 601±17. Removing the same discovery patch from the magnitude data of the saline-injected animal, it is observed that both NAWM and lesion (experimentally-induced) ROIs are affected, with the mean intensity dropping from 1162±14 to 589±15 and 1150±16 to 530±18 respectively. The discovery patch $p_2$ was then selected for further temporal fingerprinting because it was observed to contain significant portions of myelin-related spatial frequencies.

Swine Model Validation: A validation study was conducted to experiment controlled demyelination in a swine model to observe the validity of the discovery patch, $p_2$, as a regional marker of myelin-loaded spatial frequencies in images acquired in a translational setting (i.e. using a head coil and enlarged FoV). The study confirms that siMRI signals are primarily derived from myelin compartments by studying demyelinated sub-cortical white matter in an adult swine model.

FIGS. 16A, 16B, 16C, 16D, 16E, 16F, 16G, 16H, 16I, and 16K show various aspects of a cross-species validation study conducted to validate the discovery patch, in accordance with an illustrative embodiment.

To translate the spatiotemporal signatures of myelin identified from the rodent model to a targeted brain demyelination model (swine), the study adjusted the discovery patches of interest from an acquisition matrix 128×128 to 256×256 while maintaining the distance from the new patch to the center of the k-space identical. The central region of the k-space holds gross contrast information and serves as a reference for both contrast and spatial frequency range. Transversal relaxation was then calculated for all individual $p_K$ points in the swine's $T2_{Echoes}$ similarly to previously described. The points that surpassed the myelin-temporal signature test were then amplified for further reconstruction of the myelin compaction maps in the swine brain images. Both the test and the amplification followed identical algorithms as described above.

In the study, a small volume of Ethidium bromide (EB) was used to induce damage to myelinating and non-myelinating glia in order to generate a focal region of demyelinated axons. EB was injected in to the motor fiber tracts of the internal capsule white matter of the swine's brain, preserving the contralateral side as a control. Craniotomy and DTI-informed neuro-navigation were used to localize the internal capsule in each swine during surgery. The swine was imaged serially before and post-surgery for a period of 8 weeks until all edema was cleared, and histology was performed in the brain tissue to assess myelin and axon integrity.

Figures 16A, 16B, 16C:
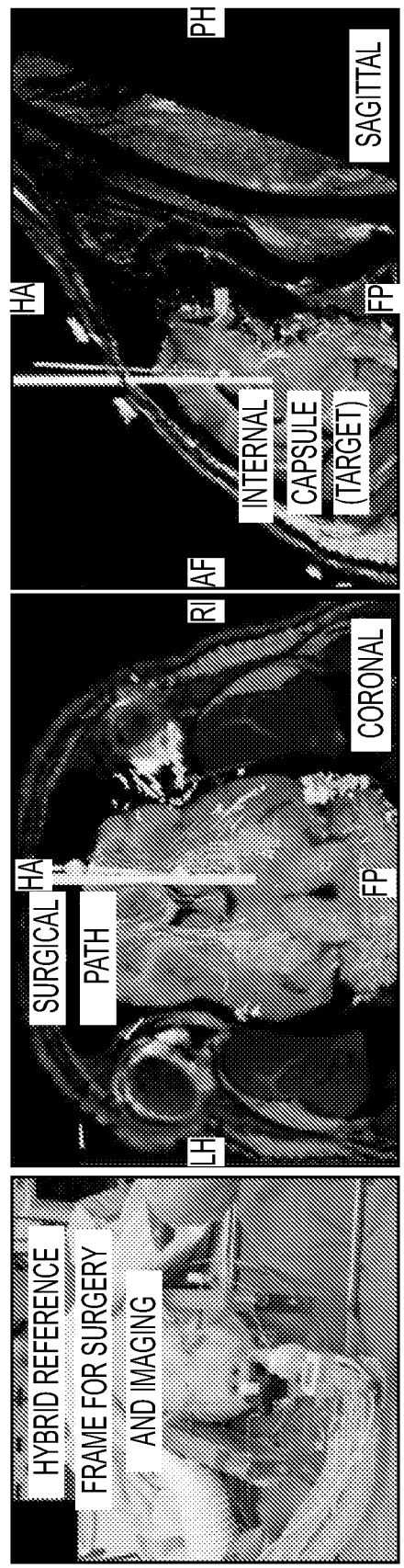

FIG. 16A shows pre-surgical images obtained for planning using a MR compatible hybrid reference frame in combination with permanent ink fiducial marks in the skin. MR hybrid reference frame and fiducial marks in the skin were used for surgical planning.

FIGS. 16B and 16C show views of the planned path, including the internal capsule target that was accessed through an anterior port to minimize mechanical disruption of white matter tracts by the injection needle. Post-surgery, the swine was imaged serially to acquire myelin siMRI T1 and $T2_{Echoes}$ data. In addition, diffusion-weighted maps were collected to observe the integrity of the white matter fibers following surgery.

Figures 16D, 16E, 16F:
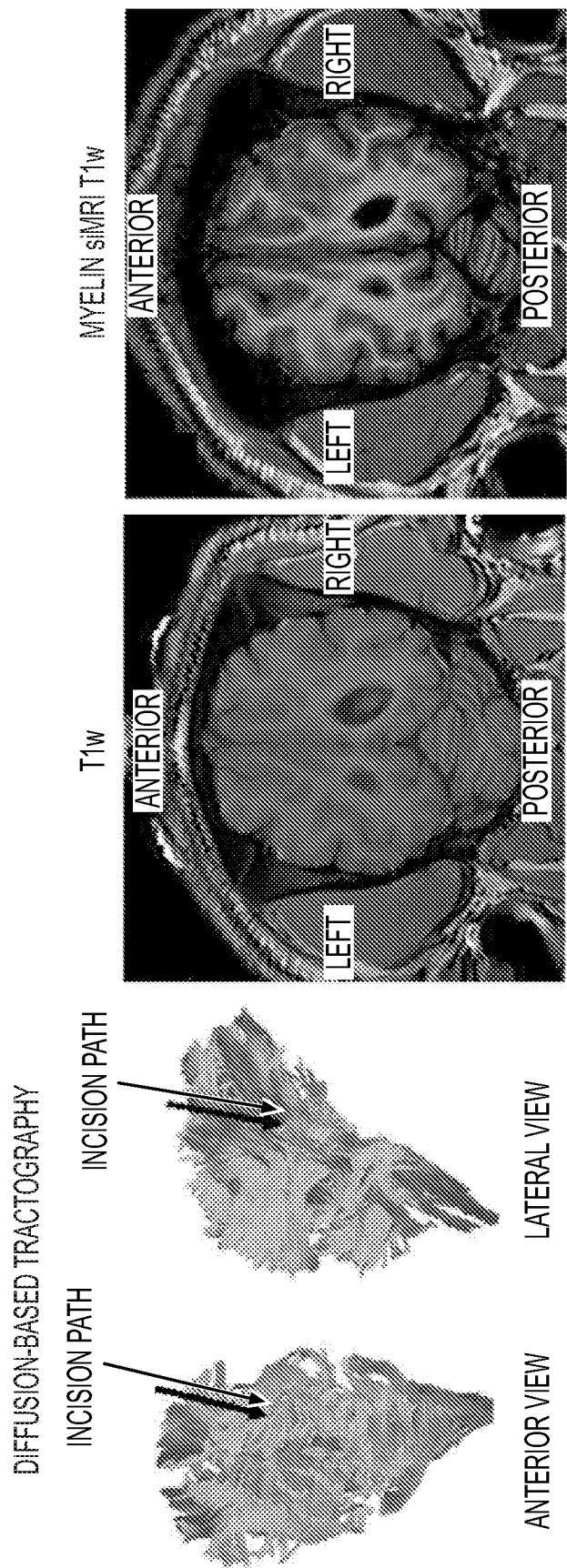

FIG. 16D shows fiber tractography that illustrates accurate targeting of the internal capsule white matter and the preservation of axon integrity during the EB injection. The post-surgery scan establishes the validity of fiber preservation during the surgery.

FIGS. 16E and 16F compare the T1w contrast achieved by myelin siMRI T1w images. The figures show demyelination sites in axial slices. Significant increases in white matter contrast is observed with myelin siMRI T1w sequence.

Figure 16G:
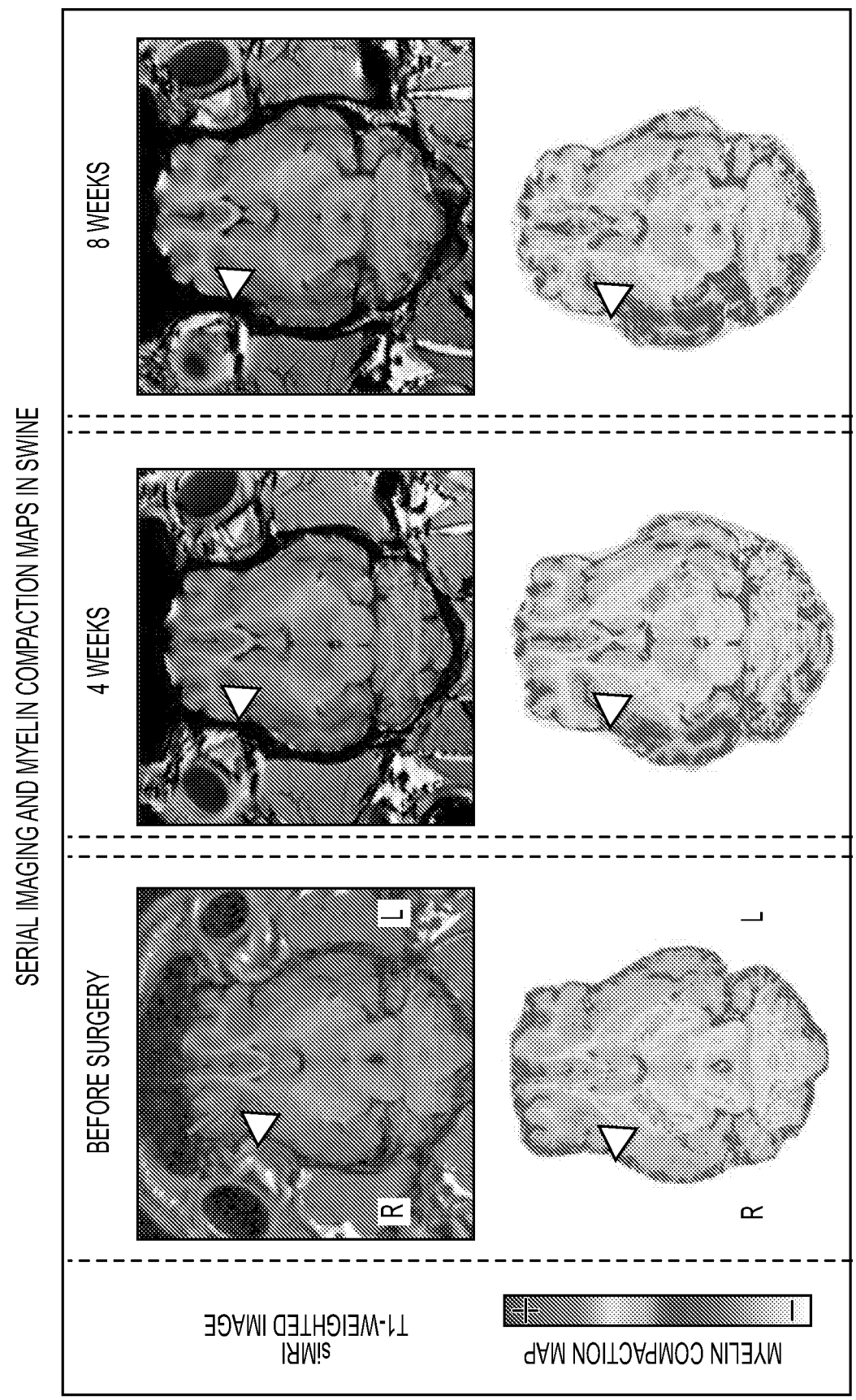

FIG. 16G shows serial post-surgery coronal scans (top) in the true coronal orientation and myelin compaction maps (bottom) at three time periods: pre-surgery, 4-weeks post-surgery, and 8-weeks post-surgery. The arrow points to the region of demyelination.

Over the course of the study, myelin compaction maps (bottom portion) measure a slow progression of toxic demyelination that extended to affect the striatum and other midline features. The visible presence of increased compaction in off-target sites, such as the contralateral tracts and portions of deep white matter in the frontal and parietal lobes, suggest that myelin development is still ongoing in the young swine model.

Figure 16H:
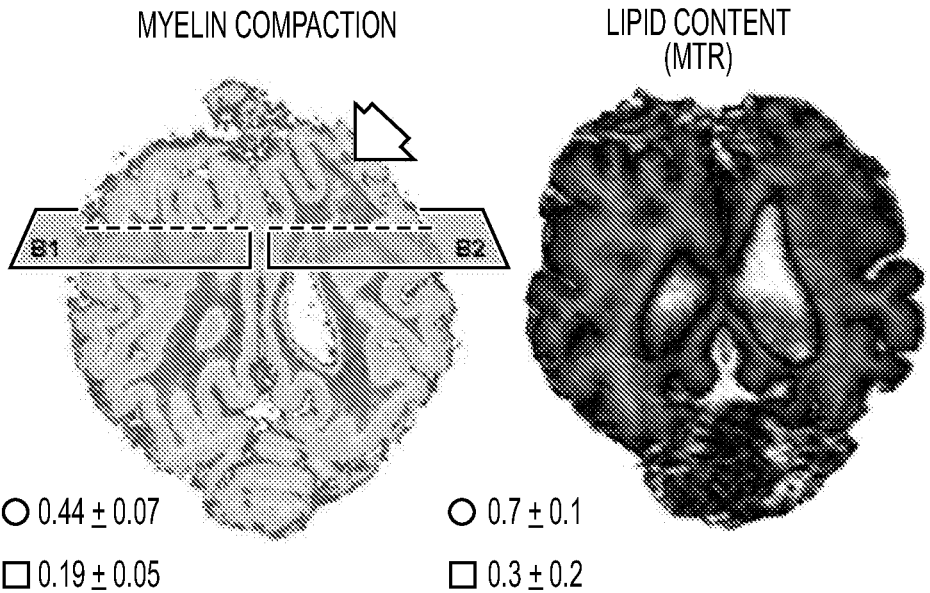
Figure 16I:
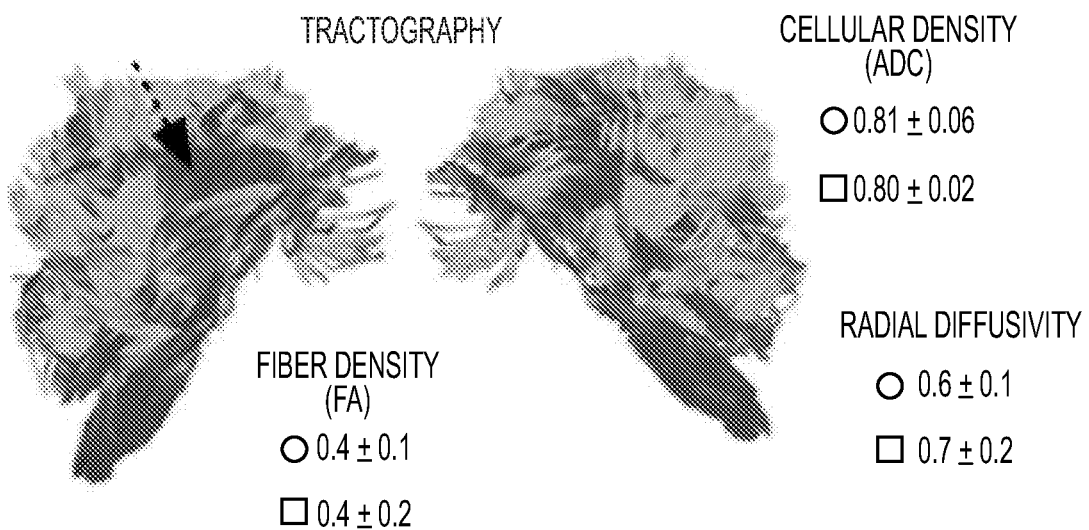
Figures 16J, 16K:
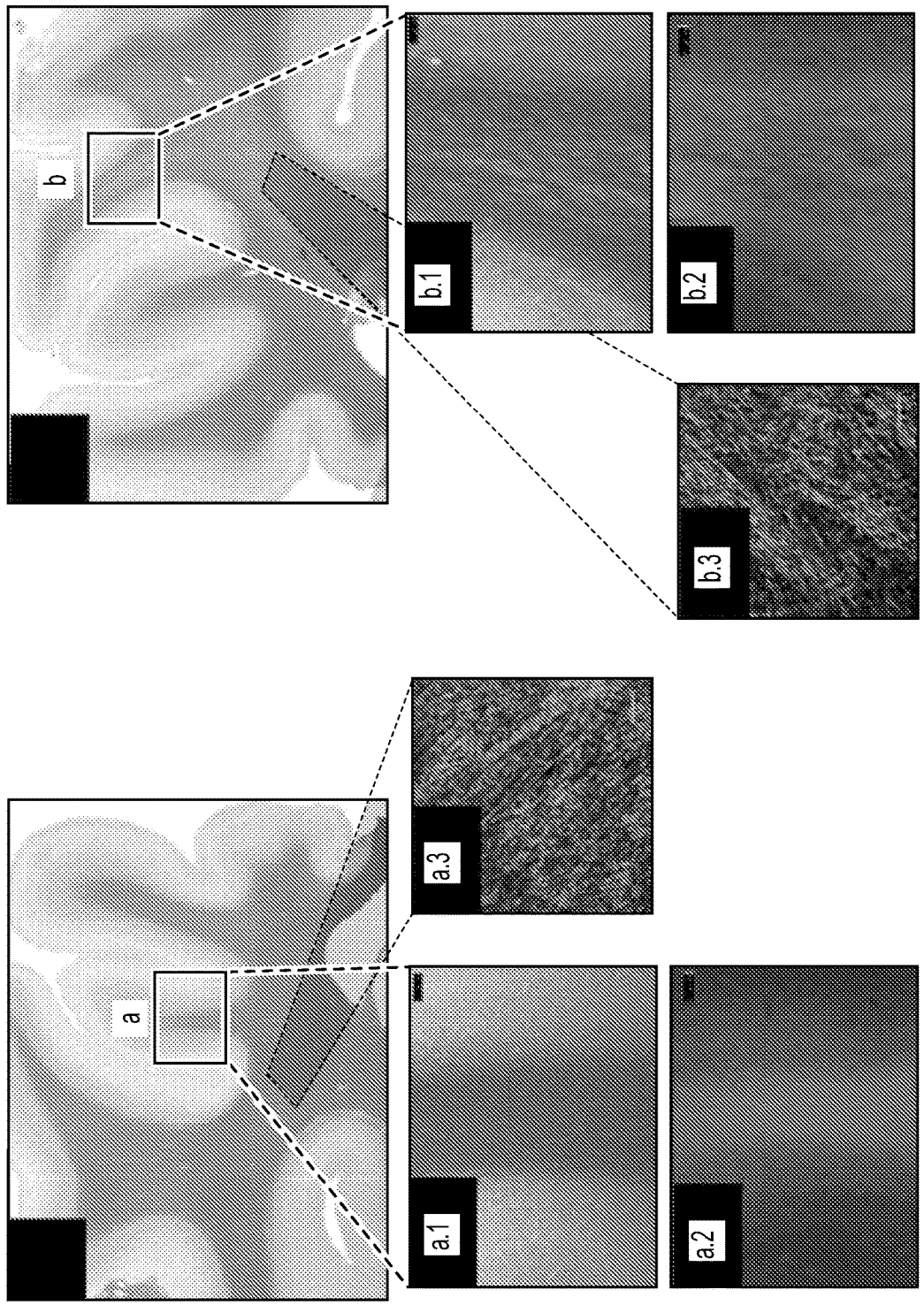

FIGS. 16H, 16I, 16J, and 16K show quantitative MRI and histology data collected at 8 weeks post-surgery in two brain regions (the target and the contralateral site (NAWM)). FIG. 16H shows that perfused tissue was sliced axially in each of the hemispheres (slices B1 and B2). The arrow points to the demyelinated target. In FIG. 16H, myelin compaction and lipid content maps (measured with MTR) are compared. The comparison shows that either of the techniques can significantly detect demyelination in the target. FIG. 16I shows diffusion-weighted data, including radial diffusivity. FIGS. 16J and 16K each shows tissue histology for NAWM and demyelinated target. The figure illustrates a lack of contrast in transillumination of the white matter (FIGS. 16J and 16K, blow outs a.1 vs. b.1), as well as by a significant loss of Fluoromyelin signal (FIGS. 16J and 16K, blow outs a.2 vs. b.2). Control images show no interruption of the white matter (WM) by uninterrupted fluorescence staining (data not shown). A separate stain of axon neurofilaments (SMI 311 and 312) shows comparative axonal density and the absence of axonal abnormalities or debris in the demyelinated area comparable to the control hemisphere (FIGS. 16J and 16K, blow outs a.3 vs. b.3). The data confirms that a verified disruption of myelin content without axon loss correlates with loss of myelin siMRI intensity indicating siMRI signals are significantly driven by myelin structure.

Aging Study—Brain Maps of Myelin Compaction

In a subsequent study conducted on patients, myelin compaction maps were computed in the whole brain by sequentially applying the spatiotemporal fingerprint and the myelin signal-amplification loops described in relation to FIGS. 17A and 17B to each slice of the image data. FIGS. 17A and 17B show matching planes of one T1-weighted map and a T2* single echo image of a 50 year old subject.

Two-dimensional Fourier-transformed spaces were considered, and the expansion to three-dimensional space took place only in the image domain. For the study, 13 volunteers were recruited. Myelin maps were measured from them to determine if aging influences myelin compaction signals.

FIG. 18 shows relaxation data of individual spatial frequencies in k-space points over time in three dimensions. Intensification of myelin-correlated spatial frequencies was set to 20-fold to exemplify the magnification of myelin-specific points (off-centered in k-space). FIG. 19 is a table of Myelin-specific T2* stratification in individual k-space compartments of the brain for a 50 years old subject. In FIG. 19, the table indicates the peaks chosen to selectively amplify water compartments at least partially derived from myelin membranes.

Subsequently, siMRI images were reconstructed using Fourier Transformation. The contrast then theoretically reflects myelin compaction. The magnified myelin signal images may be better visualized in terms of areas or volumes connected by the same myelin compaction level. The 2D series of brain slices in FIG. 17B.

FIG. 21 shows 3D views of the same and shows the leveraged information of brain myeloarchitecture obtained by siMRI. FIG. 21 was obtained by interpolating myelin siMRI slices in the "z" direction. Remarkably, the approach reveals the greatest myelin density in commissural fibers with less density in subcortical structures.

To display the myelin compaction data, isocontours were constructed within myelin compaction maps that represent areas with similar compaction indexes wherein the total scale is subdivided in five major brackets. FIG. 22 shows a myelin compaction map.

Figure 23A:
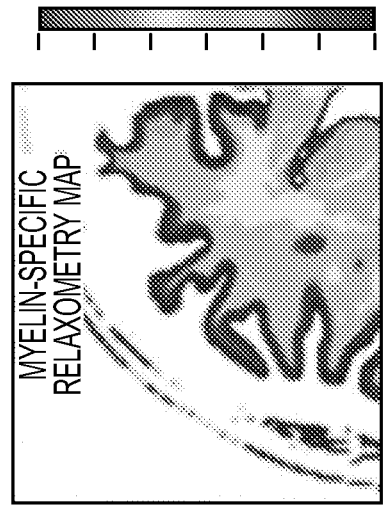
Figure 23B:
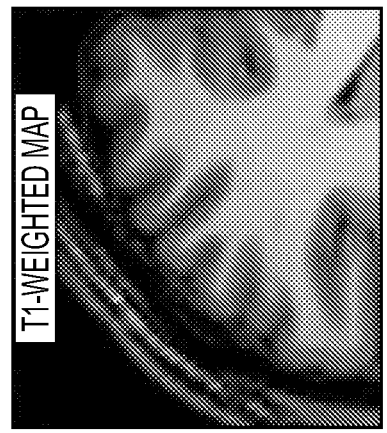
Figure 23C:
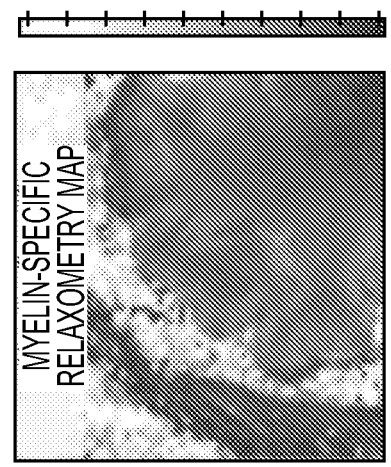
Figure 23D:
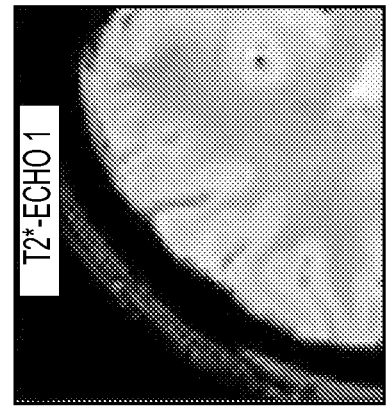

FIGS. 23A, 23B, 23C, and 23D show generated myelin-related quantitative data. Qualitatively, explicit differences in myelin information were also extracted from zoomed regions of interest from T1, myelin compaction map, T2*-echo and T2* relaxometry for comparison. These data show a direct comparison between k-space based myelin siMRI map (FIG. 23B) and T2* relaxometry map ordinarily calculated in the image domain (FIG. 23D).

FIGS. 24A and 24B show relaxometry data in the image domain and in the magnitude of the k-space domain, and myelin maps generated from both, in accordance with an illustrative embodiment.

Relaxometry is ordinarily performed in the image domain often for visualization of white matter minutiae at the pixel resolution level, commonly in the order millimeters. In this case, one transversal relaxation curve is obtained per pixel, which, in turn, combines decays from different sub tissue structures contained within the pixel space. These curves are mono or bi-exponential for example, allowing mathematical differentiation of one or two sub pixel water compartments. In contrast, relaxometry was performed in the spatial frequency domain where the signal from sub-tissue structures is already segmented at the signal detection resolution level, i.e. before contrast is distributed across the matrix to form the image. The study sought to determine if myelin signal isolation is statistically improved by computing relaxation in k-space compared to derivation from the image domain. The coefficient of determination for exponential fit in normal appearing white matter areas is increased from $R^2<0.6$ in the image domain to $R^2>0.96$ in k-space relaxometry (FIGS. 24A and 24B). The data highlights the increase in the overall significance of myelin-specific signal in the whole data histogram of intensities in image and k-space domains respectively. The increased sensitivity of reconstructing signal via k-space underscores the importance of collecting these data and the potential future challenge of retrospectively deriving myelin compaction from the image domain.

Human Myeloarchitecture viewed by siMRI: The study created 3-dimensional image maps from a fifty-year-old control brain to illustrate the utility of myelin siMRI for mapping and assessing myelin structures with and without corrections for fiber density. FIG. 25A shows a series of sequential brain slices of T1 contrast acquired from the brain of a 50 years old normal control subject. FIG. 25B shows isocontours within corresponding myelin maps calculated from siMRI. Remarkable anatomical continuity in fiber traces, matching known fiber tracts, is shown in both coronal and sagittal views. Rich details can be qualitatively extracted from these series. For example, the leftmost myelin map in series. FIG. 25B shows amplification of inter-myelin water specific signal in T2*/T1 k-space lines. Myelinated neuron fibers can be observed in the three-dimensional pattern of compaction. It is observed that the cerebellum has myelinated fibers with different degrees of compaction that can be up to 2× more redundant in the center than in the periphery. Also, the images in the series give a glance of the myeloheterogeneity of the spinal cord too. Major structures, such as the internal capsules, commissural fibers, some inner shells of the occipital and limbic lobes, are shown with high levels of redundancy in terms of myeloarchitecture though differing from the frontal lobe in this subject, for example.

FIG. 25C is diffusion-based tractography (DTI) colored by myelin compaction indices. The color-scale reflects, from blue to red, the least to most highly compact myelin. An increase in myelin compaction in the commissural and association fibers (red) with decreased compaction (blue) in sub-cortical fibers was observed.

Myelin Tractography: Myelin maps may be used to indicate increased compaction in discrete, large white tracts and less compaction in white/gray matter transitions. Myelin siMRI could be applied to correct or inform DTI-based tractography to illustrate the density of myelin in large fiber tracks.

A partially transparent 3D representation of myelin compaction in cortical versus subcortical regions (illustrating very compact brain areas) is illustrated in FIG. 21. The complete myeloarchitecture can be observed in the figure. A whole brain view is shown in the sagittal and coronal views in which fine brain structures can be observed in terms of its relative degree of myelin compaction. For instance, in FIG. 21, myelin sheaths in the commissural fibers are observed to be about 3 times more redundant than association fibers in the frontal lobe. Further there appears to be right/left tract myelin asymmetry that could be explored and identified.

siMRI Depicts Human Brain Aging: One of the studies discussed herein also conducted whole brain calculations of myelocompaction computed in k-space for all subjects within the age bracket 22-88 years.

FIGS. 26A, 26B, 26C, 26D, 26E, 26F, 26G, 26H, 26I, 26J, 26K, 26L, 26M, and 26N show signatures of k-space relaxation that correlate to aging across a small population of normal control brains. Specifically, FIGS. 26A, 26B, 26C, 26D, 26E, 26F, 26G, 26H, 26I, 26J, 26K, and 26L show transversal relaxation (T2) constant individually calculated for k-space spectral lines that peak off axis from the center of the whole brain spectrum. FIG. 26M and FIG. 26N show an axial and birds' eye view (BEV) position of the considered slice and the position of the $k_y$ lines in the field-of-view (FOV). Dashed lines inset show statistically significant aging trends (R-squared>0.75). The shaded data correspond to points excluded from the linear fit (i.e. zeros that symbolize non-existing peaks or non-correlated data).

Further, FIGS. 26A, 26B, 26C, 26D, 26E, 26F, 26G, 26H, 26I, 26J, 26K, and 26L show correlation analysis between myelin T2 relaxometry signals computed in a single axial, orientation matched slice. Each figure associated with a letter of each panel shows relaxometry constants that may be mapped to individual k-space lines (FIG. 26N) across all individuals. The study found remarkable diversity in the impact that age has on how relaxation peaks vary and resolve with change in age. For example, aging is observed to results in significant signal degeneration (i.e. increase in T2) in k-space lines. In FIGS. 26C-26L, the k-space lines are observed to potentially indicate decreased in myelin compaction across aging: in FIG. 26C (R2>0.8), in FIG. 26E (R2>0.7), in FIG. 26H (R2>0.8), and in FIG. 26I (R2>0.6); in FIG. 26G (R2>0.7), in FIG. 26J (R2>0.9), in FIG. 26K (R2>0.6), and in FIG. 26L (R2>0.5).

Data from elderly volunteers (80 and 88 years old) indicate that the farthermost k-space lines, which, in turn, represent very high spatial frequencies (i.e. fine structures within the myelin signal window) are lost with aging. Young subjects (age<25 years) surprisingly were found to lack detectable spatial frequency lines observed in FIGS. 26C, 26H, and 26I. In turn, these lines (in FIGS. 26C, 26H, and 26I) are rather strongly correlated with brain maturation in subjects with age between 32-65 years. Together these data facilitate the study of structural relevance of these line patterns in normal aging but also how they may be altered in brain disease.

FIG. 27 shows detailed statistical analysis of quantitative losses of myelin compaction in an aging study using siMRI analysis (as compared to established MRI method). Specifically, FIG. 27 shows power of correlation between myelin compaction index obtained from signal isolated MRIs (siMRI) and other classic image parameters [i.e. gray level, apparent diffusion coefficient (ADC), fraction of anisotropy (FA) and radial diffusivity] calculated for three regions of interest (ROIs) in brains of subjects with age between 22-88 years. Similar results where obtained using MRI methods.

The "R1" pane in FIG. 27 shows data for the corpus callosum (left), the "R2" pane in FIG. 27 shows data in the subcortical volume (center), and the "R3" pane shows a mid-brain volume in the corona radiata (right).

The top graphics of FIG. 27 show the network correlation between individual parameters. The correspondent linear correlation coefficients (top) and p-value calculated for the correlation between pairs of parameters (bottom) are shown in the colored triangular plots (right side). The gray-scaled plot on the bottom left shows a relative distribution of the image components vs. age. T1 gray level signal was rescaled by a factor of 10-4 to fit into a comparable visual color scale with the other parameters. Two and three-dimensional localizers of the ROIs are shown in the bottom figures over ADC and fiber track maps respectively.

Indeed, the study shows that siMRI statistically predict brain white matter aging. First, myelin compaction, T1-gray level, apparent diffusion coefficient (ADC), fraction of anisotropy and radial diffusivity were shown to be individually correlated with age. Only the commissural fibers in R1 showed a significant trend of correlation (>0.85) between myelin compaction and aging with the exception of two youngest outliners (22 and 23 years). T1-gray level, the clinical standard for detection of plaques of demyelination, does not appear to be correlated to age in either of R1-3. ADC, thought to globally represent cellular density, shows stable values in all three volumes analyzed for healthy aging subjects. The fraction of anisotropy is increasingly dispersed among different anatomical regions but maintains constancy among different subjects across age. FA is the only diffusion-dependent parameter that significantly correlates to myelin compaction and seems to be proportional with fiber density across the entire brain. In R1, where a larger number of fibers intersect, the normalized correlation is >0.9; in R2, <0.6; and in R3, <0.2. Radial diffusivity qualitatively shows stable values across both different anatomical areas (R1-3) and aging (22-88). Hence, these statistical comparisons indicate, that in the sample of healthy subjects FA, siMRI statistically predict brain white matter aging.

Quantitative siMRI: Myelin-Volume Histograms: To further determine the value of assessing myelin compaction in the healthy brain, myelin volume histograms are binned to generate and quantify maximum myelin compaction values. The study compared, two-dimensionally, whole brain myeloarchitecture measured by myelin siMRI across aging subjects.

FIG. 28 shows relative myelin compaction maps obtained from siMRIs illustrating detailed image information of brain aging. Mid brain (left) and top brain (right) slices were selected to show losses of myelin compaction around neuron fibers with aging. In every line (in the upper portion), from left to right, the figure shows T1-weighted map, T2* single echo image, convoluted T1/T2* maps with myelin-specific signal (amplified in k-space showing 5 levels of compaction), and whole brain fiber tracts (center). In the lower portion, from left to right, the figure shows a series of myelin volume histograms (MVH) for representative ages. The green arrows emphasize the maximum compaction index (MyCI) drops dramatically with aging; and a comprehensive view of the data across the entire cohort is shown in the far right graphic. MyCI strongly predicts brain aging (R-squared>0.89).

As noted above, FIG. 28 shows these results in two particular planes: mid brain (FIG. 28, left), representing approximately the anterior-posterior (AP) line and the top of the brain (FIG. 28, right), located ~3-4 cm above the AP line, not including the ventricles. Representative images are also shown for clear visualization. The acquired, unprocessed images are shown in the first two columns of each data set followed by pixelized convoluted myelin siMRIs and those graphed in isocontours representing intervals of compaction. Whole brain tractography is also shown per subject (mid column). No detectable changes were observed in myelin compaction across these aging subjects (royal blue contours) while pericortical areas mostly located in the frontal lobe tended to lose myelin density over age (from yellow to green) as compared to periventricular areas (i.e. cross sections of the internal capsules) where intensified myelination over age (from green to orange) was observed. MVHs, noted across aging, are quantitative representations of the myeloarchitecture rearrangement in the brain volume. Representative distributions are shown (the lower portion of FIG. 28). A regression analysis of the maximum myelin compaction index measured in every brain remarkably correlates to aging ($R2>0.85$). The area under the curve is the total myelin fraction, not discriminating gray and white matter fractions since these derive from inter myelin water signals isolated regardless of myelin location in the image. The presence of an elongated tail in the young MVH (24 years) and progressive loss of maximum MyCI in 50 and 80 year old subjects potentially indicates that newly developing myelin has a higher maximum myelin compaction index (MyCI).

Discussion of Aging Study: MRI is the most sophisticated method clinically available for imaging living organs. However, assessment of brain structure and function poses a particularly difficult challenge due to the remarkable cellular and morphological heterogeneity that underlies neural function. Constraints derived from prevailing system software design and pixel resolution are chief limitations that reduce the amount of sub tissue information acquired. Methods to quantitatively distinguish neural structures such as neuronal and glial populations, nerve or myelin structure have far-ranging application to basic research and clinical diagnostics. Today most emphasis is on interpretation of data in the image domain but there has been an increasing interest in experimental analysis of k-space. In the conducted aging study, data-mined k-space were used to add quantitative, sub-cellular signals to enhance MRI images. The aging study focused on reconstructing myelin, and the results demonstrate that experimental analysis of k-space can be used for the quantification of myelin integrity to better understand brain nerve fiber structure in the healthy brain, as well as pathological alterations induced by aging, injury or disease.

Two parameters may be analyzed for indirect detection of cellular structures including myelin. During a MR signal acquisition, the contrast of spin populations in the final image is derived from the time-to-echo and the relaxation constants, T1 and T2. The signal is acquired in terms of its spatial frequencies and reconstructed into an image by applying Fourier Transform. Ultra-high field and high field magnets permit shorter pulses and faster excitations, escalating the sensitivity of the MR detection to different biological tissues and subcellular components. The MR image is an approximate representation of water compartments in the sample, and the mathematical signal collected represents fine biological structures. The image is mathematically derived from re-organization of the information compiled from the tissue prearranged in k-space. The MR k-space is an atlas of echoing patterns encountered in the real sample; and those small arrangements enclosing resonating spins, although cannot be localized any further beyond the pixel resolution, still echo individually upon magnetic excitation.

Magnetization transfer (MT) images have been previously observed to correlate with myelin content in the brain. In those images, the contrast is based on selective energy transfer between free resonating spins and those hydrating fatty layers of macromolecules. Several studies have shown that MT images can be used to visualize demyelinated plaques in multiple sclerosis, for example. Single shot MT rate maps, however, do not suffice for resolution of myelin sheaths and other high-fat content cells or vesicles in the white matter. In these regions, defective versus healthy or new myelin cannot be stratified because the lipid content is not changed significantly within each voxel; an associated measure of relaxation may be required to further classify the predominant geometry of myelin layers in the voxel. Moreover, low fiber density areas, such as the cortex, rarely overcome noise levels in low field MT measures to allow myelin visualization. Alternatively, from a spatiotemporal approach, sophisticated high field MT sequences have been further developed to acquire several off-resonance intensities within the same pixel in response to synchronized excitation pulses. This is a promising approach to resolve sub-geometries formed by complex lipid layers. The use of serial off-resonance acquisition has improved myelin detection indirectly, and the resultant images have been recently demonstrated to correlate to known resting state cortical activity. In both cases, contrasts representing indirect measurements of myelin and myelin-like membranes show co-localization with expected myelinated fibers as well as detecting the absence of fibers. Biologically, however, myelin quality is yet a more relevant quantity than myelin density given that a series of demyelinating inflammatory processes, as well revitalizing mechanisms occur in the CNS tissues upon pathology or in coordination with cortical plasticity for example. Despite the exuberant lipid content overall encountered in myelin in the white matter, the fine myeloarchitectonic contributes to understanding of fiber functionality, and its direct assessment underlines quantitative neuro diagnostic.

Interfaces between white and gray matter are still better visualized in short-angle T1 maps, conversely, due to straight proportionality between total z-direction magnetization and fluid content, inversely proportional to cellular density as a signature of the different soft-tissues in the brain. T1 maps are the most clinically used MRIs for qualitative identification of demyelination plaques in several pathologies and aging. Spin lattice maps, T1, nonetheless distinguish inter myelin water populations from other lipid-bound hydrating tiers. Microscopic characteristics of sub tissue water compartments are rather encoded in the transversal relaxation constants, T2 or its very short component T2* that are direct quantities that assess spin-spin interactions. T2 maps are obtained in the image domain by estimating the time-constant of transversal decay of spin populations sharing the same pixel area. The final contrast can favor myelin density if the data is acquired with enough SNR to yield bi-exponential decays that can be resolved to select myelin-specific T2s. In this case, the contrast is inevitably biased for myelin density (i.e. fiber density across each pixel) preventing quantitative comparisons between white and gray matter.

Furthermore, a series of widely accepted research work performed in clinical scans has shown myelin maps of the brain calculated in the image domain (either pixel-by-pixel or as an average in small volumes) that consider the fatty nature of myelin to build contrasts. Areas in the image are distinguished by altered magnetic susceptibility that modifies T1/T2 ratio. This method relies on the lipid nature of the myelin sheaths, but it correlates to the brain anatomy quasi intuitively. However, a major limitation of T1/T2 ratio is the lack of sensitivity for whether myelin matter is protein/peptide populated or uniform; compact or blebbed/ballooned; healthy or compromised; regenerating or degenerating. The entropic distinction between degradation and myelin layer production is a fundamental question that has many clinical and research implications.

In contrast, myelin compaction is distinguished in the MR signal and magnified to create a new siMRI contrast. In brain tissue, for example, myelin sheaths are repetitive structures that had been observed to have a very specific significant signature in k-space. Inter myelin sheath compartments were detected by using spatiotemporal frequencies stratified from the k-space of high resolution T1-weighted maps in combination with T2 relaxometry. A direct correspondence may exist between compact, thick and new myelin. With this bias, live aging human brains were studied to demonstrate the feasibility of myelin siMRI. siMRI contrast may intensify pixels containing myelin. Importantly, the amplification factor may be subjective and may be observed to have minor or null rings of Gibbs in intensity-windowed images if the magnification in k-space does not extrapolate the original amplitude of the central lines.

To empirically test amplification factors, dynamic myelin data may be compared in carefully controlled animal models where myelin layers can be rigorously measured. Indeed, the siMRI technique disclosed herein is observed to significantly improve isolation of myelin signal beyond any current published method. The coefficient of determination increases from <0.65 to >0.96 and, perhaps more extraordinary, is that the technique appears to differentiate degrees of myelin compaction, where stratification within the bracket 10-30 ms is clear.

Further, myelin compaction as generated using the processes described herein, and as for example shown in FIGS. 3, 4, 21 22, 25B, 28, etc., show remarkable coincidence with the normal aging myeloarchitecture, including the life-through maturation of myelin in developmental features, and can be used to reveal tract-specific, or associated, demyelination. In particular, the instant imaging techniques can be used to view features and the continuity of the corpus callosum as delineated by myelin compaction and are strikingly visible in subcortical areas and midline structures. Indeed, the co-state of the myelin—in terms of its compaction—in the amygdala, hypothalamus, and hippocampal spaces can be observed (see FIG. 28) and seems to be age independent among the subjects in the conducted aging study.

Further, the instant imaging techniques can be used to view the ventral striatum (FIG. 28) as a whole structure in terms of its continued myelin compaction levels.

Further, the instant imaging techniques can be used to observe visible differences in the myelin compaction levels at different regions of the caudate nucleus. The caudate nucleus is a known structural circlet of the brain associated with learning and cognition (generally observed to decline with age).

Further, in consonance with the expected natural degeneration of certain brain structures with age, the relative similar compaction levels in the prefrontal cortex indicate the suitability of the myelin siMRI contrast to image and study myelin-related changes, e.g., due to aging, disease, or injury. Indeed, despite the natural white matter atrophy observed in the older subject data—to which a lower amount of myelin is expected to correlate—the myelin compaction remains similar in inferior frontal and prefrontal lobes.

Further, results show that instant imaging techniques can be used to view contrast of myelin compaction independent of total myelin content; a major limitation of analysis using just T1/T2 ratio is the lack of sensitivity needed, e.g., to determine whether an observed myelin structure is a protein- or a peptide-populated and its uniformity; whether the observed myelin structure is compact or blebbed/ballooned; whether the observed myelin structure is healthy or compromised; whether the observed myelin structure is regenerating or degenerating.

The instant imaging techniques can be used to assess entropic distinction between myelin layer degradation and myelin layer production, which has many implications for clinical and research applications.

Indeed, the exemplary system and method facilitates the correction and insertion of myelin compaction information into the image in order to visually and quantitatively stratify myelin redundancy information from the relaxation of moderate spatial frequency compartments (~0.02 um-1).

Further, remarkable correlation has been observed between the signal isolated in k-space and aging subjects. The data as disclosed herein indicate that whole brain myelin compaction can be quantitatively evaluated by siMRI MVHs. This may be a useful parameter to monitor total brain myelin for understanding normal aging and pathology where myelin structures are dynamic. The most compact myelin signals were detected in young subjects (<26 years) while myelin signals observed in healthy aging indicate a decrease in overall myelin compaction or perhaps an increase in myelin pathologies as that observed in aging primates and mice.

Materials of Aging Study: In the aging study, MR data was collected using a 3T Philips Ingenia scanner and a head coil. The study used the true anatomical anterior/posterior line of every subject to co-localize the frame of acquisition for all MRI sequences.

FIG. 20 shows description of magnetic resonance sequences and illustration of images acquired in a 3T Philips Ingenia scanner, in accordance with an illustrative embodiment.

The aging study obtained high resolution T1-weighted maps using a three-dimensional fast field echo sequence with TE=3.7 ms, TR=8.1 ms, 4 signal averages, reconstructed pixel resolution of 0.447 mm, matrix of 256×256× 180, Cartesian k-space filling was set, and SENSE was inactive. Relaxometry of the T2* component was performed in 2D in 10 or 12 planes within the brain volume using a spoiled gradient spin-echo sequence with 5<TE<185 milliseconds, bandwidth=191.5 Hz, NSA=2, 10 echoes and identical k-space filling parameters and in-plane spatial resolution. SENSE factor was set to 1. A saturation slab (180× 180×50 mm) was placed in the neck area below the imaging slab (acquisition volume) to reduce blood flow contributions to transverse relaxation. The study used a high-resolution diffusion tensor imaging (DTI) sequence to calculate fiber tractography, the apparent diffusion coefficient (ADC), fraction of anisotropy (FA), and diffusivity components. For these imaging, maximum gradient in 32 directions in addition to the static field were employed with TE=94 ms, TR=9000 ms and maximum b-value=1300 s/mm2. The in-plane resolution was 1 mm and the slice thickness was 2 mm. DSI Studio (http://dsi-studio.labsolver.org) was used to calculate the diffusion tensor using a deterministic fiber-tracking algorithm with angular threshold of 60 degrees and step size was 0.5 mm. The anisotropy threshold was determined automatically and tracks with length less than 30 mm were discarded for clear visualization. A total of 5000 seeds were placed in the whole brain of each subject.

k-Space Relaxometry: Matlab (R2015b and R2017, Mathworks) was used to process all the data. T2* multi echo acquisitions and 3D T1-weighted maps were converted to the spatial frequency domain by applying a two-dimensional discrete Fast Fourier Transform (FFT) for every slice. The operation yielded a complex variable for each plane with the imaginary component representing the phase map that encodes the oscillatory nature of the spatial frequencies in the image (i.e. sine and cosine components). The imaginary data was untouched. The real portion of the data was re-organized for point-by-point relaxometry. Constants of decay were discretely calculated using parallel computing by applying mono-exponential fitting point-by-point. Statistical parameters, such as the coefficient of determination, are also acquired and recorded. An additional loop involving bi-exponential fit was used for k-space points with R2<0.8. Next, a fourth-dimensional variable describing both the T2* k-space map of the real component of the image and its imaginary portion, those calculated for every 2D MRI slice, was stored; the T1 k-spaces of z-matching plans were also computed. Observing k-space symmetry, the algorithm ran for half of the k-space maps. Myelin signal was isolated from T2* k-space relaxometry maps by restricting T2* window to the interval 5<T2<35 milliseconds. Direct correspondence between T1 and T2* k-space points was expected since both images are acquired with identical FOV alignment, matrix size and pixel resolution. Pearson correlation coefficient was calculated between z-direction T1/T2 matching plans to evaluate coherence between the spectral position of myelin-containing spatial frequencies—stratified in T2*—and further amplified in T1 contrast maps.

Myelin siMRI Contrast: All k-space points marked within the myelin relaxation window and located in the moderate spatial frequency portion of the spectra were magnified to produce a contrast bias based on the theoretical myelin space. Areas of the k-space farther from the contrast border were untouched. In this case, the area of interest was located in the first quarter off center in each k-space. Amplification factors were defined from 30x-5x respectively for T2* values ranging from 10-30 ms. Maximum magnification was empirically selected from the natural ratio between the amplitude of the central k-space peak and others of interest. Finally, the myelin-specific k-space area was intensified, and the image was reconstructed from T1/T2 tailored k-spaces by applying two-dimensional Inverse Fast Fourier Transform (IFFT). Once the images were re-built, myelin maps were represented in two forms, both normalized and plotted in 'jet colormap': pixelized color-scaled maps or isocontours traced in 5 main intensity levels. Data within the lower 10% intensity level were excluded from the images for clear visualization. Additionally, 3D reconstructions were rendered interpolating data in the z-direction.

Statistical Analyses: MatLab (R2015b, Mathworks) was used to perform all statistical analysis. Using a region-of-interest (ROI)-based analysis, power of correlation was calculated to compare myelin compaction indices with other MRI quantities (e.g., diffusion tensor components and gray level in T1) in the corpus callosum, frontal lobe and corona radiata across the entire cohort. First, the data were parameterized to age and linear correlation coefficients were calculated. Next, a network correlation between pairs of parameters was computed. Pearson's correlation coefficient and significance levels were calculated for each variable pair and ROI location.

Myelin Compaction Mapped in Multiple Sclerosis Patients

Multiple sclerosis (MS) is a devastating neurodegenerative disease that manifests in several distinct forms that are representative of the aggressiveness and anatomical focus of the pathology. A classic feature is the presentation on MRI of central nervous system inflammatory foci called plaques that are thought to be regions of inflammatory attack resulting in demyelination and remyelination events. MS patients exhibit a panoply of symptoms as well as a diverse anatomical distribution of plaques. These plaques are believed to represent inflammatory foci in the brain where demyelination events are predominant. However, minor dysregulations in myelin quality can cause axonal asynchrony and cortical impairment that precede complete demyelination represented by these plaques.

Surprisingly, anatomical co-registration of plaque position with symptoms in patients is a challenge and not always predictive of either symptomology or progression. Fundamentally, small changes in myelin quality, including shortening of internodes, loss or de-compaction of myelin layers are sufficient to produce significant slowing of axonal conduction and axonal fatigue.

In another study, referred to herein as the MS study, signal isolated MRI (siMRI) was used to quantify the myeloarchitecture of MS brains.

The study investigated whole brain myeloarchitecture in MS patients using the exemplary methods and systems that directly assess myelin integrity via signal isolation MRI (siMRI); color-scaling the whole brain tri-dimensionally based upon redundancy or ballooning of the inter-myelin compartments. The study collected data of myelin health in intra-cortical and deep white matter areas in healthy and MS subjects using siMRI.

In the MS study, it was critically observed that myelin wrapping correlates to natural aging of myelin but also how novel changes in global myelin compaction of MS subjects correlates with their broad and variable symptomology. The main results significantly observe that i) MS patients in their 30s and 40s have a global myelin compaction state (excluding plaques) analogous to that of 80 year old healthy volunteers; ii) Whole brain myelin compaction predicts whether patients are in a remission or relapsing state ($p<0.001$); iii) Functional MRI (fMRI) indicates parsing or re-routing of neural activity to compensate for global changes in myelin de-compaction. Dramatic changes in myelin compaction architecture appear consistent across our entire cohort and, extraordinarily, the plaques seem to delineate areas with highly compact—potentially newly redundant—myelin. Altogether, the generated view of myelin layer compaction contributes to the evolving literature focusing on global, subpathologic myelin changes that occur in MS but are poorly understood. Assessment of myelin health using siMRI illuminates potential new targets of pathology in living patients as well as redirect research toward a focus on non-ablative myelin damage that is broadly prevalent in white matter of the MS brain.

In the MS study, MRI data, including myelin-based siMRI and diffusion imaging, were acquired from 16 volunteers with MS and 21 normal aging adults. The MS study computed myelin siMRI-informed fiber tractography to compare diffusion parameters with myelin quality measures. The regional analysis was performed for two sets of white matter tissue: i) ROIs were defined in deep, peripheral or lesion rim areas to quantify myelin compaction in plaques, and ii) ROIs were additionally defined across "normal-appearing" structural areas masked to the presence of plaques; whole brain histogram of myelin compaction was computed for these ROIs.

Compared with normal aging adults, the MS study observed a decline in the myeloarchitecture of those with MS. The maximum myelin compaction index measured in the tail-end of the histograms quantitatively provided evidence for a global reduction in myelin compaction, such that there was a critical decrease in myelin integrity compared with the normal aging population. Extraordinarily, the plaques seem to delineate areas with highly compact myelin interpreted as either newly regenerated myelin, redundant myelin wrapping or fibrotic processes.

FIG. 29 illustrates the use of myelin siMRI as a tool to add insights to the MS brain. In FIG. 29, the data range that appears for MS is presented in red vs. highly compact myelin in pink. Indeed, multiple sclerosis plaques can be discerned from otherwise radiologically invisible highly compact sites. siMRI thus help differentiates between loss of compaction (that surrogates for degeneration), in red on the myelin compaction map, and highly compact myelin (in pink) that—so far—has been hypothesized to refer to myelogenesis.

Further, as shown in FIG. 29, compaction values associated with cortical myelin were set as blue. Compaction values associated with highly compacted myelin were set as red. Compaction values associated with diseased myelin (e.g., as found in multiple sclerosis plaque) were set as magenta and/or purple. Various other colors were set for intermediate values. Other coloring schemes can be used.

FIG. 30 show a longitudinal sequence of the whole brain amplified with myelin siMRI in accordance with an illustrative embodiment. The imaging may be used to support intervention trials and discovery of efficient new therapies. In FIG. 30, image data of a female patient: 32 years old, EDSS: 3.75, TEL flair-up: 11 mo., DD: 11 y, 1 pregnancy is shown.

FIG. 31 shows a comparison between Myelin siMRI tractography for MS and age matched healthy subjects, in accordance with an illustrative embodiment. The figure illustrates severe modifications in the myelin integrity, not only near plaques, but all over the brain.

The assessment of the global myelin compaction state (excluding plaques) of MS patients suggest a severe degradation in myelin integrity, which was similar to the analogous process of demyelination due to aging. Patients in their 30s-40s showed a global myelin compaction comparable to that of 80-years old healthy volunteers. Whole brain myelin compaction may be used to assess demyelination states in MS patients and to predict whether patients are in a remission or relapsing state. Resting state functional MRI (rfMRI) indicates parsing or re-routing of neural activity to compensate for global changes in myelin de-compaction.

Exemplary Computing Device

Referring to FIG. 32, an example computing device 3200 upon which embodiments of the invention may be implemented is illustrated. For example, each of the system 102 and databases described herein may each be implemented as a computing device, such as computing device 3200. It should be understood that the example computing device 3200 is only one example of a suitable computing environment upon which embodiments of the invention may be implemented. Optionally, the computing device 3200 can be a well-known computing system including, but not limited to, personal computers, servers, handheld or laptop devices, multiprocessor systems, microprocessor-based systems, network personal computers (PCs), minicomputers, mainframe computers, embedded systems, and/or distributed computing environments including a plurality of any of the above systems or devices. Distributed computing environments enable remote computing devices, which are connected to a communication network or other data transmission medium, to perform various tasks. In the distributed computing environment, the program modules, applications, and other data may be stored on local and/or remote computer storage media.

In an embodiment, the computing device 3200 may comprise two or more computers in communication with each other that collaborate to perform a task. For example, but not by way of limitation, an application may be partitioned in such a way as to permit concurrent and/or parallel processing of the instructions of the application. Alternatively, the data processed by the application may be partitioned in such a way as to permit concurrent and/or parallel processing of different portions of a data set by the two or more computers. In an embodiment, virtualization software may be employed by the computing device 3200 to provide the functionality of a number of servers that is not directly bound to the number of computers in the computing device 3200. For example, virtualization software may provide twenty virtual servers on four physical computers. In an embodiment, the functionality disclosed above may be provided by executing the application and/or applications in a cloud computing environment. Cloud computing may comprise providing computing services via a network connection using dynamically scalable computing resources. Cloud computing may be supported, at least in part, by virtualization software. A cloud computing environment may be established by an enterprise and/or may be hired on an as-needed basis from a third-party provider. Some cloud computing environments may comprise cloud computing resources owned and operated by the enterprise as well as cloud computing resources hired and/or leased from a third-party provider.

In its most basic configuration, computing device 3200 typically includes at least one processing unit 3220 and system memory 3230. Depending on the exact configuration and type of computing device, system memory 3230 may be volatile (such as random access memory (RAM)), non-volatile (such as read-only memory (ROM), flash memory, etc.), or some combination of the two. This most basic configuration is illustrated in FIG. 32 by dashed line 3210. The processing unit 3220 may be a standard programmable processor that performs arithmetic and logic operations necessary for operation of the computing device 3200. While only one processing unit 3220 is shown, multiple processors may be present. Thus, while instructions may be discussed as executed by a processor, the instructions may be executed simultaneously, serially, or otherwise executed by one or multiple processors. The computing device 3200 may also include a bus or other communication mechanism for communicating information among various components of the computing device 3200.

Computing device 3200 may have additional features/ functionality. For example, computing device 3200 may include additional storage such as removable storage 3240 and non-removable storage 3250 including, but not limited to, magnetic or optical disks or tapes. Computing device 3200 may also contain network connection(s) 3280 that allow the device to communicate with other devices such as over the communication pathways described herein. The network connection(s) 3280 may take the form of modems, modem banks, Ethernet cards, universal serial bus (USB) interface cards, serial interfaces, token ring cards, fiber distributed data interface (FDDI) cards, wireless local area network (WLAN) cards, radio transceiver cards such as code division multiple access (CDMA), global system for mobile communications (GSM), long-term evolution (LTE), worldwide interoperability for microwave access (WiMAX), and/or other air interface protocol radio transceiver cards, and other well-known network devices. Computing device 3200 may also have input device(s) 3270 such as keyboards, keypads, switches, dials, mice, track balls, touch screens, voice recognizers, card readers, paper tape readers, or other well-known input devices. Output device(s) 3260 such as printers, video monitors, liquid crystal displays (LCDs), touch screen displays, displays, speakers, etc. may also be included. The additional devices may be connected to the bus in order to facilitate communication of data among the components of the computing device 3200. All these devices are well known in the art and need not be discussed at length here.

The processing unit 3220 may be configured to execute program code encoded in tangible, computer-readable media. Tangible, computer-readable media refers to any media that is capable of providing data that causes the computing device 3200 (i.e., a machine) to operate in a particular fashion. Various computer-readable media may be utilized to provide instructions to the processing unit 3220 for execution. Example tangible, computer-readable media may include, but is not limited to, volatile media, non-volatile media, removable media and non-removable media implemented in any method or technology for storage of information such as computer readable instructions, data structures, program modules or other data. System memory 3230, removable storage 3240, and non-removable storage 3250 are all examples of tangible, computer storage media. Example tangible, computer-readable recording media include, but are not limited to, an integrated circuit (e.g., field-programmable gate array or application-specific IC), a hard disk, an optical disk, a magneto-optical disk, a floppy disk, a magnetic tape, a holographic storage medium, a solid-state device, RAM, ROM, electrically erasable program read-only memory (EEPROM), flash memory or other memory technology, CD-ROM, digital versatile disks (DVD) or other optical storage, magnetic cassettes, magnetic tape, magnetic disk storage or other magnetic storage devices.

It is fundamental to the electrical engineering and software engineering arts that functionality that can be implemented by loading executable software into a computer can be converted to a hardware implementation by well-known design rules. Decisions between implementing a concept in software versus hardware typically hinge on considerations of stability of the design and numbers of units to be produced rather than any issues involved in translating from the software domain to the hardware domain. Generally, a design that is still subject to frequent change may be preferred to be implemented in software, because re-spinning a hardware implementation is more expensive than re-spinning a software design. Generally, a design that is stable that will be produced in large volume may be preferred to be implemented in hardware, for example in an application specific integrated circuit (ASIC), because for large production runs the hardware implementation may be less expensive than the software implementation. Often a design may be developed and tested in a software form and later transformed, by well-known design rules, to an equivalent hardware implementation in an application specific integrated circuit that hardwires the instructions of the software. In the same manner as a machine controlled by a new ASIC is a particular machine or apparatus, likewise a computer that has been programmed and/or loaded with executable instructions may be viewed as a particular machine or apparatus.

In an example implementation, the processing unit 3220 may execute program code stored in the system memory 3230. For example, the bus may carry data to the system memory 3230, from which the processing unit 3220 receives and executes instructions. The data received by the system memory 3230 may optionally be stored on the removable storage 3240 or the non-removable storage 3250 before or after execution by the processing unit 3220.

It should be understood that the various techniques described herein may be implemented in connection with hardware or software or, where appropriate, with a combination thereof. Thus, the methods and apparatuses of the presently disclosed subject matter, or certain aspects or portions thereof, may take the form of program code (i.e., instructions) embodied in tangible media, such as floppy diskettes, CD-ROMs, hard drives, or any other machine-readable storage medium wherein, when the program code is loaded into and executed by a machine, such as a computing device, the machine becomes an apparatus for practicing the presently disclosed subject matter. In the case of program code execution on programmable computers, the computing device generally includes a processor, a storage medium readable by the processor (including volatile and non-volatile memory and/or storage elements), at least one input device, and at least one output device. One or more programs may implement or utilize the processes described in connection with the presently disclosed subject matter, e.g., through the use of an application programming interface (API), reusable controls, or the like. Such programs may be implemented in a high-level procedural or object-oriented programming language to communicate with a computer system. However, the program(s) can be implemented in assembly or machine language, if desired. In any case, the language may be a compiled or interpreted language and it may be combined with hardware implementations.

Embodiments of the methods and systems may be described herein with reference to block diagrams and flowchart illustrations of methods, systems, apparatuses and computer program products. It will be understood that each block of the block diagrams and flowchart illustrations, and combinations of blocks in the block diagrams and flowchart illustrations, respectively, can be implemented by computer program instructions. These computer program instructions may be loaded onto a general-purpose computer, special purpose computer, or other programmable data processing apparatus to produce a machine, such that the instructions which execute on the computer or other programmable data processing apparatus create a means for implementing the functions specified in the flowchart block or blocks.

These computer program instructions may also be stored in a computer-readable memory that can direct a computer or other programmable data processing apparatus to function in a particular manner, such that the instructions stored in the computer-readable memory produce an article of manufacture including computer-readable instructions for implementing the function specified in the flowchart block or blocks. The computer program instructions may also be loaded onto a computer or other programmable data processing apparatus to cause a series of operational steps to be performed on the computer or other programmable apparatus to produce a computer-implemented process such that the instructions that execute on the computer or other programmable apparatus provide steps for implementing the functions specified in the flowchart block or blocks.

Accordingly, blocks of the block diagrams and flowchart illustrations support combinations of means for performing the specified functions, combinations of steps for performing the specified functions and program instruction means for performing the specified functions. It will also be understood that each block of the block diagrams and flowchart illustrations, and combinations of blocks in the block diagrams and flowchart illustrations, can be implemented by special purpose hardware-based computer systems that perform the specified functions or steps, or combinations of special purpose hardware and computer instructions.

Use of the phrase "and/or" indicates that anyone or any combination of a list of options can be used. For example, "A, B, and/or C" means "A", or "B", or "C", or "A and B", or "A and C", or "B and C", or "A and B and C". As used in the specification, the singular forms "a," "an" and "the" include plural referents unless the context clearly dictates otherwise. Moreover, titles or subtitles may be used in this specification for the convenience of a reader, which shall have no influence on the scope of the disclosed technology. By "comprising" or "containing" or "including" is meant that at least the named compound, element, particle, or method step is present in the composition or article or method, but does not exclude the presence of other compounds, materials, particles, method steps, even if the other such compounds, material, particles, method steps have the same function as what is named.

In describing example embodiments, terminology will be resorted to for the sake of clarity. It is intended that each term contemplates its broadest meaning as understood by those skilled in the art and includes all technical equivalents that operate in a similar manner to accomplish a similar purpose.

It is to be understood that the mention of one or more steps of a method does not preclude the presence of additional method steps or intervening method steps between those steps expressly identified. Steps of a method may be performed in a different order than those described herein. Similarly, it is also to be understood that the mention of one or more components in a device or system does not preclude the presence of additional components or intervening components between those components expressly identified.

While several embodiments have been provided in the present disclosure, it should be understood that the disclosed systems and methods may be embodied in many other specific forms without departing from the spirit or scope of the present disclosure. The present examples are to be considered as illustrative and not restrictive, and the intention is not to be limited to the details given herein. For example, the various elements or components may be combined or integrated in another system or certain features may be omitted or not implemented.

Also, techniques, systems, subsystems, and methods described and illustrated in the various embodiments as discrete or separate may be combined or integrated with other systems, modules, techniques, or methods without departing from the scope of the present disclosure. Other items shown or discussed as directly coupled or communicating with each other may be indirectly coupled or communicating through some interface, device, or intermediate component, whether electrically, mechanically, or otherwise. Other examples of changes, substitutions, and alterations are ascertainable by one skilled in the art and could be made without departing from the spirit and scope disclosed herein.

Unless otherwise expressly stated, it is in no way intended that any method set forth herein be construed as requiring that its steps be performed in a specific order. Accordingly, where a method claim does not actually recite an order to be followed by its steps or it is not otherwise specifically stated in the claims or descriptions that the steps are to be limited to a specific order, it is no way intended that an order be inferred, in any respect. This holds for any possible non-express basis for interpretation, including: matters of logic with respect to arrangement of steps or operational flow; plain meaning derived from grammatical organization or punctuation; the number or type of embodiments described in the specification.

It is contemplated that the disclosure herein can be used in the design of MR/RF coils optimized for acquisition of myelin isolated MR signal. The disclosure herein can also be used with any other multi modal biomedical imaging device that has windowed acquisition of data informed by myelin siMRI, such as a FUS or MR/LINACS with megavoltage image capacities etc).

It is contemplated that the disclosure herein can be used for other non in vivo imaging devices, such as microscopes, SQUIDS or other quantum flux devices, that can be designed to detect a siMRI signal of myelin to differentiate myelination in tumor bed tissue during cancer resection, for example.

It is contemplated that the disclosure can be used with other mathematical transformation of the data, including for example, but not limited to, Laplacian, Hough, Radon, wavelet, sine or cosine transformations, etc., to take the data to a biologically isolatable space, e.g., to isolate myelin-signals to reveal in vivo myelin compaction in MRI system and/or to isolate other biological measurand-signals-of-interest to reveal in vivo imaging of such measurand in a biological system.

Throughout this application, and at the end thereof, various publications are referenced. The disclosures of these publications in their entireties are hereby incorporated by reference into this application in order to more fully describe the state of the art to which the methods and systems pertain.

What is claimed is:

1. A method for in-vivo imaging of myelin, the method comprising:
   obtaining, by one or more processors, magnetic resonance data acquired from a magnetic resonance system;
   generating, by the one or more processors, at least one k-space map of the obtained magnetic resonance data;
   determining, by the one or more processors, myelin-associated regions of the at least one k-space map;
   amplifying, by the one or more processors, spatiotemporal signatures of magnetic relaxation associated with myelin-restricted water at the determined myelin-associated regions of the at least one k-space map, or components thereof, to generate a myelin-amplified k-space map; and
   reconstructing, by the one or more processors, in part, the myelin-amplified k-space map to generate a myelin-amplified MRI quantification and/or visualization dataset of myelin associated tissue structure;
   wherein the reconstructed myelin-amplified MRI quantification and/or visualization dataset of the myelin associated tissue structure are outputted to a display or to storage, and
   wherein the myelin-associated regions of the at least one k-space map are determined by:
   iteratively applying, by the one or more processors, a plurality of evaluative patches to the at least one k-space map, wherein in each successive stage, a different one of the plurality of evaluative patches is applied to the at least one k-space map to produce a modified k-space map;

reconstructing, by the one or more processors, at each iteration of the successive stages, a first MRI image or dataset from the modified k-space map;

evaluating, by the one or more processors, at each iteration of the successive stages, an intensity value associated with one or more myelin-associated regions of interests in the reconstructed first MRI image or dataset;

selecting, by the one or more processors, one or more evaluative patches of the plurality of evaluative patches, wherein the one or more evaluative patches comprise a saturating patch or a nulling patch having, respectively, a global maximum or global minimum of the intensity values; and shaping, by the one or more processors, the one or more selected evaluative patches to correspond to the myelin-associated regions of the at least one k-space map.

2. The method of claim 1, wherein the magnetic resonance data comprises T1 measurement values, and wherein the step of amplifying the spatiotemporal signatures of magnetic relaxation associated with myelin-restricted water includes amplifying based on an amplification profile of the T1 measurement values.

3. The method of claim 2, wherein the step of amplifying the spatiotemporal signatures of magnetic relaxation associated with myelin-restricted water, including in the periaxonal compartments, further includes suppressing at least one non-myelin related signature.

4. The method of claim 1, wherein an evaluative patch of the one or more evaluative patches has a spiral pattern, asymmetric distribution pattern, or a polygonal shape.

5. The method of claim 1,
wherein the generating, by the one or more processors, the at least one k-space map of the obtained magnetic resonance data is for each slice of a magnetic resonance data set;
wherein the amplifying, by the one or more processors, the spatiotemporal signatures of magnetic relaxation associated with myelin-restricted water at the determined myelin-associated regions of the at least one k-space map, or components thereof, to generate the myelin-amplified k-space map is performed for each slice of the magnetic resonance data set; and
wherein the reconstructing, by the one or more processors, the myelin-amplified k-space map to generate the MRI quantification and/or visualization dataset of myelin associated tissue structure is of each slice of the magnetic resonance data set, and
wherein the reconstructed myelin-amplified MRI quantification and/or visualization dataset is a three-dimensional MRI quantification and/or visualization.

6. The method of claim 1, comprising:
co-registering, by the one or more processors, the reconstructed myelin-amplified MRI quantification and/or visualization dataset of the myelin associated structure with a second MRI modality, wherein the reconstructed myelin-amplified MRI quantification and/or visualization dataset of the myelin associated structure is subsequently overlaid over MRI visualization of the second MRI modality.

7. The method of claim 1, further comprising:
calculating, by the one or more processors, one or more metrics comprising i) one or more myelin compaction indices derived from the reconstructed myelin-amplified MRI quantification and/or visualization data dataset of the myelin associated structure or ii) other MRI quantities;
wherein the calculated one or more metrics is outputted to the display or to the storage for subsequent display and/or analysis.

8. The method of claim 1, wherein the reconstructed myelin-amplified MRI quantification and/or visualization dataset includes a myelin compaction map or a myelin compaction dataset.

9. The method of claim 1 further comprising:
generating, by the one or more processors, a fiber tractography image based on the reconstructed myelin-amplified MRI quantification and/or visualization dataset of the myelin associated tissue structure.

10. The method of claim 1, wherein the reconstructed myelin-amplified MRI quantification and/or visualization dataset include visualization of myelin integrity including visualization and/or quantified data of intact myelin, degenerating myelin, and regenerating myelin when present in a subject associated with the obtained magnetic resonance data.

11. The method of claim 1, wherein the reconstructed myelin-amplified MRI quantification and/or visualization dataset include visualization and/or quantified data of myelin degeneration when myelin degeneration is present in a subject associated with the obtained magnetic resonance data.

12. The method of claim 1, wherein the reconstructed myelin-amplified MRI quantification and/or visualization dataset include visualization and/or quantified data of myelin plasticity, or associated degradation thereof, and wherein the reconstructed myelin-amplified MRI quantification and/or visualization dataset of the myelin associated tissue structure is used to inform a myelin structure-related pathology or condition selected from the group consisting of multiple sclerosis, Parkinson's disease, Alzheimer's disease, spinal cord injury, brain injury, concussion, mild repeated neural injury, cancer of the nervous system, myelopathy, white matter/axonal damage after surgery of the nervous system, age-related cognitive decline, and age-related motor decline.

13. The method of claim 1, wherein the reconstructed myelin-amplified MRI quantification and/or visualization dataset of the myelin associated tissue structure is used to:
inform at least one of:
a myelin structure-related evaluation of post tumor resection margins, post-surgery and/or post radiotherapy in the nervous system or in nerves of the body;
myelin-related developmental assessments;
prenatal assessment of neurological development; or
detect or inform at least one of:
myelin-related developmental disorders;
improvements of life style changes;
exercise performance;
drug addiction;
drug efficacy;
neuronal function in developmental population;
motor learning, therapy;
behavior; and
athletic performance.

14. The method of claim 1, wherein the magnetic resonance data comprises one or more echo measurements and/or one or more weighted MR maps each having one or more magnetic-resonance contrast data selected from the group consisting of T1 data, T2 data, T2* data, MR diffusion data, MPRAGE data, gradient-echo data, spin-echo data, EPI data, BOLD data, proton density data, susceptibility data, magnetization transfer data, spin labeling data, flow data, and combination thereof.

15. The method of claim 1, wherein the reconstructed myelin-amplified MRI quantification and/or visualization dataset of the myelin associated tissue structure are outputted to the display or to storage for at least one of i) subsequent display or analysis or optimizing sequences of coil, ii) design, organized, classified, and/or stored on a data library/collection for learning, iii) comparative learning, machine learning, or digital memory of research, and iv) medically relevant knowledge buildup.

16. The method of claim 1, wherein the shaping of the selected patch to correspond to the myelin-associated region of the at least one k-space map is performed by:
   (i) calculating a T2 relaxometry value for a plurality of points in the selected patch;
   (ii) evaluating a fit, via a fit function of each of the calculated T2 relaxometry value among the plurality of calculated T2 relaxometry values associated with the points; and
   (iii) adding one or more points in the selected patch to the myelin-associated region of the k-space map based on the evaluated fit.

17. The method of claim 1, wherein the myelin-associated regions of the k-space map are determined by evaluating and removing, by the one or more processors, portions of the at least one k-space map that does affect measured values.

18. The method of claim 12, wherein the myelin structure-related pathology or condition is multiple sclerosis.

19. A system comprising:
   one or more processors; and
   a memory having instructions stored thereon, wherein execution of the instructions by the one or more processors cause the one or more processors to:
   obtain magnetic resonance data acquired from a magnetic resonance system;
   generate at least one k-space map of the obtained magnetic resonance data;
   determine myelin-associated regions of the at least one k-space map;
   amplify spatiotemporal signatures of magnetic relaxation associated with myelin-restricted water at the determined myelin-associated regions of the at least one k-space map, or components thereof, to generate a myelin-amplified k-space map; and
   reconstruct, in part, the myelin-amplified k-space map to generate a myelin-amplified MRI quantification and/or visualization dataset of myelin associated tissue structure;
   wherein the reconstructed myelin-amplified MRI quantification and/or visualization dataset of the myelin associated tissue structure are outputted to a display or to storage, and
   wherein the myelin-associated regions of the at least one k-space map are determined by:
   iteratively applying, by the one or more processors, a plurality of evaluative patches to the at least one k-space map, wherein in each successive stage, a different one of the plurality of evaluative patches is applied to the at least one k-space map to produce a modified k-space map;
   reconstruct at each iteration of the successive stages, a first MRI image or dataset from the modified k-space map;
   evaluate at each iteration of the successive stages an intensity value associated with one or more myelin-associated regions of interest in the reconstructed first MRI image or dataset;
   selecting, by the one or more processors, one or more evaluative patches of the plurality of evaluative patches, wherein the one or more evaluative patches comprise a saturating patch or a nulling patch having, respectively, a global maximum or global minimum of the intensity values among a set of the intensity values determined for the plurality of evaluative patches; and
   shape the one or more selected evaluative patches to correspond to the myelin-associated regions of the at least one k-space map.

20. A non-transitory computer readable medium having instructions stored thereon, wherein execution of the instructions by a processor cause the one or more processors to:
   obtain magnetic resonance data acquired from a magnetic resonance system;
   generate at least one k-space map of the obtained magnetic resonance data;
   determine myelin-associated regions of the at least one k-space map;
   amplify spatiotemporal signatures of magnetic relaxation associated with myelin-restricted water at the determined myelin-associated regions of the at least one k-space map, or components thereof, to generate a myelin-amplified k-space map; and
   reconstruct, in part, the myelin-amplified k-space map to generate a myelin-amplified MRI quantification and/or visualization dataset of myelin associated tissue structure;
   wherein the reconstructed myelin-amplified MRI quantification and/or visualization dataset of the myelin associated tissue structure are outputted to a display or to storage, and
   wherein the myelin-associated regions of the at least one k-space map are determined by:
   iteratively applying, by the one or more processors, a plurality of evaluative patches to the at least one k-space map, wherein in each successive stage, a different one of the plurality of evaluative patches is applied to the at least one k-space map to produce a modified k-space map;
   reconstruct at each iteration of the successive stages, a first MRI image or dataset from the modified k-space map;
   evaluate at each iteration of the successive stages an intensity value associated with one or more myelin-associated regions of interest in the reconstructed first MRI image or dataset;
   selecting, by the one or more processors, one or more evaluative patches of the plurality of evaluative patches, wherein the one or more evaluative patches comprise a saturating patch or a nulling patch having, respectively, a global maximum or global minimum of the intensity values among a set of the intensity values determined for the plurality of evaluative patches; and
   shape the one or more selected evaluative patches to correspond to the myelin-associated regions of the at least one k-space map.

* * * * *